(12) United States Patent
Uemori et al.

(10) Patent No.: US 6,333,158 B1
(45) Date of Patent: *Dec. 25, 2001

(54) DNA POLYMERASE-RELATED FACTORS

(75) Inventors: Takashi Uemori, Otsu; Yoshimi Sato, Kurita-gun; Tomoko Fujita, Takatsuki; Kazue Miyake, Uji; Hiroyuki Mukai, Moriyama; Kiyozo Asada, Koga-gun; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/712,266

(22) Filed: Nov. 15, 2000

Related U.S. Application Data

(63) Continuation of application No. 09/446,504, filed as application No. PCT/JP98/02845 on Jun. 24, 1998, now Pat. No. 6,218,150.

(30) Foreign Application Priority Data

Jun. 26, 1997 (JP) .................................................. 9-187496
Nov. 27, 1997 (JP) .................................................. 9-320692

(51) Int. Cl.[7] .............................. C12Q 1/68; C12P 19/34; C07H 21/02; C07H 21/04; A61K 38/43
(52) U.S. Cl. .......................... 435/6; 435/91.1; 435/91.2; 536/22.1; 536/23.1; 424/94.1
(58) Field of Search ........................... 435/6, 91.1, 91.2; 536/22.1, 23.1; 424/94.1

(56) References Cited

U.S. PATENT DOCUMENTS 6,128,150 * 4/2001 Uemori et al. ...................... 435/91.1

FOREIGN PATENT DOCUMENTS

0821058 A2  1/1998  (EP) .
10-84954A   4/1998  (JP) .

OTHER PUBLICATIONS

WO97/24444 Pamphlet (English Abstract Only).
Nucleic Acids Research, 21, 259–265 (1993).
J. Bacteriol., 177, 2164–2177 (1995).
Science, 269, 496–512 (1995).
Journal of Bacteriology, 178, 5781–5786 (1986).
Science, 272, 408–411 (1996).
EMBO J., 11, 5111–5119 (1995).
Proc. Natl. Acad. Sci. USA, 84, 1575–1579 (1987).
Seikagaku, 68, 1542–1548 (1996) (with partial English translation).
Science, 273, 1058–1073 (1996).
Nucleic Acids Research, 21, 1–3 (1993).
Nucleic Acids Research, 22, 1527–1535 (1994).
Nucleic Acids Research, 18, 261–265 (1990).
The Journal of Japanese Biochemical Society vol. 68, No. 9 (1996) Hiroshi Morioka "Structure and function of proliferating cell nuclear antigen (PCNA)" p. 1542–1548.

* cited by examiner

*Primary Examiner*—Jeffrey Fredman
*Assistant Examiner*—Arun Chakrabarti
(74) *Attorney, Agent, or Firm*—Birch, Stewart, Kolasch & Birch, LLP

(57) ABSTRACT

The present invention relates to a thermostable DNA polymerase-associated factor capable of enhancing DNA synthesizing-activity of a DNA polymerase; a thermostable DNA polymerase-associated factor possessing an activity of binding to a DNA polymerase and a method for producing the same; a gene encoding the DNA polymerase-associated factor; a method of DNA synthesis by using a DNA polymerase in the presence of the DNA polymerase-associated factor; and a kit comprising the DNA polymerase-associated factor. According to the present invention, there can be provided in vitro DNA synthesis and a DNA amplification system which are more excellent than conventional techniques by utilizing the DNA polymerase-associated factor of the present invention.

15 Claims, 17 Drawing Sheets

Molecular
Weight
Marker

97K —

60 — ═ PFU—RFCLS

45 —

▬ PFU-RFC
— F7

SEQUENCE LISTING

<160> NUMBER OF SEQ ID NOS: 92

<210> SEQ ID NO 1
<211> LENGTH: 249
<212> TYPE: PRT
<213> ORGANISM: Pyrococcus furiosus

<400> SEQUENCE: 1

```
Met Pro Phe Glu Ile Val Phe Glu Gly Ala Lys Glu Phe Ala Gln Leu
 1               5                  10                  15

Ile Asp Thr Ala Ser Lys Leu Ile Asp Glu Ala Ala Phe Lys Val Thr
            20                  25                  30

Glu Asp Gly Ile Ser Met Arg Ala Met Asp Pro Ser Arg Val Val Leu
        35                  40                  45

Ile Asp Leu Asn Leu Pro Ser Ser Ile Phe Ser Lys Tyr Glu Val Val
    50                  55                  60

Glu Pro Glu Thr Ile Gly Val Asn Met Asp His Leu Lys Lys Ile Leu
65                  70                  75                  80

Lys Arg Gly Lys Ala Lys Asp Thr Leu Ile Leu Lys Lys Gly Glu Glu
                85                  90                  95

Asn Phe Leu Glu Ile Thr Ile Gln Gly Thr Ala Thr Arg Thr Phe Arg
            100                 105                 110

Val Pro Leu Ile Asp Val Glu Glu Met Glu Val Asp Leu Pro Glu Leu
        115                 120                 125

Pro Phe Thr Ala Lys Val Val Leu Gly Glu Val Leu Lys Asp Ala
    130                 135                 140

Val Lys Asp Ala Ser Leu Val Ser Asp Ser Ile Lys Phe Ile Ala Arg
145                 150                 155                 160
```

Glu Asn Glu Phe Ile Met Lys Ala Glu Gly Thr Gln Glu Val Glu
                165                 170                 175

Ile Lys Leu Thr Leu Glu Asp Glu Gly Leu Leu Asp Ile Glu Val Gln
            180                 185                 190

Glu Glu Thr Lys Ser Ala Tyr Gly Val Ser Tyr Leu Ser Asp Met Val
            195                 200                 205

Lys Gly Leu Gly Lys Ala Asp Glu Val Thr Ile Lys Phe Gly Asn Glu
        210                 215                 220

Met Pro Met Gln Met Glu Tyr Tyr Ile Arg Asp Glu Gly Arg Leu Thr
225                 230                 235                 240

Phe Leu Leu Ala Pro Arg Val Glu Glu
                245

<210> SEQ ID NO 2
<211> LENGTH: 750
<212> TYPE: DNA
<213> ORGANISM: Pyrococcus furiosus

<400> SEQUENCE: 2
atgccatttg aaatcgtatt tgaaggtgca aaagagtttg cccaacttat agacaccgca       60
agtaagttaa tagatgaggc cgcgtttaaa gttacagaag atgggataag catgagggcc      120
atggatccaa gtagagttgt cctgattgac ctaaatctcc cgtcaagcat atttagcaaa      180
tatgaagttt tgaaccagaa acaattgga gttaacatgg accacctaaa gaagatccta      240
aagagaggta agcaaagga caccttaata ctcaagaaag gagaggaaaa cttcttagag      300
ataacaattc aaggaactgc aacaagaaca tttagagttc ccctaataga tgtagaagag      360
atggaagttg acctcccaga acttccattc actgcaaagg ttgtagttct tggagaagtc      420
ctaaaagatg ctgttaaaga tgcctctcta gtgagtgaca gcataaaatt tattgccagg      480
gaaaatgaat ttataatgaa ggcagaggga gaaacccagg aagttgagat aaagctaact      540
cttgaagatg agggattatt ggacatcgag gttcaagagg agacaaagag cgcatatgga      600
gtcagctatc tctccgacat ggttaaagga cttggaaagg ccgatgaagt tacaataaag      660
tttggaaatg aaatgcccat gcaaatggag tattacatta gagatgaagg aagacttaca      720
ttcctactgg ctccaagagt tgaagagtga                                       750

<210> SEQ ID NO 3
<211> LENGTH: 327
<212> TYPE: PRT
<213> ORGANISM: Pyrococcus furiosus

<400> SEQUENCE: 3

Met Ser Glu Glu Ile Arg Glu Val Lys Val Leu Glu Lys Pro Trp Val
1               5                  10                  15

Glu Lys Tyr Arg Pro Gln Arg Leu Asp Asp Ile Val Gly Gln Glu His
            20                  25                  30

Ile Val Lys Arg Leu Lys His Tyr Val Lys Thr Gly Ser Met Pro His
        35                  40                  45

Leu Leu Phe Ala Gly Pro Pro Gly Val Gly Lys Thr Thr Ala Ala Leu
    50                  55                  60

Ala Leu Ala Arg Glu Leu Phe Gly Glu Asn Trp Arg His Asn Phe Leu
65                  70                  75                  80

Glu Leu Asn Ala Ser Asp Glu Arg Gly Ile Asn Val Ile Arg Glu Lys
                85                  90                  95

| | | | | | | | | | | | |
|---|---|---|---|---|---|---|---|---|---|---|---|
|Val|Lys|Glu|Phe|Ala|Arg|Thr|Lys|Pro|Ile|Gly|Gly|Ala|Ser|Phe|Lys|
| | | |100| | | |105| | | |110|

Val Lys Glu Phe Ala Arg Thr Lys Pro Ile Gly Gly Ala Ser Phe Lys
                  100                105                110

Ile Ile Phe Leu Asp Glu Ala Asp Ala Leu Thr Gln Asp Ala Gln Gln
 115                       120                    125

Ala Leu Arg Arg Thr Met Glu Met Phe Ser Ser Asn Val Arg Phe Ile
 130                       135                140

Leu Ser Cys Asn Tyr Ser Ser Lys Ile Ile Glu Pro Ile Gln Ser Arg
145                  150                155               160

Cys Ala Ile Phe Arg Phe Arg Pro Leu Arg Asp Glu Asp Ile Ala Lys
              165                170               175

Arg Leu Arg Tyr Ile Ala Glu Asn Glu Gly Leu Glu Leu Thr Glu Glu
         180                    185               190

Gly Leu Gln Ala Ile Leu Tyr Ile Ala Glu Gly Asp Met Arg Arg Ala
     195                 200                205

Ile Asn Ile Leu Gln Ala Ala Ala Leu Asp Lys Lys Ile Thr Asp
 210                      215                220

Glu Asn Val Phe Met Val Ala Ser Arg Ala Arg Pro Glu Asp Ile Arg
225                  230                235               240

Glu Met Met Leu Leu Ala Leu Lys Gly Asn Phe Leu Lys Ala Arg Glu
              245                250               255

Lys Leu Arg Glu Ile Leu Leu Lys Gln Gly Leu Ser Gly Glu Asp Val
         260                    265               270

Leu Val Gln Met His Lys Glu Val Phe Asn Leu Pro Ile Glu Pro
     275                 280                285

Lys Lys Val Leu Leu Ala Asp Lys Ile Gly Glu Tyr Asn Phe Arg Leu
 290                      295                300

Val Glu Gly Ala Asn Glu Ile Ile Gln Leu Glu Ala Leu Leu Ala Gln
305                  310                315               320

Phe Thr Leu Ile Gly Lys Lys
              325

<210> SEQ ID NO 4
<211> LENGTH: 984
<212> TYPE: DNA
<213> ORGANISM: Pyrococcus furiosus

<400> SEQUENCE: 4

```
atgagcgaag agattagaga agttaaggtt ctagaaaaac cctgggttga gaagtataga    60
cctcaaagac ttgacgacat tgtaggacaa gagcacatag tgaaaaggct caagcactac   120
gtcaaaactg gatcaatgcc ccacctactc ttcgcaggcc cccctggtgt cggaaagact   180
acagcggctt tggcccttgc aagagagctt ttcggcgaaa actggaggca taacttcctc   240
gagttgaatg cttcagatga agaggtata aacgtaatta gagagaaagt taaggagttt   300
gcgagaacaa agcctatagg aggagcaagc ttcaagataa ttttccttga tgaggccgac   360
gctttaactc aagatgccca acaagcctta agaagaacca tggaaatgtt ctcgagtaac   420
gttcgcttta tcttgagctg taactactcc tccaagataa ttgaacccat acagtctaga   480
tgtgcaatat tccgcttcag acctctccgc gatgaggata tagcgaagag actaaggtac   540
attgccgaaa atgagggctt agagctaact gaagaaggtc tccaagcaat actttacata   600
gcagaaggag atatgagaag agcaataaac attctgcaag ctgcagcagc tctagacaag   660
aagatcaccg acgaaaacgt attcatggta gcgagtagag ctagacctga agatataaga   720
gagatgatgc ttcttgctct caaaggcaac ttcttgaagg ccagagaaaa gcttagggag   780
```

-continued

```
atacttctca agcaaggact tagtggagaa gatgtactag ttcagatgca caaagaagtc      840
ttcaacctgc caatagagga gccaaagaag gttctgcttg ctgataagat aggagagtat      900
aacttcagac tcgttgaagg ggctaatgaa ataattcagc ttgaagcact cttagcacag      960
ttcaccctaa ttgggaagaa gtga                                             984
```

<210> SEQ ID NO 5
<211> LENGTH: 613
<212> TYPE: PRT
<213> ORGANISM: Pyrococcus furiosus

<400> SEQUENCE: 5

```
Met Asp Glu Phe Val Lys Ser Leu Leu Lys Ala Asn Tyr Leu Ile Thr
  1               5                  10                  15

Pro Ser Ala Tyr Tyr Leu Leu Arg Glu Tyr Tyr Glu Lys Gly Glu Phe
                 20                  25                  30

Ser Ile Val Glu Leu Val Lys Phe Ala Arg Ser Arg Glu Ser Tyr Ile
             35                  40                  45

Ile Thr Asp Ala Leu Ala Thr Glu Phe Leu Lys Val Lys Gly Leu Glu
         50                  55                  60

Pro Ile Leu Pro Val Glu Thr Lys Gly Gly Phe Val Ser Thr Gly Glu
 65                  70                  75                  80

Ser Gln Lys Glu Gln Ser Tyr Glu Glu Ser Phe Gly Thr Lys Glu Glu
                 85                  90                  95

Ile Ser Gln Glu Ile Lys Glu Gly Glu Ser Phe Ile Ser Thr Gly Ser
                100                 105                 110

Glu Pro Leu Glu Glu Glu Leu Asn Ser Ile Gly Ile Glu Glu Ile Gly
            115                 120                 125

Ala Asn Glu Glu Leu Val Ser Asn Gly Asn Asp Asn Gly Gly Glu Ala
        130                 135                 140

Ile Val Phe Asp Lys Tyr Gly Tyr Pro Met Val Tyr Ala Pro Glu Glu
145                 150                 155                 160

Ile Glu Val Glu Glu Lys Glu Tyr Ser Lys Tyr Glu Asp Leu Thr Ile
                165                 170                 175

Pro Met Asn Pro Asp Phe Asn Tyr Val Glu Ile Lys Glu Asp Tyr Asp
            180                 185                 190

Val Val Phe Asp Val Arg Asn Val Lys Leu Lys Pro Pro Lys Val Lys
        195                 200                 205

Asn Gly Asn Gly Lys Glu Gly Glu Ile Ile Val Glu Ala Tyr Ala Ser
    210                 215                 220

Leu Phe Arg Ser Arg Leu Lys Lys Leu Arg Lys Ile Leu Arg Glu Asn
225                 230                 235                 240

Pro Glu Leu Asp Asn Val Val Asp Ile Gly Lys Leu Lys Tyr Val Lys
                245                 250                 255

Glu Asp Glu Thr Val Thr Ile Ile Gly Leu Val Asn Ser Lys Arg Glu
            260                 265                 270

Val Asn Lys Gly Leu Ile Phe Gly Ile Glu Asp Leu Thr Gly Lys Val
        275                 280                 285

Lys Val Phe Leu Pro Lys Asp Ser Glu Asp Tyr Arg Glu Ala Phe Lys
    290                 295                 300

Val Leu Pro Asp Ala Val Ala Phe Lys Gly Val Tyr Ser Lys Arg
305                 310                 315                 320

Gly Ile Leu Tyr Ala Asn Lys Phe Tyr Leu Pro Asp Val Pro Leu Tyr
                325                 330                 335
```

```
Arg Arg Gln Lys Pro Leu Glu Glu Lys Val Tyr Ala Ile Leu Ile
            340                 345                 350

Ser Asp Ile His Val Gly Ser Lys Glu Phe Cys Glu Asn Ala Phe Ile
            355                 360                 365

Lys Phe Leu Glu Trp Leu Asn Gly Asn Val Glu Thr Lys Glu Glu
            370                 375                 380

Glu Ile Val Ser Arg Val Lys Tyr Leu Ile Ala Gly Asp Val Val
385                 390                 395                 400

Asp Gly Val Gly Val Tyr Pro Gly Gln Tyr Ala Asp Leu Thr Ile Pro
                    405                 410                 415

Asp Ile Phe Asp Gln Tyr Glu Ala Leu Ala Asn Leu Leu Ser His Val
            420                 425                 430

Pro Lys His Ile Thr Met Phe Ile Ala Pro Gly Asn His Asp Ala Ala
            435                 440                 445

Arg Gln Ala Ile Pro Gln Pro Glu Phe Tyr Lys Glu Tyr Ala Lys Pro
            450                 455                 460

Ile Tyr Lys Leu Lys Asn Ala Val Ile Ile Ser Asn Pro Ala Val Ile
465                 470                 475                 480

Arg Leu His Gly Arg Asp Phe Leu Ile Ala His Gly Arg Gly Ile Glu
                    485                 490                 495

Asp Val Val Gly Ser Val Pro Gly Leu Thr His His Lys Pro Gly Leu
            500                 505                 510

Pro Met Val Glu Leu Leu Lys Met Arg His Val Ala Pro Met Phe Gly
            515                 520                 525

Gly Lys Val Pro Ile Ala Pro Asp Pro Glu Asp Leu Leu Val Ile Glu
            530                 535                 540

Glu Val Pro Asp Val Val His Met Gly His Val His Val Tyr Asp Ala
545                 550                 555                 560

Val Val Tyr Arg Gly Val Gln Leu Val Asn Ser Ala Thr Trp Gln Ala
                    565                 570                 575

Gln Thr Glu Phe Gln Lys Met Val Asn Ile Val Pro Thr Pro Ala Lys
            580                 585                 590

Val Pro Val Val Asp Ile Asp Thr Ala Lys Val Val Lys Val Leu Asp
            595                 600                 605

Phe Ser Gly Trp Cys
        610

<210> SEQ ID NO 6
<211> LENGTH: 1263
<212> TYPE: PRT
<213> ORGANISM: Pyrococcus furiosus

<400> SEQUENCE: 6

Met Glu Leu Pro Lys Glu Ile Glu Glu Tyr Phe Glu Met Leu Gln Arg
  1               5                  10                  15

Glu Ile Asp Lys Ala Tyr Glu Ile Ala Lys Lys Ala Arg Ser Gln Gly
                 20                  25                  30

Lys Asp Pro Ser Thr Asp Val Glu Ile Pro Gln Ala Thr Asp Met Ala
             35                  40                  45

Gly Arg Val Glu Ser Leu Val Gly Pro Pro Gly Val Ala Gln Arg Ile
         50                  55                  60

Arg Glu Leu Leu Lys Glu Tyr Asp Lys Glu Ile Val Ala Leu Lys Ile
65                  70                  75                  80

Val Asp Glu Ile Ile Glu Gly Lys Phe Gly Asp Phe Gly Ser Lys Glu
                 85                  90                  95
```

-continued

```
Lys Tyr Ala Glu Gln Ala Val Arg Thr Ala Leu Ala Ile Leu Thr Glu
            100                 105                 110
Gly Ile Val Ser Ala Pro Leu Glu Gly Ile Ala Asp Val Lys Ile Lys
        115                 120                 125
Arg Asn Thr Trp Ala Asp Asn Ser Glu Tyr Leu Ala Leu Tyr Tyr Ala
    130                 135                 140
Gly Pro Ile Arg Ser Ser Gly Gly Thr Ala Gln Ala Leu Ser Val Leu
145                 150                 155                 160
Val Gly Asp Tyr Val Arg Arg Lys Leu Gly Leu Asp Arg Phe Lys Pro
                165                 170                 175
Ser Gly Lys His Ile Glu Arg Met Val Glu Val Asp Leu Tyr His
            180                 185                 190
Arg Ala Val Ser Arg Leu Gln Tyr His Pro Ser Pro Asp Glu Val Arg
        195                 200                 205
Leu Ala Met Arg Asn Ile Pro Ile Glu Ile Thr Gly Glu Ala Thr Asp
    210                 215                 220
Asp Val Glu Val Ser His Arg Asp Val Glu Gly Val Glu Thr Asn Gln
225                 230                 235                 240
Leu Arg Gly Gly Ala Ile Leu Val Leu Ala Glu Gly Val Leu Gln Lys
                245                 250                 255
Ala Lys Lys Leu Val Lys Tyr Ile Asp Lys Met Gly Ile Asp Gly Trp
            260                 265                 270
Glu Trp Leu Lys Glu Phe Val Glu Ala Lys Glu Lys Gly Glu Glu Ile
        275                 280                 285
Glu Glu Ser Glu Ser Lys Ala Glu Glu Ser Lys Val Glu Thr Arg Val
    290                 295                 300
Glu Val Glu Lys Gly Phe Tyr Tyr Lys Leu Tyr Glu Lys Phe Arg Ala
305                 310                 315                 320
Glu Ile Ala Pro Ser Glu Lys Tyr Ala Lys Glu Ile Ile Gly Gly Arg
                325                 330                 335
Pro Leu Phe Ala Gly Pro Ser Glu Asn Gly Gly Phe Arg Leu Arg Tyr
            340                 345                 350
Gly Arg Ser Arg Val Ser Gly Phe Ala Thr Trp Ser Ile Asn Pro Ala
        355                 360                 365
Thr Met Val Leu Val Asp Glu Phe Leu Ala Ile Gly Thr Gln Met Lys
    370                 375                 380
Thr Glu Arg Pro Gly Lys Gly Ala Val Val Thr Pro Ala Thr Thr Ala
385                 390                 395                 400
Glu Gly Pro Ile Val Lys Leu Lys Asp Gly Ser Val Val Arg Val Asp
                405                 410                 415
Asp Tyr Asn Leu Ala Leu Lys Ile Arg Asp Glu Val Glu Glu Ile Leu
            420                 425                 430
Tyr Leu Gly Asp Ala Ile Ile Ala Phe Gly Asp Phe Val Glu Asn Asn
        435                 440                 445
Gln Thr Leu Leu Pro Ala Asn Tyr Val Glu Glu Trp Trp Ile Gln Glu
    450                 455                 460
Phe Val Lys Ala Val Asn Glu Ala Tyr Glu Val Glu Leu Arg Pro Phe
465                 470                 475                 480
Glu Glu Asn Pro Arg Glu Ser Val Glu Glu Ala Ala Glu Tyr Leu Glu
                485                 490                 495
Val Asp Pro Glu Phe Leu Ala Lys Met Leu Tyr Asp Pro Leu Arg Val
            500                 505                 510
```

-continued

```
Lys Pro Pro Val Glu Leu Ala Ile His Phe Ser Glu Ile Leu Glu Ile
    515                 520                 525

Pro Leu His Pro Tyr Tyr Thr Leu Tyr Trp Asn Thr Val Asn Pro Lys
    530                 535                 540

Asp Val Glu Arg Leu Trp Gly Val Leu Lys Asp Lys Ala Thr Ile Glu
545                 550                 555                 560

Trp Gly Thr Phe Arg Gly Ile Lys Phe Ala Lys Lys Ile Glu Ile Ser
                565                 570                 575

Leu Asp Asp Leu Gly Ser Leu Lys Arg Thr Leu Glu Leu Leu Gly Leu
            580                 585                 590

Pro His Thr Val Arg Glu Gly Ile Val Val Asp Tyr Pro Trp Ser
            595                 600                 605

Ala Ala Leu Leu Thr Pro Leu Gly Asn Leu Glu Trp Glu Phe Lys Ala
    610                 615                 620

Lys Pro Phe Tyr Thr Val Ile Asp Ile Ile Asn Glu Asn Asn Gln Ile
625                 630                 635                 640

Lys Leu Arg Asp Arg Gly Ile Ser Trp Ile Gly Ala Arg Met Gly Arg
                645                 650                 655

Pro Glu Lys Ala Lys Glu Arg Lys Met Lys Pro Val Gln Val Leu
            660                 665                 670

Phe Pro Ile Gly Leu Ala Gly Gly Ser Ser Arg Asp Ile Lys Lys Ala
    675                 680                 685

Ala Glu Glu Gly Lys Ile Ala Glu Val Glu Ile Ala Phe Phe Lys Cys
    690                 695                 700

Pro Lys Cys Gly His Val Gly Pro Glu Thr Leu Cys Pro Glu Cys Gly
705                 710                 715                 720

Ile Arg Lys Glu Leu Ile Trp Thr Cys Pro Lys Cys Gly Ala Glu Tyr
                725                 730                 735

Thr Asn Ser Gln Ala Glu Gly Tyr Ser Tyr Ser Cys Pro Lys Cys Asn
            740                 745                 750

Val Lys Leu Lys Pro Phe Thr Lys Arg Lys Ile Lys Pro Ser Glu Leu
    755                 760                 765

Leu Asn Arg Ala Met Glu Asn Val Lys Val Tyr Gly Val Asp Lys Leu
    770                 775                 780

Lys Gly Val Met Gly Met Thr Ser Gly Trp Lys Ile Ala Glu Pro Leu
785                 790                 795                 800

Glu Lys Gly Leu Leu Arg Ala Lys Asn Glu Val Tyr Val Phe Lys Asp
                805                 810                 815

Gly Thr Ile Arg Phe Asp Ala Thr Asp Ala Pro Ile Thr His Phe Arg
            820                 825                 830

Pro Arg Glu Ile Gly Val Ser Val Glu Lys Leu Arg Glu Leu Gly Tyr
            835                 840                 845

Thr His Asp Phe Glu Gly Lys Pro Leu Val Ser Glu Asp Gln Ile Val
    850                 855                 860

Glu Leu Lys Pro Gln Asp Val Ile Leu Ser Lys Glu Ala Gly Lys Tyr
865                 870                 875                 880

Leu Leu Arg Val Ala Arg Phe Val Asp Asp Leu Leu Glu Lys Phe Tyr
                885                 890                 895

Gly Leu Pro Arg Phe Tyr Asn Ala Glu Lys Met Glu Asp Leu Ile Gly
            900                 905                 910

His Leu Val Ile Gly Leu Ala Pro His Thr Ser Ala Gly Ile Val Gly
            915                 920                 925

Arg Ile Ile Gly Phe Val Asp Ala Leu Val Gly Tyr Ala His Pro Tyr
```

```
                930             935             940
Phe His Ala Ala Lys Arg Arg Asn Cys Asp Gly Asp Glu Asp Ser Val
945                 950                 955                 960

Met Leu Leu Leu Asp Ala Leu Leu Asn Phe Ser Arg Tyr Tyr Leu Pro
                965                 970                 975

Glu Lys Arg Gly Gly Lys Met Asp Ala Pro Leu Val Ile Thr Thr Arg
            980                 985                 990

Leu Asp Pro Arg Glu Val Asp Ser Glu Val His Asn Met Asp Val Val
        995                 1000                1005

Arg Tyr Tyr Pro Leu Glu Phe Tyr Glu Ala Thr Tyr Glu Leu Lys Ser
    1010                1015                1020

Pro Lys Glu Leu Arg Val Ile Glu Gly Val Glu Asp Arg Leu Gly
1025                1030                1035                1040

Lys Pro Glu Met Tyr Tyr Gly Ile Lys Phe Thr His Asp Thr Asp Asp
                1045                1050                1055

Ile Ala Leu Gly Pro Lys Met Ser Leu Tyr Lys Gln Leu Gly Asp Met
            1060                1065                1070

Glu Glu Lys Val Lys Arg Gln Leu Thr Leu Ala Glu Arg Ile Arg Ala
        1075                1080                1085

Val Asp Gln His Tyr Val Ala Glu Thr Ile Leu Asn Ser His Leu Ile
    1090                1095                1100

Pro Asp Leu Arg Gly Asn Leu Arg Ser Phe Thr Arg Gln Glu Phe Arg
1105                1110                1115                1120

Cys Val Lys Cys Asn Thr Lys Tyr Arg Arg Pro Pro Leu Asp Gly Lys
                1125                1130                1135

Cys Pro Val Cys Gly Gly Lys Ile Val Leu Thr Val Ser Lys Gly Ala
            1140                1145                1150

Ile Glu Lys Tyr Leu Gly Thr Ala Lys Met Leu Val Ala Asn Tyr Asn
        1155                1160                1165

Val Lys Pro Tyr Thr Arg Gln Arg Ile Cys Leu Thr Glu Lys Asp Ile
    1170                1175                1180

Asp Ser Leu Phe Glu Tyr Leu Phe Pro Glu Ala Gln Leu Thr Leu Ile
1185                1190                1195                1200

Val Asp Pro Asn Asp Ile Cys Met Lys Met Ile Lys Glu Arg Thr Gly
                1205                1210                1215

Glu Thr Val Gln Gly Gly Leu Leu Glu Asn Phe Asn Ser Ser Gly Asn
            1220                1225                1230

Asn Gly Lys Lys Ile Glu Lys Lys Glu Lys Ala Lys Glu Lys Pro
        1235                1240                1245

Lys Lys Lys Val Ile Ser Leu Asp Asp Phe Ser Lys Arg
    1250                1255                1260

<210> SEQ ID NO 7
<211> LENGTH: 20
<212> TYPE: PRT
<213> ORGANISM: Pyrococcus furiosus

<400> SEQUENCE: 7

Met Asp Lys Glu Gly Phe Leu Asn Lys Val Arg Glu Ala Val Asp Val
 1               5                  10                  15

Val Lys Leu His
            20

<210> SEQ ID NO 8
<211> LENGTH: 20
```

-continued

```
<212> TYPE: PRT
<213> ORGANISM: Pyrococcus furiosus

<400> SEQUENCE: 8

Met Phe Thr Gly Lys Val Leu Ile Pro Val Lys Val Leu Lys Lys Phe
 1               5                  10                  15

Glu Asn Trp Asn
            20

<210> SEQ ID NO 9
<211> LENGTH: 20
<212> TYPE: PRT
<213> ORGANISM: Pyrococcus furiosus

<400> SEQUENCE: 9

Met Ile Gly Ser Ile Phe Tyr Ser Lys Lys Phe Asn Leu His Arg Pro
 1               5                  10                  15

Ser Glu Tyr His
            20

<210> SEQ ID NO 10
<211> LENGTH: 20
<212> TYPE: PRT
<213> ORGANISM: Pyrococcus furiosus

<400> SEQUENCE: 10

Met Lys Asp Tyr Arg Pro Leu Leu Gly Ala Ile Lys Val Lys Gly Asp
 1               5                  10                  15

Asn Val Phe Ser
            20

<210> SEQ ID NO 11
<211> LENGTH: 18
<212> TYPE: PRT
<213> ORGANISM: Pyrococcus furiosus

<400> SEQUENCE: 11

Met Asp Ile Glu Val Leu Arg Arg Leu Leu Glu Arg Glu Leu Ser Ser
 1               5                  10                  15

Glu His

<210> SEQ ID NO 12
<211> LENGTH: 17
<212> TYPE: PRT
<213> ORGANISM: Pyrococcus furiosus

<400> SEQUENCE: 12

Pro Phe Glu Ile Val Phe Glu Gly Ala Lys Glu Phe Ala Gln Leu Ile
 1               5                  10                  15

Asp

<210> SEQ ID NO 13
<211> LENGTH: 17
<212> TYPE: DNA
<213> ORGANISM: Artificial Sequence
<220> FEATURE:
<223> OTHER INFORMATION: N at position 15 is A, G, C, T/U, Unknown, or
      Other.
<223> OTHER INFORMATION: Description of Artificial Sequence: synthetic
      DNA

<400> SEQUENCE: 13
atggataarg arggntt                                                  17
```

-continued

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: synthetic
      DNA
<223> OTHER INFORMATION: N at position 18 is A, G, C, T/U, Unknown, or
      Other.

<400> SEQUENCE: 14
aataaagtwa grgargcngt                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 15
ctctgcggca attcttgcaa                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 16
cttgcaaaga agtatgtaac                                               20

<210> SEQ ID NO 17
<211> LENGTH: 2009
<212> TYPE: DNA
<213> ORGANISM: Pyrococcus furiosus
<220> FEATURE:
<223> OTHER INFORMATION: N at positions 1757, 1766, 1777, 1791, 1820,
      and 1823 is A, G, C, T/U, Unknown, or Other.

<400> SEQUENCE: 17
aagcttccaa agaactggcg ttacgaccca gagactgcaa agttgctcgt ccgctgatcc     60
ttccctatat tttcatttgg tgtttttcat ggataaggag ggttttttga acaaggttag    120
ggaggctgtg gatgtagtaa agctccacat cgagttaggt catactataa ggataatctc    180
tcatagggat gcggatggaa taacctctgc ggcaattctt gcaaaggctt tgggaagaga    240
aggagcgagc tttcacattt cgattgttaa acaggtaagt gaagatcttt taagagaatt    300
aaaggatgaa gattacaaaa tcttcatttt ttccgacctg ggtagtggtt ctttaagttt    360
gataaaagag tatcttaagg aaaaaactgt tataatcctt gatcaccatc ctccggaaaa    420
tgtgaagttg gaagaaaagc atatacttgt taatccagtt caatttggcg caaatagcgt    480
tagggatctg agtggatctg gggttacata cttctttgca agggagctaa atgaaaagaa    540
tagggaccttt gcttacattg caatagtggg agcagttggg gatatgcaag agaacgatgg    600
agttttccat gggatgaacc ttgatattat tgaagatggg aaatctctgg gaattcttga    660
ggttaaaaaa gaattgcgcc tgtttggtag ggaaactaga cctctctatc aaatgctcgc    720
atatgccaca aatccggaaa ttcctgaagt tactggagac gagaggaagg ccatagagtg    780

-continued

```
gttaaagaac aagggcttca atcccgagaa aaaatattgg gaattaagtg aggaggaaaa      840
gaaaaagtta catgatttcc taatcattca catgatcaag catggagctg aaaagagga      900
tatagatagg ctaataggag acgttgttat tagtccctta tatcctgaag gggatcccag      960
gcacgaggct agagaatttg ctaccctatt aaacgctaca ggcaggttaa acttgggcaa     1020
cttaggagtg gctgtatgtt tgggagatga ggaggctttc agaaaggccc taaagatggt     1080
tgaagactac aagagggagc aaattgaagc aagaaagtgg ctacttcaaa attggaacag     1140
tgaagtttgg gaggggatc atgtttacgt cttatatgtg gaaagagta ttagagatac       1200
tctcgttgga atagcagcta gcatggccat caatgctgga ctggcagatc ctgaaaagcc     1260
ggttatagtg tttgcagata ctgatgaaga tccaaacctt ctcaaaggtt cagctagaac     1320
aactgaaagg gctttagcta agggttacaa tttgggagaa gctcttagga aagcggctga     1380
gctagtgaat ggggaagggg gaggacacgc gatagctgca ggtataagaa ttcccagggc     1440
caggttggcg gagtttagaa aattaataga taaaatcctt ggagaacagg tgagcaaagg     1500
tggagataaa agcgaaagct gaaatattgt gggagtacag cgatgagaag gttgctgagg     1560
ctattgcgaa gtctgttgat gttgataata tttctctccc tccaaacctc aagaaaagtt     1620
taaatcttat gacgttttcc gatggagcga aggtaataac aaaggttaaa tatcatggag     1680
aaattgagac tctcatagtt gctctcgatg atttgatatt cgctgtaaaa gttgctgagg     1740
aggtgttatg atggtgngaa aagggnaaca acaacanggg ataagggaag ntgaagcaat     1800
ggtatattat ttatgctccn ganttcttgg gcggggtaga gtaggatta acgccagcag      1860
acgatccaga gaaagtactc aacagagtcg ttgaagttac tctgaaggat gttacaggag     1920
actttacaaa gagtcacgtg aagctctatt ccaagtata tgatgtcaag ggacagaatg      1980
cctacacaaa gttcaaggga atgaagctt                                        2009
```

<210> SEQ ID NO 18
<211> LENGTH: 1434
<212> TYPE: DNA
<213> ORGANISM: Pyrococcus furiosus

<400> SEQUENCE: 18

```
atggataagg agggttttt gaacaaggtt agggaggctg tggatgtagt aaagctccac       60
atcgagttag gtcatactat aaggataatc tctcatagggg atgcggatgg aataacctct      120
gcggcaattc ttgcaaaggc tttgggaaga gaaggagcga gctttcacat ttcgattgtt      180
aaacaggtaa gtgaagatct tttaagagaa ttaaggatg aagattacaa atcttcatt        240
ttttccgacc tgggtagtgg ttctttaagt ttgataaaag agtatcttaa ggaaaaaact      300
gttataatcc ttgatcacca tcctccggaa aatgtgaagt tggaagaaaa gcatatactt      360
gttaatccag tcaatttgg cgcaaatagc gttagggatc tgagtggatc tggggttaca      420
tacttctttg caagggagct aaatgaaaag aataggggacc ttgcttacat tgcaatagtg     480
ggagcagttg gggatatgca agagaacgat ggagttttcc atgggatgaa ccttgatatt     540
attgaagatg ggaaatctct gggaattctt gaggttaaaa aagaattgcg cctgtttggt     600
agggaaacta gacctctcta tcaaatgctc gcatatgcca caaatccgga aattcctgaa     660
gttactggag acgagaggaa ggccatagag tggttaaaga caagggctt caatcccgag     720
aaaaaatatt gggaattaag tgaggaggaa agaaaaagt tacatgatt cctaatcatt      780
cacatgatca agcatggagc tgaaaagag gatatagata ggctaatagg agacgttgtt      840
attagtccct tatatcctga aggggatcc aggcacgagg ctagagaatt tgctacccta      900
```

-continued

```
ttaaacgcta caggcaggtt aaacttgggc aacttaggag tggctgtatg tttgggagat    960
gaggaggctt tcagaaaggc cctaaagatg gttgaagact acaagaggga gcaaattgaa   1020
gcaagaaagt ggctacttca aaattggaac agtgaagttt ggagggggga tcatgtttac   1080
gtcttatatg tgggaaagag tattagagat actctcgttg aatagcagc tagcatggcc   1140 atcaatgctg gactggcaga tcctgaaaag ccggttatag tgtttgcaga tactgatgaa   1200
gatccaaacc ttctcaaagg ttcagctaga caactgaaa gggctttagc taagggttac   1260
aatttgggag aagctcttag gaaagcggct gagctagtga tggggaagg gggaggacac   1320 gcgatagctg caggtataag aattcccagg gccaggttgg cggagtttag aaaattaata   1380
gataaaatcc ttggagaaca ggtgagcaaa ggtggagata aaagcgaaag ctga         1434
```

<210> SEQ ID NO 19
<211> LENGTH: 477
<212> TYPE: PRT
<213> ORGANISM: Pyrococcus furiosus

<400> SEQUENCE: 19

```
Met Asp Lys Glu Gly Phe Leu Asn Lys Val Arg Glu Ala Val Asp Val
 1               5                  10                  15

Val Lys Leu His Ile Glu Leu Gly His Thr Ile Arg Ile Ile Ser His
            20                  25                  30

Arg Asp Ala Asp Gly Ile Thr Ser Ala Ala Ile Leu Ala Lys Ala Leu
        35                  40                  45

Gly Arg Glu Gly Ala Ser Phe His Ile Ser Ile Val Lys Gln Val Ser
    50                  55                  60

Glu Asp Leu Leu Arg Glu Leu Lys Asp Glu Asp Tyr Lys Ile Phe Ile
65                  70                  75                  80

Phe Ser Asp Leu Gly Ser Gly Ser Leu Ser Leu Ile Lys Glu Tyr Leu
                85                  90                  95

Lys Glu Lys Thr Val Ile Ile Leu Asp His His Pro Pro Glu Asn Val
            100                 105                 110

Lys Leu Glu Glu Lys His Ile Leu Val Asn Pro Val Gln Phe Gly Ala
        115                 120                 125

Asn Ser Val Arg Asp Leu Ser Gly Ser Gly Val Thr Tyr Phe Phe Ala
    130                 135                 140

Arg Glu Leu Asn Glu Lys Asn Arg Asp Leu Ala Tyr Ile Ala Ile Val
145                 150                 155                 160

Gly Ala Val Gly Asp Met Gln Glu Asn Asp Gly Val Phe His Gly Met
                165                 170                 175

Asn Leu Asp Ile Ile Glu Asp Gly Lys Ser Leu Gly Ile Leu Glu Val
            180                 185                 190

Lys Lys Glu Leu Arg Leu Phe Gly Arg Glu Thr Arg Pro Leu Tyr Gln
        195                 200                 205

Met Leu Ala Tyr Ala Thr Asn Pro Glu Ile Pro Glu Val Thr Gly Asp
    210                 215                 220

Glu Arg Lys Ala Ile Glu Trp Leu Lys Asn Lys Gly Phe Asn Pro Glu
225                 230                 235                 240

Lys Lys Tyr Trp Glu Leu Ser Glu Glu Lys Lys Leu His Asp
                245                 250                 255

Phe Leu Ile Ile His Met Ile Lys His Gly Ala Gly Lys Glu Asp Ile
            260                 265                 270

Asp Arg Leu Ile Gly Asp Val Val Ile Ser Pro Leu Tyr Pro Glu Gly
```

-continued

```
              275                 280                 285
Asp Pro Arg His Glu Ala Arg Glu Phe Ala Thr Leu Leu Asn Ala Thr
290                 295                 300
Gly Arg Leu Asn Leu Gly Asn Leu Gly Val Ala Val Cys Leu Gly Asp
305                 310                 315                 320
Glu Glu Ala Phe Arg Lys Ala Leu Lys Met Val Glu Asp Tyr Lys Arg
            325                 330                 335
Glu Gln Ile Glu Ala Arg Lys Trp Leu Leu Gln Asn Trp Asn Ser Glu
            340                 345                 350
Val Trp Glu Gly Asp His Val Tyr Val Leu Tyr Val Gly Lys Ser Ile
            355                 360                 365
Arg Asp Thr Leu Val Gly Ile Ala Ala Ser Met Ala Ile Asn Ala Gly
370                 375                 380
Leu Ala Asp Pro Glu Lys Pro Val Ile Val Phe Ala Asp Thr Asp Glu
385                 390                 395                 400
Asp Pro Asn Leu Leu Lys Gly Ser Ala Arg Thr Thr Glu Arg Ala Leu
            405                 410                 415
Ala Lys Gly Tyr Asn Leu Gly Glu Ala Leu Arg Lys Ala Ala Glu Leu
            420                 425                 430
Val Asn Gly Glu Gly Gly His Ala Ile Ala Ala Gly Ile Arg Ile
            435                 440                 445
Pro Arg Ala Arg Leu Ala Glu Phe Arg Lys Leu Ile Asp Lys Ile Leu
450                 455                 460
Gly Glu Gln Val Ser Lys Gly Gly Asp Lys Ser Glu Ser
465                 470                 475
```

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic DNA

<400> SEQUENCE: 20
ttcatttggt gttttccatg gataaggagg g          31

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic DNA
<223> OTHER INFORMATION: N at position 18 is A, G, C, T/U, Unknown, or Other.

<400> SEQUENCE: 21
aaagtwytaa twccwgtnaa rgt          23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic DNA

<400> SEQUENCE: 22
aaagtwytaa aaaarttyga raa          23

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 23
gatactgcta aagattgga                                         20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 24
ttcgtacagt ccctctggta                                        20

<210> SEQ ID NO 25
<211> LENGTH: 957
<212> TYPE: DNA
<213> ORGANISM: Pyrococcus furiosus

<400> SEQUENCE: 25
ctacgaagct aaaatttgat gtctcaactc aaggactttt agcttataaa atgtgtcaag    60
tcttccccga actttctcct ccagtaaggg ttttgtacct ctcagcaaag acaggagtag   120
gatttgaaga ccttgaaact ttagcgtatg aacattattg tacatgcggc gacctcactt   180
agatttttta acccctattt tctctaatgt cattcaagta ttgggggagt aatcatgttc   240
acgggtaagg tattgattcc agtaaaagta ctcaagaagt tgagaattg gaatgaagga    300
gatatgatac tgctagaaga ttggaaagcc aaggaattgt gggagagtgg agtagttgaa   360
ataatcgatg aagctgataa agtcatagga gagatcgata gagtgttatc agaagaaaag   420
aaaaacctcc cattgactcc aataccagag ggactgtacg aaaaagctga attttacatc   480
tattatctag aaaagtacat ccaagagaag gtcgacaaca tagaaacaat acaaactaag   540
gtcacaaagt tagcaaatct aagaagaag tataagactc tgaaagagat aagatttaaa    600
aagatactag aggctgtgag gcttagacca aacagtatgg aaattctagc gagattatcc   660
ccagctgaaa agagaatata ccttgagatc tctaaaataa ggagagagtg gataggtgat   720
tagcgtggac agggaggaga tgattgagag atttgcaaac ttccttaggg agtatacaga   780
cgaagatggt aacccagtat acagaggtaa ataactgat ttacttacaa taacacccaa    840
gaggtctgtt gcaatagact ggatgcacct aaattccttt gactcagagc tagagtcgac   900
ctgcaggcat gcatgcaggt cgactctaga ggatccccgg gtaccgagct cgaattc     957

<210> SEQ ID NO 26
<211> LENGTH: 489
<212> TYPE: DNA
<213> ORGANISM: Pyrococcus furiosus

<400> SEQUENCE: 26
atgttcacgg gtaaggtatt gattccagta aaagtactca agaagtttga gaattggaat    60
gaaggagata tgatactgct agaagattgg aaagccaagg aattgtggga gagtggagta   120
gttgaaataa tcgatgaagc tgataaagtc ataggagaga tcgatagagt gttatcagaa   180

-continued

```
gaaaagaaaa acctcccatt gactccaata ccagagggac tgtacgaaaa agctgaattt      240
tacatctatt atctagaaaa gtacatccaa gagaaggtcg acaacataga aacaatacaa      300
actaaggtca caaagttagc aaatctaaag aagaagtata agactctgaa agagataaga      360
tttaaaaaga tactagaggc tgtgaggctt agaccaaaca gtatggaaat tctagcgaga      420
ttatccccag ctgaaaagag aatataccct tgagatctcta aaataaggag agagtggata      480
ggtgattag                                                              489
```

<210> SEQ ID NO 27
<211> LENGTH: 162
<212> TYPE: PRT
<213> ORGANISM: Pyrococcus furiosus

<400> SEQUENCE: 27

```
Met Phe Thr Gly Lys Val Leu Ile Pro Val Lys Val Leu Lys Lys Phe
  1               5                  10                  15

Glu Asn Trp Asn Glu Gly Asp Met Ile Leu Leu Glu Asp Trp Lys Ala
             20                  25                  30

Lys Glu Leu Trp Glu Ser Gly Val Val Glu Ile Ile Asp Glu Ala Asp
         35                  40                  45

Lys Val Ile Gly Glu Ile Asp Arg Val Leu Ser Glu Lys Lys Asn
     50                  55                  60

Leu Pro Leu Thr Pro Ile Pro Glu Gly Leu Tyr Glu Lys Ala Glu Phe
 65                  70                  75                  80

Tyr Ile Tyr Tyr Leu Glu Lys Tyr Ile Gln Glu Lys Val Asp Asn Ile
                 85                  90                  95

Glu Thr Ile Gln Thr Lys Val Thr Lys Leu Ala Asn Leu Lys Lys Lys
            100                 105                 110

Tyr Lys Thr Leu Lys Glu Ile Arg Phe Lys Lys Ile Leu Glu Ala Val
        115                 120                 125

Arg Leu Arg Pro Asn Ser Met Glu Ile Leu Ala Arg Leu Ser Pro Ala
    130                 135                 140

Glu Lys Arg Ile Tyr Leu Glu Ile Ser Lys Ile Arg Arg Glu Trp Ile
145                 150                 155                 160

Gly Asp
```

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28

```
atgaaagayt ayagrcc                                                      17
```

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA
<223> OTHER INFORMATION: N at position 15 is A, G, C, T/U, Unknown, or
      Other.

<400> SEQUENCE: 29

-continued caagcwatwa argtnaaggg                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
ttcaagtaag agtgagttag                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
taagtactcc accatttccc                                              20

<210> SEQ ID NO 32
<211> LENGTH: 1012
<212> TYPE: DNA
<213> ORGANISM: Pyrococcus furiosus

<400> SEQUENCE: 32
tctagaacat agcagtaaaa ctttccttct agtacaactt cttctcctct gtaaactttc    60
acatcaacta tcttctttct cccttgatcc tccaccacct gagcttttgc taaaagcacg   120
tctccaactt tcaccggctt tgtaaagcgt acctctgcct ttccaagaac tacagtaggc   180
tcatttacag caagcattgc ggcgtaatca gctaaaccaa atgtaaagcc cccgtgaact   240
agccccttct catcaacctt catctcgtca atggttttca gttccacttc agcataccccc  300 tctcttatta ccctgggttt tcctacaagt ctctcagatg tcagattgtg cgttttctgc   360
tccataccac caccgaaaag aataaggttt ttgaaattta aaagctaagg gaggagtgat   420
gaaagactat aggccactcc tccaagcaat aaaagttaag ggagataatg ttttttcaag   480
taagagtgag ttagttggta ttctagcctt taatttggga atattaacag ttggtgaggc   540
aaaagaactc atagaggagg ccataaagga gggaatcatt gaggaaactc ccgaaggtct   600
catagttcat gaggatgcca taactgaaaa ggaaagcaaa agggatatat tcggggaaat   660
ggtggagtac ttagcgagag aacttgagct tagcgagata gaagttcttg aagagataga   720
aaaaatgaaa gagaggtacg gaaatttgga taaaaaaatt cttgcttact tattcggact   780
atcaaaagga gttaacatgg agaaattcaa agaatacttg gaggatgaat gatgcccaaa   840
atagaacctt ttgaaaagta cactgagaga tacgaggagt ggtttgaaag aataaatttg   900
catacctcag tgagcttaat gccctgaaat ctcttcttcc taccagagaa tgtgttgaag   960
tgggaatagg tagtggaagg tttgcggctc ccctgggaat taagatgggg gt           1012

<210> SEQ ID NO 33
<211> LENGTH: 414
<212> TYPE: DNA
<213> ORGANISM: Pyrococcus furiosus

<400> SEQUENCE: 33
atgaaagact ataggccact cctccaagca ataaaagtta agggagataa tgttttttca    60

```
agtaagagtg agttagttgg tattctagcc tttaatttgg gaatattaac agttggtgag    120
gcaaaagaac tcatagagga ggccataaag gagggaatca ttgaggaaac tcccgaaggt    180
ctcatagttc atgaggatgc cataactgaa aaggaaagca aaagggatat attcggggaa    240
atggtggagt acttagcgag agaacttgag cttagcgaga tagaagttct tgaagagata    300
gaaaaaatga agagaggta cggaaatttg gataaaaaaa ttcttgctta cttattcgga    360
ctatcaaaag gagttaacat ggagaaattc aaagaatact tggaggatga atga          414
```

```
<210> SEQ ID NO 34
<211> LENGTH: 137
<212> TYPE: PRT
<213> ORGANISM: Pyrococcus furiosus

<400> SEQUENCE: 34
```

Met Lys Asp Tyr Arg Pro Leu Leu Gln Ala Ile Lys Val Lys Gly Asp
 1               5                  10                  15

Asn Val Phe Ser Ser Lys Ser Glu Leu Val Gly Ile Leu Ala Phe Asn
                20                  25                  30

Leu Gly Ile Leu Thr Val Gly Glu Ala Lys Glu Leu Ile Glu Glu Ala
            35                  40                  45

Ile Lys Glu Gly Ile Ile Glu Glu Thr Pro Glu Gly Leu Ile Val His
        50                  55                  60

Glu Asp Ala Ile Thr Glu Lys Glu Ser Lys Arg Asp Ile Phe Gly Glu
 65                  70                  75                  80

Met Val Glu Tyr Leu Ala Arg Glu Leu Glu Leu Ser Glu Ile Glu Val
                85                  90                  95

Leu Glu Glu Ile Glu Lys Met Lys Glu Arg Tyr Gly Asn Leu Asp Lys
               100                 105                 110

Lys Ile Leu Ala Tyr Leu Phe Gly Leu Ser Lys Gly Val Asn Met Glu
           115                 120                 125

Lys Phe Lys Glu Tyr Leu Glu Asp Glu
       130                 135

```
<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
aaagctaagg gaggacatat gaaagactat agg                                  33

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
tcaaaccact cctcgaattc ctcagtgtac ttttc                                35

<210> SEQ ID NO 37
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 37
ccwttygara twgtwttyga                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA
<223> OTHER INFORMATION: N as position 18 is A, G, C, T/U, Unknown or
      Other.

<400> SEQUENCE: 38
ggwgcwaarg arttygcnca                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
aacttataga caccgcaagt                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
gtcactcttc aactcttgga                                              20

<210> SEQ ID NO 41
<211> LENGTH: 989
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
aagcttataa aagaataccc gatacagaca atggaaaaac ttatttattg agggtaaag      60 aaagagttag gcttatgcta aacattctta aggaggtgga aagagatgcc atttgaaatc    120
gtatttgaag gtgcaaaaga gtttgcccaa cttatagaca ccgcaagtaa gttaatagat    180
gaggccgcgt ttaaagttac agaagatggg ataagcatga gggccatgga tccaagtaga    240
gttgtcctga ttgacctaaa tctcccgtca agcatattta gcaaatatga agttgttgaa    300
ccagaaacaa ttggagttaa catggaccac ctaaagaaga tcctaaagag aggtaaagca    360
aaggacacct taatactcaa gaaggagag gaaaacttct tagagataac aattcaagga    420
actgcaacaa gaacatttag agttccccta atagatgtag aagagatgga agttgacctc    480
ccagaacttc cattcactgc aaaggttgta gttcttggag aagtcctaaa agatgctgtt    540
aaagatgcct ctctagtgag tgacagcata aaatttattg ccaggaaaaa tgaattata     600
```

```
atgaaggcag agggagaaac ccaggaagtt gagataaagc taactcttga agatgaggga      660
ttattggaca tcgaggttca agaggagaca aagagcgcat atggagtcag ctatctctcc      720
gacatggtta aaggacttgg aaaggccgat gaagttacaa taaagtttgg aaatgaaatg      780
cccatgcaaa tggagtatta cattagagat gaaggaagac ttacattcct actggctcca      840
agagttgaag agtgactttt cttttcctta taatttaatt tggggataac aatggatatt      900
gaggttctca gaagattatt ggagagagaa ctttcaagcg aagaactgac taaaatagag      960 gaagaattt atgacgattt agaaagctt                                         989

<210> SEQ ID NO 42
<211> LENGTH: 45
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
ccggaaccgc ctccctcaga gccgccaccc tcagaaccgc caccc                      45

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
ccwtgggtwg araartayag rcc                                              23

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA
<223> OTHER INFORMATION: N at position 15 is A, G, C, T/U, Unknown, or
      Other.

<400> SEQUENCE: 44
wswgatgaaa gaggnathga                                                  20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA
<223> OTHER INFORMATION: N at position 15 is A, G, C, T/U, Unknown, or
      Other.

<400> SEQUENCE: 45
gcwttwagaa gaacnatgga                                                  20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA
```

<223> OTHER INFORMATION: N at position 18 is A, G, C, T/U, Unknown, or
      Other.

<400> SEQUENCE: 46
ttwccwacwc cwggwggncc                                         20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA
<223> OTHER INFORMATION: N at position 18 is A, G, C, T/U, Unknown, or
      Other.

<400> SEQUENCE: 47
cttcttaawg cattytgngc                                         20

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 48
atwattttws wwggatartt rca                                     23

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA
<223> OTHER INFORMATION: N at position 18 is A, G, C, T/U, Unknown, or
      Other.

<400> SEQUENCE: 49
atwgcttttc tcatrtcncc                                         20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 50
atcttgagtt aaagcgtcgg                                         20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 51
acgttcgctt tatcttgagc                                         20

<210> SEQ ID NO 52
<211> LENGTH: 20

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 52
tcaaagactt gacgacattg                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 53
ttctgctatg taaagtattg                                              20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 54
caatacttta catagcagaa                                              20

<210> SEQ ID NO 55
<211> LENGTH: 3620
<212> TYPE: DNA
<213> ORGANISM: Pyrococcus furiosus
<220> FEATURE:
<223> OTHER INFORMATION: N at positions 3121, 3222, 3233, 3289, and 3296
      is A, G, C, T/U, Unknown, or Other.

<400> SEQUENCE: 55
gagctccagc aacaacaata acccaagatg gaaaggactt tggagtaagg tactttggat    60
taccggcagg tcatgagttc gcagcattct tagaggacat tgtggatgtt agtagagaag   120
aaacaaacct tatggacgag acaaaacagg ccatcagaaa catagaccag gatgtaagaa   180
tattggtgtt tgaaactcca acatgcccat actgtccact tgccgttaga atggctcaca   240
agtttgccat tgaaaacaca aaagctggga aggtaagat acttggggat atggtcgagg    300
ccattgagta tccagagtgg gctgaccagt acaatgtaat ggcagtacca aaaattgtta   360
ttcaggtcaa cggagaagac agagtagaat ttgaaggagc ttatccagag aaaatgttct   420
tagagaagtt actctcagct ctcagctgat ctactgtttt tccttctttt cttctgttct   480
gttattgcct aggataagct taataatact ttgataccrt tcttagttta ggtgtgtgag   540
agtatgagcg aagagattag agaagttaag gttctagaaa acccctgggt tgagaagtat   600
agacctcaaa gacttgacga cattgtagga caagagcaca tagtgaaaag gctcaagcac   660
tacgtcaaaa ctggatcaat gccccaccta ctcttcgcag gccccctgg tgtcggaaag    720 tgtcttactg gagataccaa agttatagct aatggccaac tctttgaact tggagaactt   780
gttgaaaagc tttctggggg gagatttgga ccaactccag ttaagggct caaagttctt    840 ggaatagatg aggatggaaa gcttagagag tttgaagtcc aatacgtcta caagatagatag   900 actgataggt tgataaagat aaaaactcac cttggcaggg agcttaaagt aactccgtat   960
```

-continued

```
cacccacttc tagtgaatag agagaatggc gaaataaagt ggattaaggc tgaagaactc    1020
aaacctggcg acaagcttgc aataccgagc tttctcccac ttataactgg agaaaatccc    1080
cttgcagagt ggcttggtta ctttatggga agtggctatg cttatccaag taattctgtc    1140
atcacgttca ctaacgaaga tccactcata agacaacgct ttatggaact aacagagaaa    1200
cttttccctg atgcaaagat aagggaaaga attcacgctg atggaactcc agaagtttat    1260
gtggtatcta ggaaagcttg gagccttgta aactctatta gcttaacatt aatacccagg    1320
gagggtggaa aaggaattcg ttctttcctt agggcatatt ccgactgcaa tggtcggatt    1380
gaaagtgatg caatagtttt atcaaccgat aacaatgata tggcccagca gatagcctat    1440
gctttagcca gctttggaat aatagctaaa atggatggag aagatgttat tatctcaggc    1500
tcggacaaca tagagaggtt cctaaatgag attggcttta gcacccaaag caaacttaaa    1560
gaagcccaga agctcattag aaaaaccaat gtaagatccg atggactaaa gattaactat    1620
gagctaatct cctatgtaaa agacaggctt aggttaaatg tcaatgataa agaaatttg    1680 agctacagaa atgcaaagga gctttcttgg gaactcatga agaaattta ttatcgcctt    1740 gaggaactgg agagactaaa gaaggtctta tcagaaccca tcttgatcga ctggaatgaa    1800
gtagcaaaga gagtgatga agtaatagaa aaagctaaaa ttagagcaga gaagctccta    1860
gaatacataa aaggagagag aaagccaagt ttcaaggagt acattgagat agcaaaagtc    1920
cttggaatta acgttgaacg taccatcgaa gctatgaaga tctttgcaaa gagatactca    1980
agctatgccg agattggaag aaaacttgga acttggaatt tcaatgtaaa aacaattctt    2040
gagagcgaca cagtggataa cgttgaaatc cttgaaaaga taaggaaaat tgagcttgag    2100
ctcatagagg aaattctttc ggatggaaag ctcaaagaag gtatagcata tctcattttc    2160
ctcttccaga atgagcttta ctgggacgag ataactgaag taaaagagct taggggagac    2220
tttataatct atgatcttca tgttcctggc taccacaact ttattgctgg gaacatgcca    2280
acagtagtcc ataacactac agcggctttg gcccttgcaa gagagctttt cggcgaaaac    2340
tggaggcata acttcctcga gttgaatgct tcagatgaaa gaggtataaa cgtaattaga    2400
gagaaagtta aggagtttgc gagaacaaag cctataggag gagcaagctt caagataatt    2460
ttccttgatg aggccgacgc tttaactcaa gatgcccaac aagccttaag aagaaccatg    2520
gaaatgttct cgagtaacgt tcgctttatc ttgagctgta actactcctc caagataatt    2580
gaacccatac agtctagatg tgcaatattc cgcttcagac ctctccgcga tgaggatata    2640
gcgaagagac taaggtacat tgccgaaaat gagggcttag agctaactga agaaggtctc    2700
caagcaatac tttacatagc agaaggagat atgagaagag caataaacat tctgcaagct    2760
gcagcagctc tagacaagaa gatcaccgac gaaaacgtat tcatggtagc gagtagagct    2820
agacctgaag atataagaga gatgatgctt cttgctctca aaggcaactt cttgaaggcc    2880
agagaaaagc ttagggagat acttctcaag caaggactta gtggagaaga tgtactagtt    2940
cagatgcaca aagaagtctt caacctgcca atagaggagc caagaaggt tctgcttgct    3000 gataagatag gagagtataa cttcagactc gttgaagggg ctaatgaaat aattcagctt    3060
gaagcactct tagcacagtt cacccctaatt gggaagaagt gatgaagtat gccagagctt    3120
nccttgggta gaaaaataca ggccaaaaaa gctaagtgaa attgtaaacc aagaagaggc    3180
tatagagaaa gttagagcgt ggatagagag ctggttgcat gnccacccc ttnagaaaaa    3240 agccgtatta ttagcaggac ccccagggag cggaaagaca accacagtnt acgctntagc    3300
aaatgagtac aactttgaag tcattgagct caacgcgagt gatgagagaa cttatgaaaa    3360
```

```
aatctccagg tatgttcaag cagcatacac tatggatatc ctcggaaaga ggaggaagat    3420
aatcttcctc gatgaagcag ataatataga gcccagcgga gctaaggaaa tcgcaaaact    3480
aattgataag gccaaaaatc caataataat ggctgcaaat aagtactggg aagttccaaa    3540
agagatccga gaaaaagctg agctagtaga gtacaagagg ttaacccaga gagatgtaat    3600
gaatgcctta ataaggatcc                                                3620
```

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 56

```
ctttccgaca ccagggggc c                                                  21
```

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 57

```
actacagcgg ctttggccct t                                                 21
```

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 58

```
gatgagttcg tgtccgtaca act                                                23
```

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 59

```
acaaagccag ccggaatatc tg                                                 22
```

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA
<223> OTHER INFORMATION: N at position 18 is A, G, C, T/U, Unknown, or
      Other.

<400> SEQUENCE: 60

```
gcttctaaat cattdatngc                                                    20
```

```
<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
gcgtggatag agagctggtt                                                    20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 62
ctctgggtta acctcttgta                                                    20

<210> SEQ ID NO 63
<211> LENGTH: 1437
<212> TYPE: DNA
<213> ORGANISM: Pyrococcus furiosus

<400> SEQUENCE: 63
atgccagagc ttccctgggt agaaaaatac aggccaaaaa agttaagtga aattgtaaac         60
caagaagagg ctatagagaa agttagagcg tggatagaga gctggttgca tggccacccc       120
cctaagaaaa aagcccctatt attagcagga ccccaggga gcggaaagac aaccacagtc       180
tacgctctag caaatgagta caactttgaa gtcattgagc tcaacgcgag tgatgagaga       240
acttatgaaa aaatctccag gtatgttcaa gcagcataca ctatggatat cctcggaaag       300
aggaggaaga taatcttcct cgatgaagca gataatatag agcccagcgg agctaaggaa       360
atcgcaaaac taattgataa ggccaaaaat ccaataataa tggctgcaaa taagtactgg       420
gaagttccaa aagagatccg agaaaagct gagctagtag agtacaagag gttaacccag       480
agagatgtaa tgaatgcctt aataaggatc ctaaagaggg aaggtataac agttccaaaa       540
gaaatcctcc tagaaatagc aaaaagatct agtggagatc taagagcagc tataaatgat       600
ctacagaccg ttgtagtggg tggttacgaa gatgctacgc aagttttggc atatagagat       660
gtagaaaaga cagtctttca agccctagga ctcgtctttg gaagtgacaa cgccaagagg       720
gcaaagatgg caatgtggaa cttggacatg tcccctgatg aattcctgct atgggtagat       780
gagaacattc ctcacctcta cctaaatcca gaggagattg cccaggcgta tgatgcaatt       840
agtagagccg acatatacct cggaagggcc gccagaactg gaaactattc actctggaag       900
tacgcaatag atatgatgac tgcaggagtt gccgtggcag ggagaaagag aagggattt       960 gtcaagtttt atcctcccaa caccctaaag atttagcgg aaagcaaaga agaaagagag     1020
atcagagagt caataattaa aaagataata cgagagatgc acatgagtag gctacaggca     1080
atagaaacga tgaaaataat tagagagatt ttcgagaaca atctagacct tgctgcgcac     1140
tttacagtgt tccttggtct gtctgaaaaa gaagttgagt ttctagctgg aaaggaaaaa     1200
gctggtacca tttggggcaa agccttagca ttaagaagga aacttaagga gcttggaata     1260
agagaggagg agaagcctaa agttgaaatt gaagaagagg aagaagagga agaaaagacc     1320
gaagaagaaa aagaggaaat agaagaaaaa cccgaagaag agaagaagga ggagaagaaa     1380
```

-continued gaaaaggaaa agccaaagaa aggcaaacaa gcaactctct ttgactttct taaaaag    1437

<210> SEQ ID NO 64
<211> LENGTH: 479
<212> TYPE: PRT
<213> ORGANISM: Pyrococcus furiosus

<400> SEQUENCE: 64

| | | | | | | | | | | | | | | |
|---|---|---|---|---|---|---|---|---|---|---|---|---|---|---|
| Met | Pro | Glu | Leu | Pro | Trp | Val | Glu | Lys | Tyr | Arg | Pro | Lys | Lys | Leu | Ser |
| 1 | | | | 5 | | | | | 10 | | | | | 15 | |
| Glu | Ile | Val | Asn | Gln | Glu | Glu | Ala | Ile | Glu | Lys | Val | Arg | Ala | Trp | Ile |
| | | | 20 | | | | | 25 | | | | | 30 | | |
| Glu | Ser | Trp | Leu | His | Gly | His | Pro | Lys | Lys | Ala | Leu | Leu | Leu | | |
| | | 35 | | | | | 40 | | | | | 45 | | | |
| Ala | Gly | Pro | Pro | Gly | Ser | Gly | Lys | Thr | Thr | Val | Tyr | Ala | Leu | Ala | |
| | 50 | | | | | 55 | | | | | 60 | | | | |
| Asn | Glu | Tyr | Asn | Phe | Glu | Val | Ile | Glu | Leu | Asn | Ala | Ser | Asp | Glu | Arg |
| 65 | | | | | 70 | | | | | 75 | | | | | 80 |
| Thr | Tyr | Glu | Lys | Ile | Ser | Arg | Tyr | Val | Gln | Ala | Ala | Tyr | Thr | Met | Asp |
| | | | | 85 | | | | | 90 | | | | | 95 | |
| Ile | Leu | Gly | Lys | Arg | Arg | Lys | Ile | Ile | Phe | Leu | Asp | Glu | Ala | Asp | Asn |
| | | | 100 | | | | | 105 | | | | | 110 | | |
| Ile | Glu | Pro | Ser | Gly | Ala | Lys | Glu | Ile | Ala | Lys | Leu | Ile | Asp | Lys | Ala |
| | | | 115 | | | | | 120 | | | | | 125 | | |
| Lys | Asn | Pro | Ile | Ile | Met | Ala | Ala | Asn | Lys | Tyr | Trp | Glu | Val | Pro | Lys |
| | | 130 | | | | | 135 | | | | | 140 | | | |
| Glu | Ile | Arg | Glu | Lys | Ala | Glu | Leu | Val | Glu | Tyr | Lys | Arg | Leu | Thr | Gln |
| 145 | | | | | 150 | | | | | 155 | | | | | 160 |
| Arg | Asp | Val | Met | Asn | Ala | Leu | Ile | Arg | Ile | Leu | Lys | Arg | Glu | Gly | Ile |
| | | | | 165 | | | | | 170 | | | | | 175 | |
| Thr | Val | Pro | Lys | Glu | Ile | Leu | Leu | Glu | Ile | Ala | Lys | Arg | Ser | Ser | Gly |
| | | | 180 | | | | | 185 | | | | | 190 | | |
| Asp | Leu | Arg | Ala | Ala | Ile | Asn | Asp | Leu | Gln | Thr | Val | Val | Gly | Gly | |
| | | 195 | | | | | 200 | | | | | 205 | | | |
| Tyr | Glu | Asp | Ala | Thr | Gln | Val | Leu | Ala | Tyr | Arg | Asp | Val | Glu | Lys | Thr |
| | 210 | | | | | 215 | | | | | 220 | | | | |
| Val | Phe | Gln | Ala | Leu | Gly | Leu | Val | Phe | Gly | Ser | Asp | Asn | Ala | Lys | Arg |
| 225 | | | | | 230 | | | | | 235 | | | | | 240 |
| Ala | Lys | Met | Ala | Met | Trp | Asn | Leu | Asp | Met | Ser | Pro | Asp | Glu | Phe | Leu |
| | | | | 245 | | | | | 250 | | | | | 255 | |
| Leu | Trp | Val | Asp | Glu | Asn | Ile | Pro | His | Leu | Tyr | Leu | Asn | Pro | Glu | Glu |
| | | | 260 | | | | | 265 | | | | | 270 | | |
| Ile | Ala | Gln | Ala | Tyr | Asp | Ala | Ile | Ser | Arg | Ala | Asp | Ile | Tyr | Leu | Gly |
| | | 275 | | | | | 280 | | | | | 285 | | | |
| Arg | Ala | Ala | Arg | Thr | Gly | Asn | Tyr | Ser | Leu | Trp | Lys | Tyr | Ala | Ile | Asp |
| | 290 | | | | | 295 | | | | | 300 | | | | |
| Met | Met | Thr | Ala | Gly | Val | Ala | Val | Ala | Gly | Arg | Lys | Arg | Gly | Phe | |
| 305 | | | | | 310 | | | | | 315 | | | | | 320 |
| Val | Lys | Phe | Tyr | Pro | Pro | Asn | Thr | Leu | Lys | Ile | Leu | Ala | Glu | Ser | Lys |
| | | | | 325 | | | | | 330 | | | | | 335 | |
| Glu | Glu | Arg | Glu | Ile | Arg | Glu | Ser | Ile | Ile | Lys | Lys | Ile | Ile | Arg | Glu |
| | | | 340 | | | | | 345 | | | | | 350 | | |
| Met | His | Met | Ser | Arg | Leu | Gln | Ala | Ile | Glu | Thr | Met | Lys | Ile | Ile | Arg |
| | | 355 | | | | | 360 | | | | | 365 | | | |

```
Glu Ile Phe Glu Asn Asn Leu Asp Leu Ala Ala His Phe Thr Val Phe
        370                 375                 380

Leu Gly Leu Ser Glu Lys Glu Val Glu Phe Leu Ala Gly Lys Glu Lys
385                 390                 395                 400

Ala Gly Thr Ile Trp Gly Lys Ala Leu Ala Leu Arg Arg Lys Leu Lys
                    405                 410                 415

Glu Leu Gly Ile Arg Glu Glu Glu Lys Pro Lys Val Glu Ile Glu Glu
                420                 425                 430

Glu Glu Glu Glu Glu Glu Lys Thr Glu Glu Lys Glu Glu Ile Glu
                435                 440                 445

Glu Lys Pro Glu Glu Lys Glu Glu Glu Lys Lys Glu Lys Glu Lys
        450                 455                 460

Pro Lys Lys Gly Lys Gln Ala Thr Leu Phe Asp Phe Leu Lys Lys
465                 470                 475
```

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic DNA
<223> OTHER INFORMATION: N at position 18 is A, G, C, T/U, Unknown, or Other.

<400> SEQUENCE: 65
atggatatwg argtdytnag rag                                        23

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 66
atwgargtwy twagragryt                                            20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 67
gagagagaac tttcaagcga                                            20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 68
ctctaagaag atatgcctct                                            20

<210> SEQ ID NO 69
<211> LENGTH: 558
<212> TYPE: DNA

<213> ORGANISM: Pyrococcus furiosus

<400> SEQUENCE: 69

| atggatattg | aggttctcag | aagattattg | gagagagaac | tttcaagcga | agaactgact | 60 |
| aaaatagagg | aagaatttta | tgacgattta | gaaagcttta | gaaaagcctt | ggaaatcaat | 120 |
| gccgagagac | atgaagaaag | aggagaggac | attcacaaaa | agctgtattt | agctcaacta | 180 |
| tctttggtta | ggaatcttgt | tagagaaata | ttaaggatta | ggttgcataa | gattgttgat | 240 |
| atggcatttg | agggagttcc | cagaaattta | gttggagatg | aaaagaaaat | atacaagata | 300 |
| ataacagctt | tcataaatgg | agaacctctt | gaaattgaaa | cggcaggaga | agagagtatt | 360 |
| gaagttattg | aagaggaaaa | agaaacatct | cctgggataa | tagaggcata | tcttcttaga | 420 |
| gttgatattc | ccaaaatatt | ggatgaaaat | ttgagagaat | atgggccctt | caaggctggc | 480 |
| gatcttgttg | tattgccgaa | gtctattggc | agggtactca | ttcagaggga | tgccgcggat | 540 |
| aaggtattga | tacaattg |  |  |  |  | 558 |

<210> SEQ ID NO 70
<211> LENGTH: 186
<212> TYPE: PRT
<213> ORGANISM: Pyrococcus furiosus

<400> SEQUENCE: 70

Met Asp Ile Glu Val Leu Arg Arg Leu Leu Glu Arg Glu Leu Ser Ser
1               5                   10                  15

Glu Glu Leu Thr Lys Ile Glu Glu Phe Tyr Asp Asp Leu Glu Ser
            20                  25                  30

Phe Arg Lys Ala Leu Glu Ile Asn Ala Glu Arg His Glu Glu Arg Gly
        35                  40                  45

Glu Asp Ile His Lys Lys Leu Tyr Leu Ala Gln Leu Ser Leu Val Arg
    50                  55                  60

Asn Leu Val Arg Glu Ile Leu Arg Ile Arg Leu His Lys Ile Val Asp
65                  70                  75                  80

Met Ala Phe Glu Gly Val Pro Arg Asn Leu Val Gly Asp Glu Lys Lys
                85                  90                  95

Ile Tyr Lys Ile Ile Thr Ala Phe Ile Asn Gly Glu Pro Leu Glu Ile
            100                 105                 110

Glu Thr Ala Gly Glu Glu Ser Ile Glu Val Ile Glu Glu Lys Glu
        115                 120                 125

Thr Ser Pro Gly Ile Ile Glu Ala Tyr Leu Leu Arg Val Asp Ile Pro
    130                 135                 140

Lys Ile Leu Asp Glu Asn Leu Arg Glu Tyr Gly Pro Phe Lys Ala Gly
145                 150                 155                 160

Asp Leu Val Val Leu Pro Lys Ser Ile Gly Arg Val Leu Ile Gln Arg
                165                 170                 175

Asp Ala Ala Asp Lys Val Leu Ile Gln Leu
            180                 185

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: Synthetic DNA

<400> SEQUENCE: 71

-continued tttaatttgg ggataaccat ggatattgag gtt                33

<210> SEQ ID NO 72
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72
taggatgggt tttggatcct ctcattggag g                   31

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 73
atgatwggww swathttyta                                20

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 74
aagaagttta atytdcayag rcc                            23

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 75
tgagtatcat ccagagaatc                                20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 76
tcacatcggg atcgttccag                                20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 77
gattttgacg ctcatcatgg                                20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 78
ggaaagaacg atttcgagtc                                              20

<210> SEQ ID NO 79
<211> LENGTH: 1005
<212> TYPE: DNA
<213> ORGANISM: Pyrococcus furiosus

<400> SEQUENCE: 79

```
atgattggct caatatttta ttccaagaag tttaacctcc atagacctag tgagtatcat      60
ccagagaatc ccaagagact cgaaatcgtt ctttccaagg tcagagagct tggacttgaa     120
gaaagaatag aagaaccaaa cccagttgaa gagactttcg ttgagaaaat tcacgacagg     180
gattacatca acttcgttaa agaggccgtt gaaaaaggaa tcacaagact tgatccagac     240
acttatgttt ctcctgggac ttggagtgcg gcattgttag ctttaggagc cgcaaggagt     300
gcagctttat cagcccttca ctatggaggc ctccacatgg ctctagttag gccccctggg     360
catcatgcag ggagaagagg aagggccatg ggtgcccaa cactaggctt ctgcatcttc      420
aacaacgcgg cctctgcagt tgtcaccttg aaagaagagg gagttggaaa agttgttgta     480
atagattttg acgctcatca tggaaacggg actcaggaaa tattctggaa cgatcccgat     540
gtgattcaca tagatctaca cgagagagac atctacccag ggagtgggga tgtgagtgaa     600
gttggagggt caaatgctta tgggagcaag ataaacctcc caatgcccca ctattctggg     660
gatggggatt acatatatgt ttgggacgaa attgtgcttc aatagttga agaagttaag      720
ccaaaggtca tcgtaatttc cgcgggcttt gatggattta aggggatgg tctaacaaca      780
ttaaggctca cagaaagttt ttactcttat gcaggggcta cattaaataa atatcccttg     840
gcatttatat tggaaggcgg gtatggagta gggttagata aagttttcc ggccttcata      900
atgggctacg aagagggtaa agcgaaagct cgagaagagc caagatatga gaccctaaag     960
ttggcggagg aggttaagga catcttgagt ccctggtggt cgtta                    1005
```

<210> SEQ ID NO 80
<211> LENGTH: 335
<212> TYPE: PRT
<213> ORGANISM: Pyrococcus furiosus

<400> SEQUENCE: 80

```
Met Ile Gly Ser Ile Phe Tyr Ser Lys Lys Phe Asn Leu His Arg Pro
 1               5                  10                  15

Ser Glu Tyr His Pro Glu Asn Pro Lys Arg Leu Glu Ile Val Leu Ser
                20                  25                  30

Lys Val Arg Glu Leu Gly Leu Glu Glu Arg Ile Glu Glu Pro Asn Pro
            35                  40                  45

Val Glu Glu Thr Phe Val Glu Lys Ile His Asp Arg Asp Tyr Ile Asn
        50                  55                  60

Phe Val Lys Glu Ala Val Glu Lys Gly Ile Thr Arg Leu Asp Pro Asp
 65                  70                  75                  80
```

-continued

```
Thr Tyr Val Ser Pro Gly Thr Trp Ser Ala Leu Leu Ala Leu Gly
             85                  90                  95

Ala Ala Arg Ser Ala Ala Leu Ser Ala Leu His Tyr Gly Gly Leu His
            100                 105                 110

Met Ala Leu Val Arg Pro Pro Gly His His Ala Gly Arg Arg Gly Arg
            115                 120                 125

Ala Met Gly Ala Pro Thr Leu Gly Phe Cys Ile Phe Asn Asn Ala Ala
            130                 135                 140

Ser Ala Val Val Thr Leu Lys Glu Gly Val Gly Lys Val Val
145                 150                 155                 160

Ile Asp Phe Asp Ala His His Gly Asn Gly Thr Gln Glu Ile Phe Trp
                165                 170                 175

Asn Asp Pro Asp Val Ile His Ile Asp Leu His Glu Arg Asp Ile Tyr
            180                 185                 190

Pro Gly Ser Gly Asp Val Ser Glu Val Gly Gly Ser Asn Ala Tyr Gly
            195                 200                 205

Ser Lys Ile Asn Leu Pro Met Pro His Tyr Ser Gly Asp Gly Asp Tyr
210                 215                 220

Ile Tyr Val Trp Asp Glu Ile Val Leu Pro Ile Val Glu Glu Val Lys
225                 230                 235                 240

Pro Lys Val Ile Val Ile Ser Ala Gly Phe Asp Gly Phe Lys Gly Asp
                245                 250                 255

Gly Leu Thr Thr Leu Arg Leu Thr Glu Ser Phe Tyr Ser Tyr Ala Gly
            260                 265                 270

Ala Thr Leu Asn Lys Tyr Pro Leu Ala Phe Ile Leu Glu Gly Gly Tyr
            275                 280                 285

Gly Val Gly Leu Asp Lys Gly Phe Pro Ala Phe Ile Met Gly Tyr Glu
            290                 295                 300

Glu Gly Lys Ala Lys Ala Arg Glu Glu Pro Arg Tyr Glu Thr Leu Lys
305                 310                 315                 320

Leu Ala Glu Glu Val Lys Asp Ile Leu Ser Pro Trp Trp Ser Leu
                325                 330                 335

<210> SEQ ID NO 81
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 81
gggaagaagt gatgacatat gccagagctt ccctgg                               36

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 82
ttccaagctc cttaagtttc                                                 20

<210> SEQ ID NO 83
<211> LENGTH: 3574
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 83
catatgccag agcttccctg ggtagaaaaa tacaggccaa aaaagttaag tgaaattgta      60
aaccaagaag aggctataga gaaagttaga gcgtggatag agagctggtt gcatggccac     120
ccccctaaga aaaagccct attattagca ggaccccag ggagcggaaa gacaaccaca       180
gtctacgctc tagcaaatga gtacaacttt gaagtcattg agctcaacgc gagtgatgag     240
agaacttatg aaaaaatctc caggtatgtt caagcagcat acactatgga tatcctcgga     300
aagaggagga agataatctt cctcgatgaa gcagataata tagagcccag cggagctaag     360
gaaatcgcaa aactaattga taaggccaaa aatccaataa taatggctgc aaataagtac     420
tgggaagttc caaagagat ccgagaaaaa gctgagctag tagagtacaa gaggttaacc      480
cagagagatg taatgaatgc cttaataagg atcctaaaga gggaaggtat aacagttcca     540
aaagaaatcc tcctagaaat agcaaaaaga tctagtggag atctaagagc agctataaat     600
gatctacaga ccgttgtagt gggtggttac gaagatgcta cgcaagtttt ggcatataga     660
gatgtagaaa agacagtctt tcaagcccta ggactcgtct ttggaagtga caacgccaag     720
agggcaaaga tggcaatgtg gaacttggac atgtcccctg atgaattcct gctatgggta     780
gatgagaaca ttcctcacct ctacctaaat ccagaggaga ttgcccaggc gtatgatgca     840
attagtagag ccgacatata cctcggaagg gccgccagaa ctggaaacta ttcactctgg     900
aagtacgcaa tagatatgat gactgcagga gttgccgtgg cagggagaaa gagaaggga      960
tttgtcaagt tttatcctcc caacacccta agattttag cggaaagcaa agaagaaga     1020
gagatcagag agtcaataat taaaagata atacgagaga tgcacatgag taggctacag    1080
gcaatagaaa cgatgaaaat aattagagag atttctgaga caatctaga ccttgctgcg    1140
cactttacag tgttccttgg tctgtctgaa aagaagttg agtttctagc tggaaaggaa    1200
aaagctggta ccatttgggg caaagcctta gcattaagaa ggaaacttaa ggagcttgga   1260
ataagagagg aggagaagcc taaagttgaa attgaagaag aggaagaaga ggaagaaaag   1320
accgaagaag aaaagagga aatagaagaa aaacccgaag aagagaaaga gaggagaag     1380
aaagaaaagg aaaagccaaa gaaaggcaaa caagcaactc tctttgactt tcttaaaaag   1440
tgattaccct tttcttcta ttagagctcc gaataaagtt ggccctctaa ttttttctat    1500
tgtctcctcc acattaatct ttacgaattc gagctccagc aacaacaata cccaagatg    1560
gaaaggactt tggagtaagg tactttggat taccggcagg tcatgagttc gcagcattct   1620
tagaggacat tgtggatgtt agtagagaag aaacaaacct tatggacgag acaaaacagg   1680
ccatcagaaa catagaccag gatgtaagaa tattggtgtt tgaaactcca acatgcccat   1740
actgtccact tgccgttaga atggctcaca agtttgccat tgaaaacaca aaagctggga   1800
aaggtaagat acttggggat atggtcgagg ccattgagta tccagagtgg gctgaccagt   1860
acaatgtaat ggcagtacca aaaattgtta ttcaggtcaa cggagaagac agagtagaat   1920
ttgaaggagc ttatccagag aaaatgttct tagagaagtt actctcagct ctcagctgat   1980
ctactgtttt tccttctttt cttctgttct gttattgcct aggataagct taataatact   2040
ttgatacctt tcttagttta ggtgtgtgag agtatgagcg aagagattag agaagttaag   2100
gttctagaaa aaccctgggt tgagaagtat agacctcaaa gacttgacga cattgtagga   2160
caagagcaca tagtgaaaag gctcaagcac tacgtcaaaa ctggatcaat gccccaccta   2220
```

```
ctcttcgcag gccccctgg tgtcggaaag actacagcgg ctttggccct tgcaagagag      2280
cttttcggcg aaaactggag gcataacttc ctcgagttga atgcttcaga tgaaagaggt      2340
ataaacgtaa ttagagagaa agttaaggag tttgcgagaa caaagcctat aggaggagca      2400
agcttcaaga taattttcct tgatgaggcc gacgctttaa ctcaagatgc ccaacaagcc      2460
ttaagaagaa ccatggaaat gttctcgagt aacgttcgct ttatcttgag ctgtaactac      2520
tcctccaaga taattgaacc catacagtct agatgtgcaa tattccgctt cagacctctc      2580
cgcgatgagg atatagcgaa gagactaagg tacattgccg aaaatgaggg cttagagcta      2640
actgaagaag gtctccaagc aatactttac atagcagaag gagatatgag aagagcaata      2700
aacattctgc aagctgcagc agctctagac aagaagatca ccgacgaaaa cgtattcatg      2760
gtagcgagta gagctagacc tgaagatata agagagatga tgcttcttgc tctcaaaggc      2820
aacttcttga aggccagaga aaagcttagg gagatacttc tcaagcaagg acttagtgga      2880
gaagatgtac tagttcagat gcacaaagaa gtcttcaacc tgccaataga ggagccaaag      2940
aaggttctgc ttgctgataa gataggagag tataacttca gactcgttga aggggctaat      3000
gaaataattc agcttgaagc actcttagca cagttcaccc taattgggaa gaagtgatga      3060
agtatgccag agcttccctg ggtagaaaaa tacaggccaa aaaagttaag tgaaattgta      3120
aaccaagaag aggctataga gaaagttaga gcgtggatag agagctggtt gcatggccac      3180
ccccctaaga aaaagccgt attattagca ggacccccag ggagcggaaa gacaaccaca      3240
gtctacgctc tagcaaatga gtacaacttt gaagtcattg agctcaacgc gagtgatgag      3300
agaacttatg aaaaaatctc caggtatgtt caagcagcat acactatgga tatcctcgga      3360
aagaggagga agataatctt cctcgatgaa gcagataata tagagcccag cggagctaag      3420
gaaatcgcaa aactaattga taaggccaaa aatccaataa taatggctgc aaataagtac      3480
tgggaagttc caaaagagat ccgagaaaaa gctgagctag tagagtacaa gaggttaacc      3540
cagagagatg taatgaatgc cttaataagg atcc                                 3574
```

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 84
tacttgtaat attctcatat gattggctca ata                                  33

<210> SEQ ID NO 85
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 85
gatgagttcg tgtccgtaca actggcgtaa tcatg                                35

<210> SEQ ID NO 86
<211> LENGTH: 25
<212> TYPE: DNA
<213> ORGANISM: Artificial Sequence
<220> FEATURE:

<223> OTHER INFORMATION: Description of Artificial Sequence: Synthetic
      DNA

<400> SEQUENCE: 86
ggttatcgaa atcagccaca gcgcc                                              25

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 87
gcgtaccttt gtctcacggg caa                                                23

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 88
gatagctgtc gtcataggac tc                                                 22

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 89
cttaaccagt gcgctgagtg act                                                23

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 90
gacaatctgg aatacgccac ctgacttg                                           28

<210> SEQ ID NO 91
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 91
ttgccacttc cgtcaaccag gcttatca                                           28

<210> SEQ ID NO 92
<211> LENGTH: 29
<212> TYPE: DNA
<213> ORGANISM: Artificial Sequence
<220> FEATURE:

```
<223> OTHER INFORMATION: Description of Artificial Sequence: Synthetic
      DNA

<400> SEQUENCE: 92
tgtccgtcag ctcataacgg tacttcacg                                    29
```

DNA POLYMERASE-RELATED FACTORS

This application is a continuation of application Ser. No. 09/446,504, filed on Dec. 23, 1999 now U.S. Pat. No. 6,218,150. Application Ser. No. 09/446,504 is the national phase of PCT International Application No. PCT/JP98/02845 filed on Jun. 24, 1998 under 35 U.S.C. §371 and designating the United States of America. The entire contents of each of the above-identified applications are hereby incorporated by reference.

This application also incorporates by reference a Sequence Listing of 92 sequences on 47 pages.

TECHNICAL FIELD

The present invention relates a DNA polymerase-associated factor. More specifically, the present invention relates to a DNA polymerase-associated factor which is useful for a reagent for genetic engineering and a method for producing the same, and further a gene encoding thereof, and the like.

BACKGROUND ART

DNA polymerases are useful enzymes for reagents for genetic engineering, and the DNA polymerases are widely used for nucleotide sequencing of DNA, DNA labeling, site-directed mutagenesis, and the like. Also, thermostable DNA polymerases have recently been remarked with the development of the polymerase chain reaction (PCR) method, and various DNA polymerases suitable for the PCR method have been developed and commercialized.

Presently known DNA polymerases can be roughly classified into four families according to amino acid sequence homologies, among which family A (pol I type enzymes) and family B (α type enzymes) account for the great majority. Although DNA polymerases belonging to each family generally possess mutually similar biochemical properties, detailed comparison reveals that individual enzymes differ from each other in terms of substrate specificity, incorporation efficiency of a substrate analog, primer extensibility and extension rate, mode of DNA synthesis, association of exonuclease activity, optimum reaction conditions of temperature, pH and the like, and sensitivity to inhibitors. Therefore, those possessing most appropriate properties for the applications have been selected among all available DNA polymerases, and the selected DNA polymerase has been used.

A hyperthermophilic archaebacterium *Pyrococcus furiosus* has produced a DNA polymerase belonging to α type, and its gene has already been isolated [*Nucleic Acids Research*, 21, 259–265 (1993)].

As DNA polymerases, in addition to ones expressing their functions with only one kind of an enzyme protein, such as the pol I type enzyme or the α type enzyme, there have been known oligomer enzymes constituted by a large number of subunit proteins. In addition to the protein serving as a DNA polymerase, there have also been known some cases where protein molecules for regulating their functions coexist.

DISCLOSURE OF INVENTION

An object of the present invention is to provide a thermostable DNA polymerase-associated factor capable of enhancing DNA synthesizing-activity of a DNA polymerase, and a thermostable DNA polymerase-associated factor possessing an activity of binding to a DNA polymerase.

Another object of the present invention is to provide a gene for the DNA polymerase-associated factor of the present invention.

Still another object of the present invention is to provide a method for producing the DNA polymerase-associated factor of the present invention.

Still another object of the present invention is to provide a method of DNA synthesis by using a DNA polymerase in the presence of the DNA polymerase-associated factor of the present invention.

Still another object of the present invention is to provide a kit comprising the DNA polymerase-associated factor of the present invention.

According to the present invention, there can be provided in vitro DNA synthesis and a DNA amplification system which are more excellent than conventional techniques by utilizing the DNA polymerase-associated factor of the present invention.

Recently, a novel DNA polymerase having completely no structural homology to conventionally known DNA polymerases has been found by the present inventors from hyperthermophilic archaebacterium *Pyrococcus furiosus* (WO 97/24444 Pamphlet). In this DNA polymerase, two kinds of novel proteins form a complex and exhibit a DNA polymerase activity. In addition, the enzyme exhibits a potent 3'→5' exonuclease activity and excellent primer extension activity. For example, when the enzyme is used for PCR, a DNA fragment of the size of about 20 kb can be amplified. In this novel DNA polymerase derived from *Pyrococcus furiosus*, although at least two kinds of proteins are essential constituents in the enzyme activity, it has not been elucidated whether or not a constituent protein of the enzyme beside the above exists, or whether or not a factor having an influence on the activity of the enzyme exists.

As a result of intensive studies, the present inventors have succeeded in isolating a protein binding to the novel DNA polymerase derived from *Pyrococcus furiosus*. Further, they have found that the production of the protein by genetic engineering is made possible by cloning the gene, and moreover that a DNA synthesizing-activity of a DNA polymerase is enhanced.

In sum, the present invention relates to:

[1] a thermostable DNA polymerase-associated factor capable of enhancing DNA synthesizing-activity of a DNA polymerase;

[2] the DNA polymerase-associated factor according to item [1] above, further possessing an activity of binding to a DNA polymerase;

[3] the DNA polymerase-associated factor according to item [2] above, which possesses an activity of binding to a DNA polymerase comprising a DNA polymerase-constituting protein having the amino acid sequence as shown in SEQ ID NO: 5 or 6 in Sequence Listing;

[4] the DNA polymerase-associated factor according to any one of items [1] to [3] above, comprising at least one of amino acid sequences selected from the group consisting of SEQ ID NOs: 1, 3, 19, 27, 34, 64, 70 and 80 in Sequence Listing, or an amino acid sequence resulting from substitution, deletion, addition or insertion of one or more amino acids in at least one of the amino acid sequences;

[5] a gene encoding a DNA polymerase-associated factor, wherein the factor comprises at least one of amino acid sequences selected from the group consisting of SEQ ID NOs: 1, 3, 19, 27, 34, 64, 70 and 80 in Sequence Listing, or an amino acid sequence resulting from substitution, deletion, addition or insertion of one or more amino acids in at least one of amino acid sequences, and possesses an activity of enhancing DNA synthesizing-activity of a DNA polymerase;

[6] the gene according to item [5] above, comprising a nucleotide sequence selected from the group consisting of SEQ ID NOs: 2, 4, 18, 26, 33, 63, 69 and 79, or a nucleotide sequence resulting from substitution, deletion, addition or insertion of one or more bases in the nucleotide sequence;

[7] a gene capable of hybridizing to the gene of item [5] or [6] above, and encoding a DNA polymerase-associated factor possessing an activity of enhancing DNA synthesizing-activity of a DNA polymerase;

[8] a method for producing a DNA polymerase-associated factor, characterized in that the method comprises culturing a transformant harboring the gene of any one of items [5] to [7] above, and collecting a thermostable DNA polymerase-associated factor capable of enhancing DNA synthesizing-activity of a DNA polymerase from the cultured medium;

[9] a method of DNA synthesis by using a DNA polymerase, characterized in that DNA is synthesized in the presence of the DNA polymerase-associated factor of any one of items [1] to [4] above;

[10] the method of DNA synthesis according to item [9] above, wherein DNA is synthesized in the presence of two or more kinds of DNA polymerase-associated factors;

[11] the method of DNA synthesis according to item [10] above, wherein DNA is synthesized in the presence of F7, PFU-RFC and PFU-RFCLS as a DNA polymerase-associated factor;

[12] the method of DNA synthesis according to any one of items [9] to [11] above, wherein the DNA polymerase is a thermostable DNA polymerase;

[13] the method of DNA synthesis according to item [12] above, wherein the synthesis is carried out by PCR method;

[14] a kit usable for in vitro DNA synthesis, comprising the DNA polymerase-associated factor of any one of items [1] to [4] above and a DNA polymerase;

[15] the kit according to item [14] above, further comprising a reagent required for DNA synthesis;

[16] the kit according to item [14] or [15] above, comprising two or more kinds of DNA polymerase-associated factors;

[17] the kit according to item [16] above, comprising F7, PFU-RFC and PFU-RFCLS as a DNA polymerase-associated factor; and

[18] the kit according to any one of items [14] to [17] above, comprising a thermostable DNA polymerase as a DNA polymerase.

BRIEF DESCRIPTION OF DRAWINGS

FIG. 14 shows analytical results of SDS-PAGE of 3 kinds of proteins (PFU-RFCLS, PFU-RFC, F7) isolated by an anti-PFU-RFC antibody column.

BEST MODE FOR CARRYING OUT THE INVENTION

Figure 1:
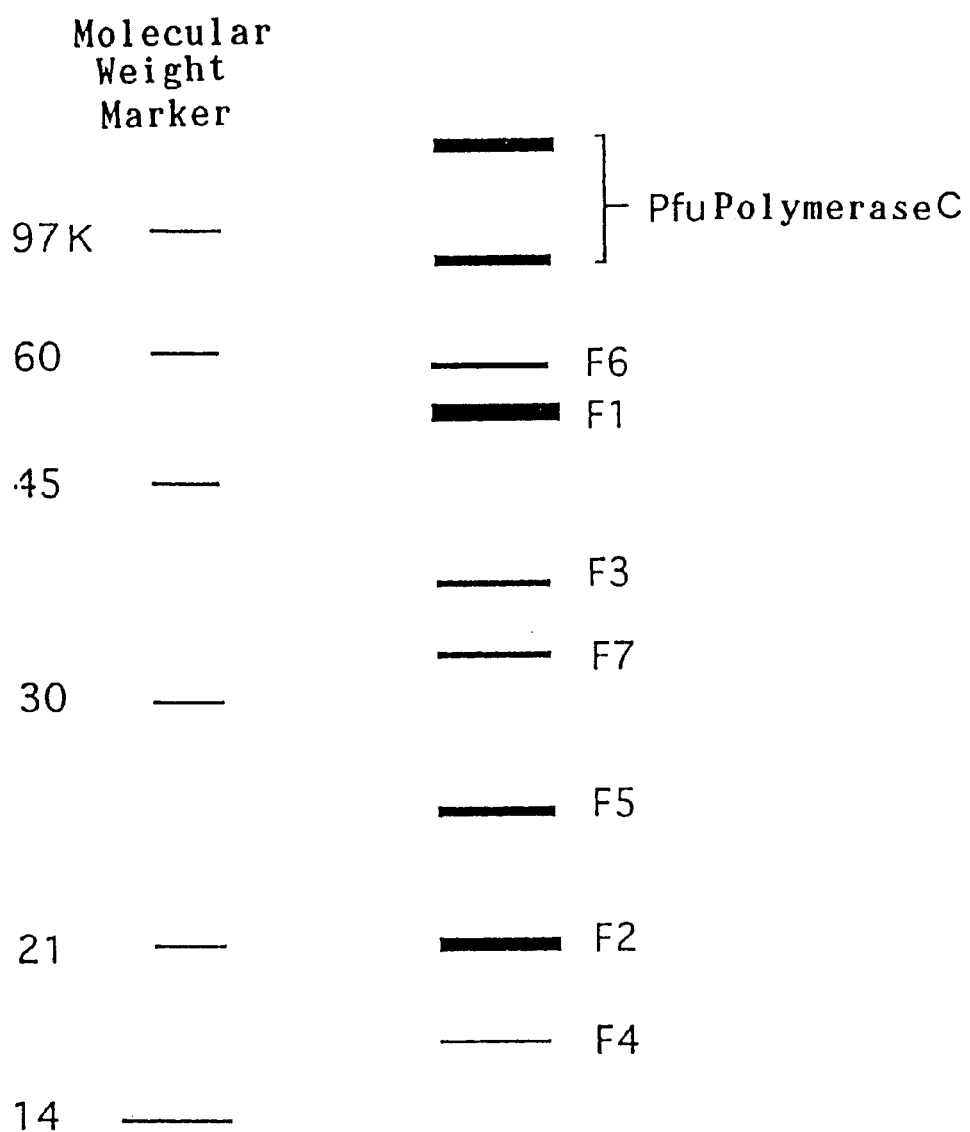
FIG. 1 is a drawing showing SDS-PAGE of 7 kinds of proteins (F1, F2, F3, F4, F5, F6 and F7) isolated by an anti-Pfu polymerase C antibody column. The molecular weights on SDS-PAGE are about 55 kDa, about 24 kDa, about 37 kDa, about 19.5 kDa, about 27 kDa, about 64 kDa and about 33 kDa, in a sequential order of F1 to F7.

1. DNA Polymerase-Associated Factor of the Present Invention

In the present specification, the term "EDNA polymerase-associated factor" means a factor which has effects on a function of a DNA polymerase by coexisting with the DNA polymerase. Concretely, the DNA polymerase-associated factors include a factor possessing an action of enhancing the DNA synthesizing-activity of a DNA polymerase, a factor possessing an activity of binding to a DNA polymerase, and further one possessing both activities, and the like. In addition, the DNA polymerase-associated factor of the present invention is a thermostable protein, which is, for instance, stable against heat treatment at 80° C. for 15 minutes. Therefore, the factor can be used for DNA synthesizing-reaction under high-temperature conditions using a thermostable DNA polymerase.

(a) DNA Polymerase-Associated Factor Capable of Enhancing
DNA Synthesizing-Activity of DNA Polymerase The DNA polymerase-associated factor capable of enhancing DNA synthesizing-activity of a DNA polymerase is not particularly limited, as long as the factor is capable of enhancing DNA synthesizing-activity of a DNA polymerase. For instance, the factor includes proteins comprising an entire or partial sequence of amino acid sequence as shown in at least one sequence selected from the group consisting of SEQ ID NOs: 1, 3, 19, 27, 34, 64, 70 and 80 in Sequence Listing; or functional equivalents thereof comprising an amino acid sequence resulting from substitution, deletion, addition or insertion of one or more amino acids in at least one of the amino acid sequences, and the equivalent possessing an activity of enhancing DNA synthesizing-activity of a DNA polymerase. In the present specification, the term "one or more" refers to a number of one or several or more. In addition, the term "functional equivalent" refers to ones which are substantially equivalent in their functions and activities even though they are structurally different, and the functional equivalents are also encompassed in the DNA polymerase-associated factor of the present invention.

The DNA polymerase of which activity is enhanced by the DNA polymerase-associated factor of the present invention is not particularly limited. Examples thereof include thermostable DNA polymerases, in particular DNA polymerases derived from hyperthermophilic archaebacterium. Concretely, there can be cited DNA polymerases derived from *Pyrococcus furiosus* (Pfu polymerase C, and the like mentioned below). As described below, the Pfu polymerase C is an enzyme comprising a DNA polymerase-constituting protein having the amino acid sequences as shown in SEQ ID NO: 5 and SEQ ID NO: 6 in Sequence Listing.

In addition, the DNA polymerase-associated factor of the present invention may be one enhancing only an activity of a particular DNA polymerase, and it is preferably one enhancing its activities against a plural kinds of DNA polymerase from different origins.

The method for determination of an activity of enhancing DNA synthesizing-activity of a DNA polymerase is not particularly limited, as long as it is one usually employed in the determination of DNA synthesizing-activity of a DNA polymerase. The activity of enhancing DNA synthesizing-activity can be, for instance, determined by adding the factor when measuring an incorporation activity of the labeled nucleotide into a novel synthesized DNA strand; and comparing the incorporation activity with an activity when the factor is not added. In addition, there can be cited a method for confirmation from the chain length of a novel synthetic DNA strand per unit time or from the amount of PCR amplified product per unit time. As the method for determination of the DNA synthesizing-activity, there can be cited a method described in DNA Polymerase from *Escherichia coli,* published by Harpar and Row, edited by D. R. Davis, 263–276 (authored by C. C. Richardson), and the like.

Further, in the DNA polymerase-associated factor of the present invention, by a combination of a plurality of the DNA polymerase-associated factors, there can be exhibited an even higher DNA polymerase activity in the coexistent DNA polymerases when compared with that of the single use.

(b) DNA Polymerase-Associated Factor Possessing Activity of Binding to DNA Polymerase The DNA polymerase-associated factor possessing an activity of binding to a DNA polymerase is not particularly limited, as long as it possesses an activity of binding to a DNA polymerase. Incidentally, the DNA polymerase-associated factor possessing an activity of binding to a DNA polymerase in the present specification encompasses other substances, for instance, ones having an activity of indirectly binding to a DNA polymerase via other DNA polymerase-associated factors, as well as ones having an activity of directly binding to a DNA polymerase. Examples thereof include proteins comprising an entire or partial sequence of amino acid sequence as shown in at least one sequence selected-from the group consisting of SEQ ID NOs: 1, 3, 19, 27, 34, 64, 70 and 80 in Sequence Listing; or functional equivalents thereof comprising an amino acid sequence resulting from substitution, deletion, addition or insertion of one or more amino acids in at least one of the amino acid sequences, and the equivalent possessing an activity of binding to a DNA polymerase. In the present specification, the term "one or more" refers to a number of one or several or more.

The DNA polymerase binding to the DNA polymerase-associated factor of the present invention, which is not particularly limited, includes, for instance, a thermostable DNA polymerase, in particular DNA polymerases derived from hyperthermophilic archaebacterium. Concretely, there can be cited DNA polymerases derived from *Pyrococcus furiosus* (Pfu polymerase C, and the like). One or both of the DNA polymerase-constituting proteins having the amino acid sequences as shown in SEQ ID NO: 5 and SEQ ID NO: 6 in Sequence Listing are bound to Pfu polymerase C.

In addition, the DNA polymerase-associated factor of the present invention may be one binding to a particular DNA polymerase, and it is preferably one binding to a plural kinds of DNA polymerase from different origins.

The method for determination of the binding to a DNA polymerase includes a method comprising mixing the factor with a DNA polymerase, and examining a change in the molecular weight by native gel electrophoresis, gel filtration, and the like; a method for examining the adsorption of the factor to a carrier immobilized to a DNA polymerase, and the like.

In addition, the DNA polymerase-associated factor comprising the amino acid sequence as shown in SEQ ID NO: 19 in Sequence Listing possesses an exonuclease activity. Therefore, it is considered that the DNA polymerase-associated factor comprising the amino acid sequence as shown in SEQ ID NO: 19 is a protein having a function associated with the action of a DNA polymerase in DNA replication, DNA repair, and the like. Further, as the functional equivalents of the DNA polymerase-associated factor, proteins comprising a partial sequence of the amino acid sequence as shown in SEQ ID NO: 19 in Sequence Listing, or an amino acid sequence resulting from substitution, deletion, addition or insertion of one or more amino acids in at least one of the sequences, wherein the proteins possess an activity of binding to a DNA polymerase, and further similarly possess an exonuclease activity are encompassed in the present invention as the DNA polymerase-associated factor. In the present specification, the term "one or more" refers to a number of one or several or more.

Incidentally, in the explanation of the DNA polymerase-associated factor of the present invention, the factor is identified as a protein comprising an entire or partial sequence of each of the amino acid sequences as shown in particular SEQ ID NO in Sequence Listing, and the term "protein comprising" as used herein encompasses proteins as described below, which are also encompassed in the present invention. Namely, when a protein is produced by genetic engineering techniques, it is often expressed as a fusion protein. For instance, in order to increase an expression level of the desired protein, the protein is expressed by adding a N-terminal peptide chain derived from other proteins to the N-terminus, or expressed by adding an appropriate peptide chain at N-terminus or C-terminus of the desired protein, and a carrier having affinity with each of the peptide chain is used, whereby facilitating the purification of the desired protein. In the present invention, the fusion proteins mentioned above are also encompassed.

2. Genes Encoding DNA Polymerase-Associated Factor of the Present Invention (a) Properties of Genes Encoding DNA Polymerase-Associated Factor of the Present Invention The genes encoding the DNA polymerase-associated factor of the present invention are those encoding the DNA polymerase-associated factor of the present invention mentioned above, which refers to DNA or RNA. Concretely, the gene includes a gene encoding a DNA polymerase-associated factor, wherein the factor comprises an entire or partial sequence of amino acid sequence as shown in at least one sequence selected from the group consisting of SEQ ID NOs: 1, 3, 19, 27, 34, 64, 70 and 80 in Sequence Listing, or an amino acid sequence resulting from substitution, deletion, addition or insertion of one or more amino acids in at least one of these sequences, and the factor possesses an activity of enhancing DNA synthesizing-activity of a DNA polymerase, or an activity of binding to a DNA polymerase. Concrete examples of such genes include genes encoding a DNA polymerase-associated factor, comprising an entire or partial sequence of nucleotide sequence as shown in at least one sequence selected from the group consisting of SEQ ID NOs: 2, 4, 18, 26, 33, 63, 69 and 79, or a nucleotide sequence resulting from substitution, deletion, addition or insertion of one or more bases in these sequences, wherein the factor possesses an activity of enhancing DNA synthesizing-activity of a DNA polymerase, or an activity of binding to a DNA polymerase. In the present specification, the term "one or more" refers to a number of one or several or more. In the present invention, there can be further cited a gene capable of hybridizing to a DNA of the gene of the present invention, and possessing an activity of enhancing DNA synthesizing-activity, or an activity of binding to a DNA polymerase.

The term "gene capable of hybridizing (to a gene)" described in the present specification refers to a gene comprising a DNA capable of hybridizing to a DNA of a gene, which is a gene having a nucleotide sequence resembling to the gene. With regard to the gene having a nucleotide sequence resembling to a gene, there is a high possibility of having resemblance to an amino acid sequence of a protein encoded thereby, and additionally having resemblance to a function of the protein. The homology of the nucleotide sequence of the gene can be examined by whether or not a hybrid is formed (the genes being hybridized) with DNAs of both genes or a partial portion thereof under stringent conditions. By utilizing hybridization, a gene encoding a protein having similar functions to a protein encoding the gene can be obtained. In other words, the other genes of the present invention having homologous nucleotide sequences to a gene of the present invention can be obtained by carrying out hybridization by a known method using a DNA of the gene obtained in the present invention, or a partial portion thereof, as a probe. The hybridization can be carried out, for instance, by a method described in *Molecular Cloning: A Laboratory Manual,* 2nd Ed., published by Cold Spring Harbor Laboratory in 1989, edited by T. Maniatis et al., or the like.

Here, the term "the stringent conditions" refers to conditions in which non-specific hybridization does not take place. Concretely, for instance, there are the following conditions. In other words, a DNA-immobilized membrane is incubated at 50° C. for 12 to 20 hours together with a labeled DNA probe in 6×SSC (wherein 1×SSC shows 0.15 M NaCl, 0.015 M sodium citrate, pH 7.0) containing 0.5% SDS, 0.1% bovine serum albumin (BSA), 0.1% polyvinyl pyrrolidone, 0.1% Ficol 400, and 0.01% denatured salmon sperm DNA. After termination of the incubation, the membrane is washed, initiating under the conditions of 37° C. in 2×SSC containing 0.5% SDS, the SSC concentration being made variable up to a range of 0.1×SDS, and the temperature being variable up to a range of 50° C., until a signal ascribed to an immobilized labeled DNA probe can be distinguished from the background.

In addition, instead of hybridization, there can be utilized a method for gene amplification using a partial sequence of the nucleotide sequence of the gene of the present invention as a primer. For instance, PCR method can be utilized. The PCR conditions can be appropriately set by sequences of primer DNAs or a template DNA. Whether or not the gene obtained as described above encodes a protein having the desired function can be examined by confirming the activity of the resulting protein by expressing a protein encoded by the gene using an appropriate host and an expression system.

In addition, the method for artificially preparing an amino acid sequence or nucleotide sequence having substitution, deletion, addition, or insertion of one or more in the amino acid sequence or nucleotide sequence in the present invention includes various genetic engineering manipulations described in *Molecular Cloning: A Laboratory Manual,* 2nd Ed., published by Cold Spring Harbor Laboratory in 1989, edited by T. Maniatis et al., or the like. Concrete examples thereof include genetic engineering techniques such as methods for site-directed mutagenesis and cassette mutation methods. By the method for site-directed mutagenesis, an amino acid sequence or nucleotide sequence having one or more substitution, deletion, addition or insertion can be prepared. By the cassette mutation method, there can be prepared an amino acid sequence or nucleotide sequence having a larger region of deletion, addition or insertion as compared with the sequence obtained by the method for site-directed mutagenesis. These modified products described above are also encompassed in the present invention as long as they are functionally equivalent. Further, in the production of a protein by genetic engineering techniques, in a case where a codon used on a naturally occurring gene encoding the desired protein is used at a low frequency, the expression level of the protein may be low. In such a case, the codon is artificially converted to one frequently used in the host without changing the encoded amino acid sequence, whereby the desired protein is highly expressed (for instance, Japanese Examined Patent Publication No. Hei 7-102146).

(b) Cloning of Gene Encoding DNA Polymerase-Associated Factor of the Present Invention Detailed descriptions on the analysis of the resulting clones, the physicochemical properties of the expression product DNA polymerase-associated factor, the elucidation of the functions, and the like will be given hereinbelow.

As described above, the DNA polymerase-associated factor of the present invention possesses an action of enhancing DNA synthesizing-activity of a DNA polymerase, or a characteristic of binding the factor to a DNA polymerase. Therefore, the factor can be obtained by using these actions as indices.

The DNA polymerase utilizable in the obtainment of the DNA polymerase-associated factor of the present invention is not particularly limited, and an example thereof includes a *Pyrococcus furiosus*-producing DNA polymerase. As the *Pyrococcus furiosus*-producing DNA polymerase, for instance, there can be used an enzyme comprising a DNA polymerase-constituting protein comprising the amino acid sequence as shown in SEQ ID NO: 5 and/or SEQ ID NO: 6 in Sequence Listing, derived from *Pyrococcus furiosus* DSM3638.

Incidentally, in the present specification, this enzyme is described as Pfu polymerase C, in order to distinguish with α type DNA polymerase [Pfu DNA polymerase, *Nucleic Acids Research*, 21, 259–265 (1993)], which has been also found from *Pyrococcus furiosus*. The gene encoding the enzyme is carried by plasmid pFU1001. In addition, a transformant, *Escherichia coli* JM109 transformed with the plasmid, is named and identified as *Escherichia coli* JM109/ pFU1001, and deposited under the accession number of FERM BP-5579 with the National Institute of Bioscience and Human-Technology, Agency of Industrial Science and Technology, Ministry of International Trade and Industry, of which the address is 1–3, Higashi 1-chome, Tsukuba-shi, Ibaraki-ken (Zipcode 305–8566), Japan, since Aug. 11, 1995 (date of original deposit) under the Budapest Treaty. Therefore, Pfu polymerase C can be obtained by culturing the transformant and purifying from the resulting cultured medium. Incidentally, Pfu polymerase C is an enzyme comprising a DNA polymerase-constituting protein having the amino acid sequence as shown in SEQ ID NO: 5 and/or SEQ ID NO: 6 in Sequence Listing.

Pfu polymerase C is an enzyme possessing the following properties:

(A) exhibiting a higher activity when the polymerase activity is determined by using as a substrate a complex resulting from annealing of a primer to a single stranded template DNA, as compared to the case where an activated DNA is used as a substrate;

(B) possessing a 3'→5' exonuclease activity;

(C) being capable of amplifying a DNA fragment of about 20 kbp without adding other enzymes, in the case where polymerase chain reaction (PCR) is carried out with λ-DNA as a template under the following conditions: PCR conditions:

a) a composition of reaction mixture: comprising 10 mM Tris-HCl (pH 9.2), 3.5 MM MgCl$_2$, 75 mM KCl, 400 μM each of dATP, dCTP, dGTP and dTTP, 0.01% bovine serum albumin, 0.1% Triton X-100, 5.0 ng/50 μl λ-DNA, 10 pmole/50 μl primer λ1 (SEQ ID NO: 58 in Sequence Listing), primer λ11 (SEQ ID NO: 59 in Sequence Listing), and 3.7 units/50 μl DNA polymerase;

b) reaction conditions: carrying out PCR for 30 cycles, wherein one cycle is 98° C., 10 seconds—68° C., 10 minutes; and (D) comprising two kinds of DNA polymerase-constituting proteins corresponding to about 90,000 daltons and about 140,000 daltons on SDS-PAGE, respectively.

The method of obtaining the DNA polymerase-associated factor of the present invention is not particularly limited. For instance, the factor can be obtained by immobilizing a DNA polymerase, such as Pfu polymerase C, to an appropriate carrier, mixing the DNA polymerase-immobilized carrier with a sample containing the DNA polymerase-associated factor, removing the factor unbound to the carrier, and thereafter eluting the bound carrier. The immobilization of the DNA polymerase to the carrier can be carried out by a known method. Alternatively, an antibody against the DNA polymerase is prepared, and a DNA polymerase may be immobilized by utilizing the antibody-immobilized carrier. For instance, when an anti-Pfu polymerase C antibody is prepared, and the DNA polymerase-associated factor of the present invention is obtained by using the antibody from a sample derived from *Pyrococcus furiosus*, including, for instance, a cell disrupted solution of *Pyrococcus furiosus*, Pfu polymerase C in the sample binds to this antibody when the antibody-immobilized carrier as described above is used. Therefore, it is not necessary to add Pfu polymerase C aside from the sample, so that the DNA polymerase-associated factor can be readily purified.

The sample used in the obtainment of the DNA polymerase-associated factor of the present invention is not particularly limited. For instance, there can be used samples derived from microorganisms. Concretely, samples derived from *Pyrococcus furiosus* DSM 3638 can be used. The above strain can be made available from Deutsche Sammlung von Mikroorganismen und Zellkulturen GmbH. In the case of a cell disrupted solution obtained by culturing the above strain in an appropriate growth medium and preparing from the resulting cultured medium is applied to a column packed with a carrier immobilized with an anti-Pfu polymerase C antibody, several kinds of proteins other than Pfu polymerase C are adsorbed to the column. The gene encoding these proteins can be cloned by the procedures exemplified below.

First, the above proteins are isolated by a known method, and their N-terminal amino acid sequences are determined. In reference to the amino acid sequences, synthetic oligonucleotides to be used as primers or probes are prepared. Next, PCR is carried out with a genomic DNA of *Pyrococcus furiosus* as a template using this synthetic oligonucleotide as a primer, whereby a DNA fragment carrying the desired gene can be obtained. The conditions for PCR may be appropriately set. Alternatively, a DNA fragment carrying the desired gene can be obtained from a genomic DNA of *Pyrococcus furiosus* by carrying out hybridization using the above oligonucleotide as a probe. In this case, as the hybridization, there can be employed Southern hybridization using a genomic DNA of *Pyrococcus furiosus* obtained by digesting with an appropriate restriction enzyme, colony hybridization using a gene library of a genomic DNA of *Pyrococcus furiosus*, plaque hybridization, dot hybridization, and the like.

When the DNA fragment as obtained above does not carry a full length of the desired gene, new primers are prepared in reference to the nucleotide sequence of the resulting DNA fragment, and PCR is further carried out, or hybridization is carried out using the resulting DNA fragment or its partial fragment as a probe, whereby a full length of the desired gene can be obtained.

The manipulations for the PCR and hybridization are not particularly limited, and for instance, they can be carried out in reference to *Molecular Cloning: A Laboratory Manual*, 2nd Ed., published by Cold Spring Harbor Laboratory in 1989, edited by T. Maniatis et al.

When the cell disrupted solution of the strain *Pyrococcus furiosus* DSM 3638 is mixed with the above carrier immobilized with the anti-Pfu polymerase C antibody, there are seven kinds of proteins adsorbed to the carrier as well as Pfu polymerase C. With respect to six kinds among them, in the present invention, their genes have been isolated by the above described manipulations. These proteins are named F1, F2, F3, F4, F5 and F7, respectively, which are the concrete examples of the DNA polymerase-associated factor of the present invention. The nucleotide sequences of an open reading frame of the gene encoding these proteins are shown in SEQ ID NOs: 18, 26, 79, 33, 69 and 2, respectively, in Sequence Listing. In addition, the amino acid sequences of each protein deduced from these nucleotide sequences are shown in SEQ ID NOs: 19, 27, 80, 34, 70 and 1, respectively, in Sequence Listing.

The cloned gene is introduced into an appropriate host, for instance, *Escherichia coli*, whereby allowing to express a protein encoded thereby. For instance, a transformant of *Escherichia coli* JM109, into which a gene encoding F7 mentioned above is introduced, is named and identified as *Escherichia coli* JM109/pF7-HH-18, and deposited under the accession number of FERM BP-6338 with the National Institute of Bioscience and Human-Technology, Agency of Industrial Science and Technology, Ministry of International Trade and Industry, of which the address is 1–3, Higashi 1-chome, Tsukuba-shi, Ibaraki-ken (Zipcode 305–8566), Japan, since Jun. 3, 1997 (date of original deposit) under the Budapest Treaty. F7 can be obtained by culturing the transformant, and recovering a desired product from the resulting culture. It is elucidated in the present invention that the F7 as obtained above enhances activities of α type polymerase (Pfu DNA polymerase) derived from *Pyrococcus furiosus* and two kinds of DNA polymerases [*J. Bacteriol.*, 177, 2164–2177 (1995)] derived from *Pyrodictium occultum*, in addition to Pfu polymerase C used in protein isolation.

In addition, there are also elucidated that each of F1, F2, F3, F4 and F5 mentioned above enhances an activity of Pfu polymerase C and Pfu DNA polymerase.

When the amino acid sequence of the protein derived from the above strain *Pyrococcus furiosus* DSM 3638 is compared with an amino acid sequence of a known protein, F1 has homologies to a single-stranded DNA-specific exonuclease derived from *Haemophilis influenzae* [*Science*, 269, 496–512 (1995)]. F3 has homologies to *Mycoplana ramosa*-derived acetylpolyamine aminohydrase [*Journal of Bacteriology*, 178, 5781–5786 (1996)] and human histone deacetylase [*Science*, 272, 408–411 (1996)]. In addition, F7 has homologies to the proliferating cell nuclear antigen (PCNA) involved in the DNA replication in eukaryotes [*EMBO J.*, 11, 5111–5120 (1995); *Nucleic Acids Research*, 18, 261–265 (1990); *Proc. Natl. Acad. Sci. USA*, 84, 1575–1579 (1987)]. F2, F4 and F5 have not been found to have homologies to a known protein.

There has been reported that PCNA forms a complex with a replication factor C (RFC, RF-C) to be involved in DNA synthesis [*Journal of Biochemistry*, 68, 1542–1548 (1996)]. Therefore, even in *Pyrococcus furiosus*, it is expected that a protein corresponding to RFC is expressed, and that the protein is involved in DNA synthesis reaction together with F7 mentioned above. A further excellent effect of enhancing DNA polymerase synthesizing-activity can be obtained by collecting this protein, and for instance, adding the resulting protein together with F7 mentioned above in the reaction system for DNA polymerase. The gene encoding an RFC homolog of *Pyrococcus furiosus* can be obtained by the steps described below.

An entire nucleotide sequence of chromosomal DNA of archaebacteria *Methanococcus jannaschii* has been already elucidated [*Science*, 273, 1058–1073 (1996)], and the nucleotide sequences carry the gene encoding a protein which is considered to be a homolog of PCNA and RFC. The amino acid sequence encoded by the gene of a homolog of RFC small subunit and large subunit of the strain is compared with the amino acid sequence encoded by a known RFC small subunit gene [*Nucleic Acids Research*, 21, 1–3 (1993); *Nucleic Acids Research*, 22, 1527–1535 (1994)], thereby examining for the amino acid sequences of high homologies. A synthetic oligonucleotide can be prepared in reference to the above, the oligonucleotide usable as a primer or probe for obtaining a gene fragment encoding RFC small subunit and large subunit. Subsequently, by the manipulations employed for the obtainment of the gene encoding any one of F1 to F7 mentioned above using the oligonucleotide, there can be obtained, for instance, a gene encoding PFU-RFC, which is a homolog of RFC small subunit, and a gene encoding PFU-RFCLS, which is a homolog of RFC large subunit, each derived from *Pyrococcus furiosus*.

The nucleotide sequence of the gene encoding the PFU-RFC obtained as above is determined, and an amino acid sequence deduced to be encoded thereby is examined, and the amino acid sequence is compared with the amino acid sequence of a known RFC small subunit. As a result, there has been elucidated that an intervening sequence (intein) is present in the amino acid sequence.

A region corresponding to intein is eliminated from the gene, whereby a gene comprising PFU-RFC in an expressible state can be obtained. The nucleotide sequence of an open reading frame of a region encoding PFU-RFC in the gene and the amino acid sequence of PFU-RFC deduced from the nucleotide sequence are shown in SEQ ID NOs: 4 and 3, respectively, in Sequence Listing. In addition, the nucleotide sequence of an open reading frame encoding PFU-RFCLS in the PFU-RFCLS gene and the amino acid sequence of the protein encoded thereby are shown in SEQ ID NOs: 63 and 64, respectively, in Sequence Listing. Both of these proteins are also one of concrete examples of the DNA polymerase-associated factor of the present invention.

Further, a plasmid to be used for expression of PFU-RFC can be constructed by using the gene. Such an expression plasmid includes plasmid pRFS254SNc. In addition, a transformant of *Escherichia coli* JM109, into which the plasmid is introduced, is named and identified as *Escherichia coli* JM109/pRFS254SNc, and deposited under the accession number of FERM BP-6339 with the National Institute of Bioscience and Human-Technology, Agency of Industrial Science and Technology, Ministry of International Trade and Industry, of which the address is 1–3, Higashi 1-chome, Tsukuba-shi, Ibaraki-ken (Zipcode 305-8566), Japan, since Jun. 3, 1997 (date of original deposit) under the Budapest Treaty. PFU-RFC can be obtained by culturing the transformant, and collecting from the resulting culture. With regard to PFU-RFC, it is observed that the PFU-RFC enhances an activity of a DNA polymerase when used alone, and that the PFU-RFC exhibits synergistic effects in enhancing actions as compared to a case where each protein is added alone when used in combination of F7 above.

In addition, a transformant resulting from introduction of both PFU-RFC gene and PFU-RFCLS gene is prepared, whereby a complex formed with PFU-RFC and PFU-RFCLS (hereinafter referred to as "holo-RFC"; in particular, holo-RFC produced by genetic engineering is referred to as "rRFC-M complex") can be expressed. The complex is capable of enhancing an activity of a DNA polymerase, which particularly shows high effects when used in combination with F7 mentioned above.

The above PFU-RFC and PFU-RFCLS can be further allowed to enhance a DNA polymerase activity by using a mixture with F7. In this case, a mixture of the holo-RFC (or rRFC-M complex) with F7 may be used, or a complex formed by PFU-RFC, PFU-RFCLS and F7 (RFC-N complex) may be used.

As explained above, the present invention provides a DNA polymerase-associated factor capable of enhancing DNA synthesizing-activity of a DNA polymerase, and a gene encoding the factor. The factor can be produced by genetic engineering by utilizing the gene. Further, a gene encoding a protein having an equivalent function with the DNA polymerase-associated factor of the present invention can be also obtained by genetic engineering techniques by utilizing the gene.

The DNA polymerase-associated factor of the present invention comprises a known protein involved in the DNA synthesis reaction as described above. Examples of such known proteins include ones homologous to proteins such as PCNA and RFC derived from eukaryotes. It has been said that these proteins such as PCNA and RFC form a complex to be involved in the DNA synthesis reaction with DNA polymerase δ [*Journal of Biochemistry*, 68, 1542–1548 (1996)]. However, the DNA polymerase-associated factor disclosed in the present invention is capable of enhancing an activity of a DNA polymerase with not only the complex, but also individual factors alone. Also, the factor exhibits an effect on a DNA polymerase which is structurally different from DNA polymerase δ.

The present invention can be utilized in various processes utilizing a DNA polymerase, including, for instance, nucleotide sequencing for DNA, DNA labeling, DNA amplification by PCR, and the like. The DNA polymerase-associated factor of the present invention is added to a reaction system for a DNA polymerase, whereby particularly showing an improvement in an activity of extension of DNA strand from the primer. In addition, since the factor has a high thermostability, it can be utilized for PCR, particularly for PCR in which an amplification of a long chain DNA is desirable.

Further, among the DNA polymerase-associated factors of the present invention, ones having an activity of binding to a DNA polymerase can be used for detection, purification, and the like, of the DNA polymerase. For instance, the factor can efficiently purify the bound DNA polymerase by subjecting it to affinity chromatography using a carrier to which the DNA polymerase-associated factor of the present invention is bound.

3. Method for Producing DNA Polymerase-Associated Factor of the Present Invention One of the features of the method for producing a DNA polymerase-associated factor of the present invention resides in that the method comprises culturing a transformant harboring the gene of the present invention, and collecting from the cultured medium a thermostable DNA polymerase-associated factor capable of enhancing DNA synthesizing-activity of a DNA polymerase, or possessing an activity of binding to a DNA polymerase.

In the method for producing a DNA polymerase-associated factor of the present invention, a generally employed method for purification of proteins can be applied. For instance, a DNA encoding the DNA polymerase-associated factor of the present invention is ligated to an expression vector, whereby being overexpressed under the control of a promoter of the expression vector. In addition, the DNA polymerase-associated factor of the present invention can be easily collected from a transformant harboring the gene of the present invention by a process comprising ligating a DNA encoding the DNA polymerase-associated factor of the present invention to a DNA encoding a protein such as glutathione reductase and β-galactosidase or to a DNA encoding histidine tag, to be expressed as a fusion protein. The fusion protein mentioned above can be easily isolated by using usually employed affinity column chromatography, such as nickel column. In the fusion protein mentioned above, the DNA polymerase-associated factor can be separated from a protein such as glutathione reductase or β-galactosidase by a conventional method.

In addition, the expressed DNA polymerase-associated factor of the present invention can be obtained in the same manner as the method for obtaining the DNA polymerase-associated factor of the present invention from *Pyrococcus furiosus*, the method comprising immobilizing a DNA polymerase, such as Pfu polymerase C, to an appropriate carrier, mixing the DNA polymerase-immobilized carrier with a sample containing the DNA polymerase-associated factor, removing ones unbound to the carrier, and eluting one bound thereto.

4. Method of DNA Synthesis

One of the great features of the method of DNA synthesis of the present invention resides in that a DNA is synthesized using a DNA polymerase in the presence of the DNA polymerase-associated factor of the present invention mentioned above. In the method of DNA synthesis of the present invention, a DNA is synthesized using a DNA polymerase in the presence of the DNA polymerase-associated factor of the present invention, whereby a long chain DNA of about 20 kb can be amplified.

The DNA polymerase-associated factor usable in the method of DNA synthesis of the present invention includes F1, F2, F3, F4, F5, F7, PFU-RFC, PFU-RFCLS and the like. In the method of DNA synthesis of the present invention, the DNA polymerase-associated factor may be used alone or in admixture of two or more kinds. In the method of DNA synthesis of the present invention, an even longer DNA fragment can be synthesized as compared with the length of the DNA fragment obtained in the conventional method of DNA synthesis by, for instance, using three kinds of the DNA polymerase-associated factors F7, PFU-RFC and PFU-RFCLS. In the method of DNA synthesis of the present invention, the three kinds of the DNA polymerase-associated factors may be used by mixing the three kinds each supplied singly, or they may be used in admixture two kinds of F7 and holo-RFC constituted by PFU-RFC and PFU-RFCLS (rRFC-M complex). Further, the three kinds of the DNA polymerase-associated factors may be used as a complex constituted by F7, PFU-RFC and PFU-RFCLS (RFC-N complex).

The DNA polymerase used in the method of DNA synthesis of the present invention includes DNA polymerases such as pol I derived from *E. coli;* and thermostable DNA polymerases such as Tth DNA polymerase derived from *Thermus thermophilus,* Taq DNA polymerase derived from *Thermus aquaticus,* and Pfu DNA polymerase derived from *Pyrococcus furiosus.*

In addition, in the method of DNA synthesis of the present invention, a DNA can be synthesized by PCR method using the DNA polymerase mentioned above.

In the method of DNA synthesis of the present invention, the amount of the DNA polymerase-associated factor of the present invention to be present is not particularly limited, and an amount sufficient for exhibiting an activity of enhancing synthesizing-activity of the DNA polymerase may be used.

5. Kit Comprising DNA Polymerase-Associated Factor of the Present Invention

The DNA polymerase-associated factor of the present invention can be utilized in various reactions in which a DNA polymerase is used. Therefore, the DNA polymerase-associated factor of the present invention is attached to a kit usable for in vitro DNA synthesis, including, for instance, a kit for nucleotide sequencing of DNA by the dideoxy method, a kit for DNA labeling, a PCR kit, whereby improving the performance of each of these kits. Besides ones containing the DNA polymerase and the DNA polymerase-associated factor of the present invention, the kit as described above may comprise a reagent required for the reaction of a DNA polymerase, the reagent including, for instance, dNTP and $MgCl_2$. The DNA polymerase-associated factor contained in the kit of the present invention includes F1, F2, F3, F4, F5, F7, PFU-RFC and PFU-RFCLS. In the kit of the present invention, the DNA polymerase-associated factor may be used alone or in admixture of two or more kinds. It is preferable to use three kinds of the DNA polymerase-associated factors F7, PFU-RFC and PFU-RFCLS. Each of the three kinds of the DNA polymerase-associated factors may be used by mixing each of the three kinds supplied singly. Also, there may be used in admixture of two kinds F7 and holo-RFC constituted by PFU-RFC and PFU-RFCLS (rRFC-M complex). Further, the three kinds of the DNA polymerase-associated factors may be used as a complex constituted by F7, PFU-RFC and PFU-RFCLS (RFC-N complex). The DNA polymerase contained in the kit of the present invention also includes DNA polymerases such as pol I derived from *E. coli*; and thermostable DNA polymerases such as Tth DNA polymerase derived from *Thermus thermophilus,* Taq DNA polymerase derived from *Thermus aquaticus,* Pfu DNA polymerase derived from *Pyrococcus furiosus.* In the kit of the present invention, it is preferable that the kit comprises a thermostable DNA polymerase. The kit of the present invention is used for the method of DNA synthesis, whereby a high molecular DNA can be synthesized more simply.

EXAMPLES

The present invention is hereinafter described by means of the following examples, but the scope of the present invention is not limited only to those examples.

Example 1

(1) Preparation of *Pyrococcus furiosus* Genomic DNA *Pyrococcus furiosus* DSM3638 was Cultured in the Following Manner A medium having a composition comprising 1% trypton, 0.5% yeast extract, 1% soluble starch, 3.5% Jamarin S Solid (manufactured by Jamarin Laboratory), 0.5% Jamarin S Liquid (manufactured by Jamarin Laboratory), 0.003% $MgSO_4$, 0.001% NaCl, 0.0001% $FeSO_4 \cdot 7H_2O$, 0.0001% $COSO_4$, 0.0001% $CaCl_2 \cdot 7H_2O$, 0.0001% $ZnSO_4$, 0.1 ppm $CuSO_4 \cdot 5H_2O$, 0.1 ppm $KAl(SO_4)_2$, 0.1 ppm $H_3BO_3$, 0.1 ppm $Na_2MoO_4 \cdot 2H_2O$, and 0.25 ppm $NiCl_2 \cdot 6H_2O$ was placed in a two-liter medium bottle and sterilized at 120° C. for 20 minutes. After sparging with nitrogen gas thereinto for removal of dissolved oxygen, the above strain was inoculated into the resulting medium. Thereafter, the medium was cultured by allowing to stand at 95° C. for 16 hours. After termination of the cultivation, cells were harvested by centrifugation.

The harvested cells were then suspended in 4 ml of 0.05 M Tris-HCl (pH 8.0) containing 25% sucrose. To this suspension, 0.8 ml of lysozyme [5 mg/ml, 0.25 M Tris-HCl (pH 8.0)] and 2 ml of 0.2 M EDTA were added, and the resulting mixture was incubated at 20° C. for 1 hour. Thereafter, 24 ml of an SET solution [150 mM NaCl, 1 mM EDTA, and 20 mM Tris-HCl (pH 8.0)] was added thereto, and 4 ml of 5% SDS and 400 µl of proteinase K (10 mg/ml) were further added to the resulting mixture. Thereafter, the resulting mixture was reacted at 37° C. for 1 hour. After termination of the reaction, phenol-chloroform extraction and subsequent ethanol precipitation were carried out to prepare about 3.2 mg of genomic DNA.

(2) Preparation of Cosmid DNA Library

Four hundred micrograms of the genomic DNA from *Pyrococcus furiosus* DSM3638 was partially digested with Sau3A1 and fractionated by size into 35 to 50 kb fractions by density gradient ultracentrifugation method. Next, 1 µg of triple helix cosmid vector (manufactured by Stratagene) was digested with XbaI, and thereafter dephosphorylated using an alkaline phosphatase (manufactured by Takara Shuzo Co., Ltd.), and further digested with BamHI. The resulting treated vector was mixed with 140 µg of the above 35 to 50 kb DNA fractions, and the mixture was subjected to ligation reaction. The cosmid carrying the genomic DNA fragment from *Pyrococcus furiosus* was packaged into lambda phage particles by in vitro packaging method using the resulting reaction mixture and "GIGAPACK GOLD" (manufactured by Stratagene), to prepare cosmid library. Subsequently, a portion of this library was transduced into *E. coli* DH5αMCR (manufactured by BRL). Five hundred clones were selected from the resulting transformants, each named as Cosmid Clone No. 1 to No. 500. Further, a cosmid DNA was prepared from each of these clones. Several of them out of the resulting cosmid DNAs were selected and digested with a restriction enzyme to confirm the presence of an insert of an appropriate size.

(3) Cloning of Pfu Polymerase C Gene

There was prepared as a reaction solution 20 mM Tris-HCl (pH 7.7), 2 mM $MgCl_2$, 2 mM 2-mercaptoethanol, 0.2 mg/ml activated DNA, 40 µM each of dATP, dCTP, dGTP and dTTP, 60 nM [$^3$H]-dTTP (manufactured by Amersham). To 45 µl of the reaction solution was added a 1 µl extract in 5 clone equivalent (5 µl) derived from each clone of the above cosmid DNA library, and the mixture was reacted at 75° C. for 15 minutes. Thereafter, a 40 µl aliquot of this reaction mixture was then spotted onto DE paper and washed with 5% $Na_2HPO_4$ five times. The remaining radioactivity on the DE paper was determined using a liquid scintillation counter. Primary determination was carried out with one group consisting of 5 clones. The group found to have some activities was subsequently separated into one clone each from the 5 clones, and secondary determination was then carried out. Since it had been already known from a hybridization test with the gene as a probe that those clones in the cosmid DNA library containing a known DNA polymerase gene were Clone Nos. 57, 154, 162 and 363, there were obtained five clones of Clone Nos. 41, 153, 264, 462 and 491 possessing DNA synthesizing-activity other than those clones.

Cosmids were isolated from the above five clones, and each isolated cosmid was digested with BamHI. When examining the resulting electrophoretic patterns, there were found several mutually common bands, predicting that those five clones recombine regions with overlaps and slight shifts. With this finding in mind, the restriction endonuclease map was prepared for the DNA inserts in Clone Nos. 264 and 491. On the basis of the resulting restriction endonuclease map, various DNA fragments of 10 kbp or so in length were cut out from the cosmid derived from Clone 264 or 491. The fragments were then subcloned into pTV118N or pTV119N vector (manufactured by Takara Shuzo Co., Ltd.). The thermostable DNA polymerase activity was measured for the resulting transformant harboring the recombinant plasmid obtained. As a result, it was found that a gene for producing a highly thermostable DNA polymerase was present on an XbaI-XbaI fragment of about 10 kbp. A plasmid resulting from incorporation of the XbaI-XbaI fragment into pTV118N vector was then named as plasmid pFU1001, and the *Escherichia coli* JM109 transformed with the plasmid was named as *Escherichia coli* JM109/pFU1001 (FERM BP-5579).

(4) Analysis of DNA Polymerase-Constituting Protein of Pfu Polymerase C

The above XbaI-XbaI fragment containing the DNA polymerase gene, was again cut out from the above plasmid pFU1001 with XbaI, and blunt-ended using DNA blunting kit (manufactured by Takara Shuzo Co., Ltd.). The resultant was then ligated to new pTV118N vector, previously linearized with SmaI, to yield plasmids for preparing deletion mutants. The resulting plasmids were named as pFU1002 and pFU1003, respectively, in accordance with the orientations of the inserts. Deletion mutants were prepared from sequentially deleting from both ends of the DNA insert using these plasmids. Kilo-Sequence Deletion kit (manufactured by Takara Shuzo Co., Ltd.) applying Henikoff's method (*Gene*, 28, 351–359) was used for the above preparation. The 3'-overhanging and 5'-overhanging restriction enzymes used were PstI and XbaI, respectively. The nucleotide sequence of the insert was determined by the dideoxy method using BcaBEST dideoxy sequencing kit (manufactured by Takara Shuzo Co., Ltd.) with the various deletion mutants as templates. The resulting nucleotide sequence was analyzed, and as a result, there were found six open reading frames (ORFs). The thermostable DNA polymerase activity was determined using the above various deletion mutants. The results demonstrated that the translation products of the ORF3 and the ORF4 were important in the exhibition of the DNA polymerase activity. The amino acid sequence of the ORF3 is shown in SEQ ID NO: 5 in Sequence Listing, and the amino acid sequence is shown in SEQ ID NO: 6 in Sequence Listing, respectively. In other words, the Pfu polymerase C is an enzyme comprising two kinds of the DNA polymerase-constituting proteins having amino acid sequences as shown in SEQ ID NO: 5 and SEQ ID NO: 6 in Sequence Listing, respectively.

Example 2

(1) Preparation of Pfu Polymerase C

Pfu polymerase C used as an antigen was prepared in the following manner. *Escherichia coli* JM109/pFU1001 was cultured in 2 liter of LB medium (1.0% trypton, 0.5% yeast extract, 0.5% NaCl, pH 7.2) containing 100 μg/ml ampicillin. When the turbidity of the culture reached 0.6 in $A_{600}$, an inducer, isopropyl-β-D-thiogalactoside (IPTG) was added so as to have a final concentration of 1 mM, and cultured for additional 16 hours. After harvesting, the harvested cells were suspended in 37 ml of sonication buffer [50 mM Tris-HCl, pH 8.0, 2 mM 2-mercaptoethanol, 10% glycerol, 2 mM PMSF (phenylmethanesulfonyl fluoride)], and the suspension was treated with an ultrasonic disrupter. The supernatant resulting from centrifugation of the disrupted solution at 12,000 rpm for 10 minutes was heat-treated at 80° C. for 15 minutes. Thereafter, centrifugation was again carried out at 12,000 rpm for 10 minutes and the supernatant was recovered, to yield 33 ml of a heat-treated supernatant. Subsequently, the above solution was subjected to 2-hour dialysis for 4 times with 2 liter of buffer A [50 mM potassium phosphate, pH 6.5, 2 mM 2-mercaptoethanol, 10% glycerol] as a dialysate. After dialysis, 32 ml of the enzyme solution was applied to RESOURCE Q column (manufactured by Pharmacia) which was previously equilibrated with buffer A, and the applied solution was chromatographed using FPLC system (manufactured by Pharmacia). The elution was carried out on a linear concentration gradient from 0 to 500 mM NaCl. A fraction having a DNA polymerase activity was eluted at 340 mM NaCl.

Ten milliliters of an enzyme solution obtained by collecting an active fraction was concentrated by using Centriflow CF-50 (manufactured by Grace Japan), and the concentrated enzyme solution was then subjected to exchange with buffer A containing 150 mM NaCl with PD-10 column (manufactured by Pharmacia) to yield 3.5 ml of an enzyme solution. The resulting enzyme solution was then applied to HiTrap Heparin column (manufactured by Pharmacia), previously equilibrated with the same buffer. An active fraction eluted at a concentration of 400 mM NaCl was obtained by eluting with a linear concentration gradient from 150 to 650 mM NaCl using FPLC system. Five milliliters of this fraction was concentrated by ultrafiltration using Centricon-10 (manufactured by Amicon), and 120 μl of the resulting concentrate was applied to Superose 6 gel filtration column (manufactured by Pharmacia), previously equilibrated with 50 mM potassium phosphate buffer (pH 6.5) containing 75 mM NaCl and 2 mM 2-mercaptoethanol, and the elution was carried out with the same buffer. As a result, a fraction having a DNA polymerase activity was eluted at positions corresponding to retention times of 34.7 minutes and 38.3 minutes. The fraction eluted at the position of 38.3 minutes was concentrated, and the resulting concentrate was used as an antigen in the preparation of an anti-Pfu polymerase C polyclonal antibody.

Incidentally, in the purification of the above Pfu polymerase C, the enzyme activity was determined in the following manner. An activated calf thymus DNA (manufactured by Worthington) (activated DNA) was used as a substrate. Determinations of DNA activation and DNA polymerase activity were carried out by the method described in DNA Polymerase from *Escherichia coli*, 263–276 (authored by C. C. Richardson), published by Harper & Row, edited by D. R. Davis. To 5 μl of a sample of which the activity was to be determined was added 45 μl of a reaction solution [20 mM Tris-HCl (pH 7.7), 15 mM $MgCl_2$, 2 mM 2-mercaptoethanol, 0.2 mg/ml activated DNA, 40 μM each of dATP, dCTP, dGTP and dTTP, 60 nM [$^3$H]-dTTP (manufactured by Amersham)]. The resulting mixture was reacted at 75° C. for 5 minutes. A 40 μl portion of this reaction mixture was then spotted onto DE paper (manufactured by Whatman) and washed with 5% $Na_2HPO_4$ five times. The remaining radioactivity on the DE paper was determined using a liquid scintillation counter. The amount of enzyme which incorporated 10 nmol of [$^3$H]-dTMP per 30 minutes into the substrate DNA, determined by the above-described enzyme activity determination method, was defined as one unit of the enzyme.

(2) Preparation of Anti-Pfu Polymerase C Antibody

The above Pfu polymerase C preparation was diluted with 50 mM potassium phosphate, pH 6.5, 2 mM 2-mercaptoethanol, and 75 mM NaCl so as to have a concentration of 1 mg/100 μl. Thereto was added an equal volume of complete Freund's adjuvant, and the mixture was emulsified. The resulting emulsion was subcutaneously injected at 50 μl per injection to rabbit 4 times in 3-week intervals. Whole blood was extracted 10 days after the final immunization, and the extracted blood was allowed to stand at room temperature for 60 minutes. Thereafter, the blood was centrifuged to yield 60 ml of antisera containing anti-Pfu polymerase C polyclonal antibody. To 20 ml of the antisera was added 20 ml of saturated ammonium sulfate solution. The mixture was gently stirred at 4° C. for 45 minutes, and centrifuged. The resulting precipitate was suspended in 5 ml of 20 mM sodium phosphate buffer, pH 7.0, and the suspension was subjected to a 2-hour dialysis for 3 times using 2 liters of the same buffer as a dialysate. After dialysis, 14 ml of the solution was applied to protein A column (manufactured by Pharmacia), previously equilibrated with 20 mM sodium phosphate buffer (pH 7.0), washed with the same buffer, and then eluted with 0.1 M sodium citrate buffer (pH 3.0). The eluted anti-Pfu polymerase C polyclonal antibody was neutralized with 1 M Tris-HCl, pH 9.0, and concentrated with Centriflow CF-50, and subjected to exchange with coupling buffer (0.5 M NaCl, 0.2 M NaHCO$_3$, pH 8.3) with PD-10 column (manufactured by Pharmacia), to prepare a solution containing anti-Pfu polymerase C polyclonal antibody.

(3) Preparation of Anti-Pfu Polymerase C Antibody Column

HiTrap NHS-activated column (manufactured by Pharmacia) was washed with 6 ml of 1 mM HCl, and 0.9 ml of the above anti-Pfu polymerase C polyclonal antibody solution (containing 3.6 mg equivalent of the anti-Pfu polymerase C polyclonal antibody) was then applied to HiTrap NHS-activated column. After allowing to stand at room temperature for 1 hour, the resulting column was washed with 3 ml of the coupling buffer. Subsequently, the column was sequentially washed with 6 ml of blocking buffer (0.5 M Tris-HCl, pH 8.3, 0.5 M NaCl), 6 ml of buffer B (0.1 M sodium acetate, pH 4.0, 0.5 M NaCl), and 6 ml of the blocking buffer, and the resulting mixture was allowed to stand at room temperature for 30 minutes. Further, the column was washed with 6 ml of buffer B, 6 ml of the blocking buffer, and 6 ml of buffer B, and thereafter the column was equilibrated with 50 mM Tris-HCl, pH 8.0, to prepare an anti-Pfu polymerase C antibody column.

Example 3

(1) Purification of Complex Comprising Pfu Polymerase C Using Anti-Pfu Polymerase C Antibody Column

*Pyrococcus furiosus* DSM3638 was cultured in two medium bottles for 16 hours in the same manner as the method described in Example 1. After harvesting, cells were suspended in 34.7 ml of buffer C (50 mM Tris-HCl, pH 8.0, 1 mM ATP) containing 2 mM PMSF, and the suspension was treated with an ultrasonic disrupter. The disrupted solution was centrifuged at 12,000 rpm for 10 minutes, and 46 ml of the supernatant obtained was applied to an anti-Pfu polymerase C antibody column, previously equilibrated with buffer C. After the column was washed with buffer C, the complex comprising Pfu polymerase C was eluted with elution buffer (0.1 M glycine-HCl, pH 2.5, 1 mM ATP). After neutralization with 1 M Tris-HCl, pH 9.0, the eluate was concentrated using Centriflow CF-50 to yield a Pfu polymerase C complex concentrate.

(2) Analysis of Pfu Polymerase C Complex

The Pfu polymerase C complex concentrate was subjected to SDS-PAGE (12.5% polyacrylamide gel; 25 mM Tris-HCl, 192 mM glycine, 0.1% SDS, pH 8.4 being used as electrophoresis buffer). The gel obtained was analyzed by Western blotting using the anti-Pfu polymerase C antibody by the method shown below. After SDS-PAGE, the gel was immersed in blotting buffer 1 (25 mM Tris-HCl, 20% methanol, pH 9.4) containing 40 mM ε-amino-n-caproic acid. Next, filter papers immersed in blotting buffer 2 (0.3 M Tris-HCl, 20% methanol, pH 10.4), filter papers immersed in 25 mM Tris-HCl and 20% methanol, pH 10.4, a PVDF membrane immersed in blotting buffer 1 containing 40 mM ε-amino-n-caproic acid, the above gel, and filter papers immersed in blotting buffer 1 containing 40 mM ε-amino-n-caproic acid were overlaid on semi-dry blotting apparatus (manufactured by Scientific), and blotting was carried out at 2 mA/cm$^2$ for 1 hour. This PVDF membrane was immersed in Block Ace (manufactured by Snow Brand Milk Products Co., Ltd.) containing 0.01% thimerosal, shaken for 10 minutes, and thereafter the membrane was immersed in an anti-Pfu polymerase C antiserum, previously diluted 1,000 fold with Block Ace containing 0.01% thimerosal. After allowing to stand at room temperature for 1 hour, the membrane was washed thrice for 10 minutes with TBS buffer (50 mM Tris-HCl, pH 7.5, 150 mM NaCl) containing 0.02% Tween-20 and further washed with TBS buffer. The membrane was then immersed in a peroxidase-labeled anti-rabbit IgG (Fc) antibody (manufactured by Organon-Technica), previously diluted 5,000 fold with Block Ace containing 0.01% thimerosal. After allowing to stand at room temperature for 1 hour, the PVDF membrane was washed thrice for 10 minutes with TBS buffer containing 0.02% Tween-20 and further washed with TBS buffer. Thereafter, the membrane was immersed in Konica Immunostain HRP-1000 (manufactured by Konica Corporation) to allow color development. From the results of staining of the gel after SDS-PAGE with Coomassie Brilliant Blue R-250, shown in FIG. 1, and the results of the Western blotting mentioned above, it was elucidated that the above complex fraction contained seven kinds of proteins (F1 to F7 in FIG. 1) unreactive with the anti-Pfu polymerase C antibody.

Since the bands unreactive with the anti-Pfu polymerase C antibody are considered to be proteins adsorbed to the column via Pfu polymerase C, N-terminal amino acid sequences of these proteins were analyzed by the method described below. The Pfu polymerase C complex concentrate obtained in Example 3(1) was subjected to SDS-PAGE and blotted onto a PVDF membrane in the same manner as above. After this membrane was stained with Coomassie Brilliant Blue R-250, the desired bands were cut out. The N-terminal amino acid sequences of the desired proteins were determined by automatic Edman decomposition with G1000A Protein Sequencer (manufactured by Hewlett-Packard Company) using these membrane fragments as samples. The results are shown in Table 1. The N-terminal amino acid sequences obtained, F1 to F5 and F7, are shown in SEQ ID NOs: 7 to 12, respectively, in Sequence Listing.

TABLE 1

| Sample | N-Terminal Amino Acid Sequence |
|--------|-------------------------------|
| F1 | MDKEGFLNKVREAVDVVKLH |
| F2 | MFTGKVLIPVKVLKKFENWN |
| F3 | MIGSIFYSKKFNLHRPSEYH |
| F4 | MKDYRPLLGAIKVKGDNVFS |
| F5 | MDIEVLRRLLERELSSEH |
| F6 | Unable to be analyzed |
| F7 | PFEIVFEGAKEFAQLID |

Example 4

Preparation of Cassette DNAs

Ten micrograms of *Pyrococcus furiosus* genomic DNA prepared in Example 1 was completely digested with EcoRI (manufactured by Takara Shuzo Co., Ltd.), and 500 ng equivalent of the digest was mixed with 50 ng of EcoRI cassette (manufactured by Takara Shuzo Co., Ltd.), followed by ligation. The DNA recovered from the ligation reaction mixture for ligation by ethanol precipitation was dissolved in 20 μl of sterilized water, and this solution was used as EcoRI cassette DNA for the subsequent procedures.

Using similar procedures as those described above, cassette DNAs ligated with each of HindIII cassette, XbaI cassette, SalI cassette, PstI cassette and Sau3AI cassette (all manufactured by Takara Shuzo Co., Ltd.) were prepared. When ligated with the XbaI cassette, genomic DNA digested with two enzymes, i.e., XbaI and NheI, was used, and each of the DNAs obtained were named XbaI cassette DNA and NheI/XbaI cassette DNA, respectively. When ligated with the SalI cassette, genomic DNA digested with the two enzymes SalI and XhoI was used, and each of the DNAs obtained were named SalI cassette DNA and XhoI/SalI cassette DNA, respectively. When ligated with the Sau3AI cassette, genomic DNA digested with BglII was used, and the DNA obtained was named BglII/Sau3AI cassette DNA.

Example 5

(1) Selection of Cosmid Clones Carrying F1 Gene

On the basis of the N-terminal amino acid sequence of F1 obtained in Example 3, the primers F1-1 and F1-2, of which nucleotide sequences are shown in SEQ ID NOs: 13 and 14, respectively, in Sequence Listing, were synthesized. First PCR was carried out using 100 pmol each of F1-1 and the cassette primer C1 (manufactured by Takara Shuzo Co., Ltd.) with 1 μl of the EcoRI cassette DNA prepared in Example 4 as a template. Second PCR was carried out using 100 pmol each of F1-2 and the cassette primer C2 (manufactured by Takara Shuzo Co., Ltd.) with 1 μl of the resulting reaction mixture obtained as above as a template. For the two PCRs, Pfu DNA polymerase (α-type enzyme, manufactured by STRATAGENE) was used. The reaction mixture composition and reaction conditions are shown below: The reaction mixture comprises 20 mM Tris-HCl, pH 8.2, 10 mM KCl, 20 mM $MgCl_2$, 6 mM $(NH_4)_2SO_4$, 0.2 mM each of dATP, dCTP, dGTP, dTTP, 1% Triton X-100, 0.01% BSA and 2.5 units of Pfu DNA polymerase (final volume being 100 μl), and the reaction was carried out in 30 cycles for the first PCR and in 25 cycles for the second PCR, wherein one cycle comprises a process consisting of at 94° C. (30 seconds)—45° C. (30 seconds)—72° C. (2 minutes). The PCR using Pfu DNA polymerase described in the Examples below was also carried out using the same reaction mixture composition. An amplified DNA fragment of about 550 bp was subcloned into plasmid vector pUC119 (manufactured by Takara Shuzo Co., Ltd.), and its nucleotide sequence was determined. Thereafter, on the basis of the sequence determined, the primers F1S1 and F.S2, of which nucleotide sequences are shown in SEQ ID NOs: 15 and 16, respectively, in Sequence Listing, were then synthesized. PCR was carried out using these F1S1 and F1S2 with the cosmid DNA mentioned in Example 1 as a template, whereby selecting cosmid clones carrying the F1 gene. This PCR was carried out using TaKaRa PCR amplification kit (manufactured by Takara Shuzo Co., Ltd.) in accordance with the instructions attached. As a result, there were found that cosmid clone Nos. 22, 46, 61, 133, 178, 180, 210 and 317 carry the F1 gene.

(2) Subcloning of F1 Gene

Figure 2:
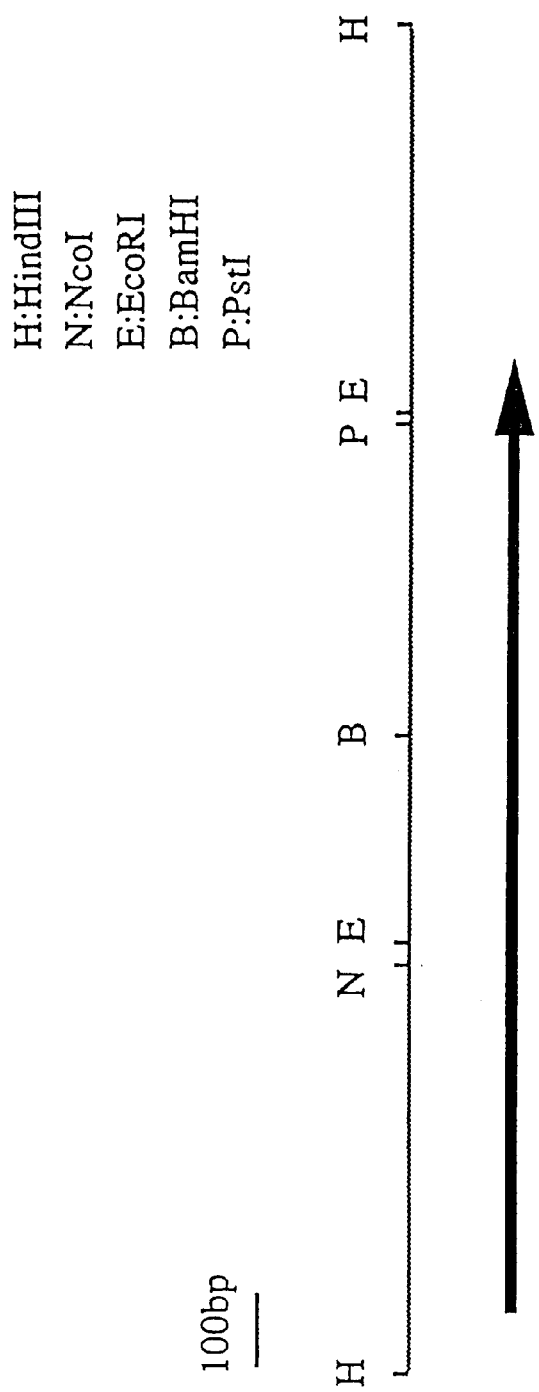
FIG. 2 is a restriction endonuclease map of a DNA insert of the plasmid pF1-4-10 carrying a gene encoding the F1 protein.

PCR was carried out using 20 pmol each of F1S1 and the cassette primer C2, or each of F1S2 and the cassette primer C2, with 1 μl of the HindIII cassette DNA prepared in Example 4 as a template. The PCR was carried out with the same reaction mixture composition as that used in Example 5(1) using Pfu DNA polymerase as an enzyme in 50 cycles, wherein one cycle comprises a process consisting of at 94° C. (30 seconds)—55° C. (30 seconds)— 72° C. (3 minutes). As a result, a DNA fragment of 570 bp was amplified by F1S2 and the cassette primer C2, whereas no DNA was amplified by F1S1 and the cassette primer C2. This finding anticipated that the HindIII site is located immediately upstream of the initiation codon for the F1 gene and at a distance from the annealing position of F1S1 such that DNA cannot be amplified by Pfu DNA polymerase. With this in mind, Cosmid Clone No. 61, randomly selected from the cosmid clones carrying the F1 gene, was digested with HindIII, and DNA fragments of not smaller than 1.5 kb were isolated, and each was subcloned into plasmid vector pTV118N (manufactured by Takara Shuzo Co., Ltd.). PCR was carried out using F1S1 and F1S2 as primers with each recombinant plasmid obtained as a template, to examine for the presence of the F1 gene. As a result, it was found that a HindIII fragment of about 2 kb carries the F1 gene. A plasmid in which the F1 gene in this DNA fragment ligated to downstream of the lac promoter of pTV118N vector was named pF1-4-10. As to the DNA inserts contained in this plasmid, a restriction endonuclease map for NcoI, EcoRI, BamHI, PstI, SacI and NdeI was prepared. The results as shown in FIG. 2 were obtained.

(3) Determination of Nucleotide Sequence of DNA Fragment Carrying F1 Gene

There was determined by the dideoxy method the nucleotide sequence of the DNA insert in the plasmid pF1-4-10 and each plasmid obtained by cutting out the NcoI-HindIII, EcoRI-EcoRI, BamHI-PstI, EcoRI-HindIII, HindIII-EcoRI and HindIII-BamHI fragments from the plasmid, and subcloning each of the resulting fragments into plasmid vector pTV119N (manufactured by Takara Shuzo Co., Ltd.). A sequence of 2,009 bp in the nucleotide sequences of the DNA insert in pF1-4-10 determined totally on the basis of these results combined together is as shown in SEQ ID NO: 17 in Sequence Listing. As a result of analyzing the nucleotide sequence, there was revealed an open reading frame comprising the N-terminal amino acid sequence of F1. The above sequence is shown in SEQ ID NO: 18 in Sequence Listing, and the amino acid sequence of the F1 translation product as deduced from the above sequence is shown in SEQ ID NO: 19 in Sequence Listing, respectively. This amino acid sequence was searched for homology to the amino acid sequences of known proteins. As a result, it was found to be homologous to the *Haemophilus influenzae*-derived single-stranded DNA-specific exonuclease [*Science*, 269, 496–512 (1995)]. The homology was 23.2% for the first half and 24.3% for the last half.

(4) Construction of Plasmid for F1 Expression

PCR was carried out using the primer F1Nc, of which nucleotide sequence is shown in SEQ ID NO: 20 in Sequence Listing, and the above primer F1S2 with the plasmid pF1-4-10 described in Example 5(2) as a template. The PCR was carried out in a reaction mixture of the same composition as that used in Example 5(1) using Pfu DNA polymerase. Using 1 ng of template DNA and 20 pmol each of the two primers, the reaction was carried out in 25 cycles, wherein one cycle comprises a process consisting of at 94° C. (30 seconds)—55° C. (30 seconds)—72° C. (2 minutes). A fragment obtained by digesting an amplified DNA fragment of about 460 base pairs with NcoI and BglIII (both manufactured by Takara Shuzo Co., Ltd.) and a DNA fragment obtained by digesting the above plasmid pF1-4-10 with BglII and HindIII were together inserted between the NcoI and HindIII sites of plasmid vector pTV118N (manufactured by Takara Shuzo Co., Ltd.). This plasmid was named pF1Nc-2. Of the DNA insert in the plasmid, in the PCR-amplified region, the nucleotide sequence was confirmed by the dideoxy method that there is no mutation caused by PCR.

(5) Preparation of Purified F1 Authentic Sample *Escherichia coli* JM109/pF1Nc2, *Escherichia coli* JM109 transformed with the plasmid pF1Nc-2 obtained in Example 5(4), was cultured for 16 hours in 2 liters of LB medium containing 100 μg/ml ampicillin. After harvesting the cells, 33 ml of a heat-treated supernatant was obtained in the same manner as Example 2(1). Next, this solution was applied to RESOURCE Q column (manufactured by Pharmacia), previously equilibrated with buffer D (50 mM Tris-HCl, pH 8.0, 2 mM 2-mercaptoethanol, 10% glycerol), and the applied solution was chromatographed using FPLC system (manufactured by Pharmacia). The elution was carried out on a linear concentration gradient of 0 to 500 mM NaCl. F1 was eluted at 340 mM NaCl.

After 10 ml of the enzyme solution obtained by collecting the F1 fraction was concentrated using Centriflow CF50, the resulting concentrate was subjected to exchange with buffer D using PD-10 column (manufactured by Pharmacia), and 3.5 ml of the solution was applied to HiTrap Blue column (manufactured by Pharmacia), previously equilibrated with the same buffer. Using FPLC system, the column was washed with buffer D, and thereafter F1 was eluted with buffer D containing 2 M NaCl. Five milliliters of this fraction was concentrated using Centricon-10, and 120 µl of the concentrate was applied to Superdex 200 gel filtration column (manufactured by Pharmacia), previously equilibrated with 50 mM Tris-HCl, pH 8.0, containing 2 mM 2-mercaptoethanol and 75 mM NaCl. The elution was carried out with the same buffer, and as a result, F1 was eluted at a position corresponding to a molecular weight of about 49 kilodaltons. This molecular weight corresponds to the case where F1 is present as a monomer.

(6) Determination of Exonuclease Activity

The 5'→3' and 3'→5' exonuclease activities of the purified F1 authentic sample were examined in the following manner.

First, plasmid vector pUC119 (manufactured by Takara Shuzo Co., Ltd.) was digested with SspI (manufactured by Takara Shuzo Co., Ltd.) and subjected to agarose gel electrophoresis, and a DNA fragment of 386 bp was recovered from the gel and purified. This DNA fragment was labeled at the 5'-terminus using [γ-$^{32}$P]-ATP (manufactured by Amersham) and polynucleotide kinase (manufactured by Takara Shuzo Co., Ltd.), and the $^{32}$P-labeled DNA fragment obtained was used as a substrate for detecting the 5'→3' exonuclease activity. In addition, plasmid vector pUC119 was digested with Sau3AI (manufactured by Takara Shuzo Co., Ltd.), and a DNA fragment of 341 bp obtained was recovered and purified in the same manner as above. Furthermore, this DNA fragment was $^{32}$P-labeled at the 3'-terminus by the fill-in reaction using [α-$^{32}$P]-dCTP (manufactured by Amersham) and Klenow fragment (manufactured by Takara Shuzo Co., Ltd.) to yield a substrate for detecting the 3'→5' exonuclease activity. The above two kinds of labeled DNAs were purified by gel filtration through NICK column (manufactured by Pharmacia) and used for the reaction described below.

Ten microliters of a reaction mixture (20 mM Tris-HCl, pH 7.7, 15 mM MgCl$_2$, 2 mM 2-mercaptoethanol) containing 2 ng of each of these labeled DNA fragments and 12.5 µg of digest obtained by completely digesting λ-DNA (manufactured by Takara Shuzo Co., Ltd.) with HaeIII (manufactured by Takara Shuzo Co., Ltd.), and the above purified F1 authentic sample was prepared and reacted at 85° C. for 2.5, 5 or 7.5 minutes, and thereafter ethanol precipitation was carried out to precipitate the DNA. By determining the radioactivity in this supernatant using a liquid scintillation counter, the amount of substrate decomposed by exonuclease activity was determined. In the determination of the 5'→3' exonuclease activity, 50 fmol of the purified F1 authentic sample was added, and in the determination of the 3'→5' exonuclease activity, 125 pmol of the purified F1 authentic sample was added. These results are shown in FIGS. 3 and 4, respectively.

Figure 3:
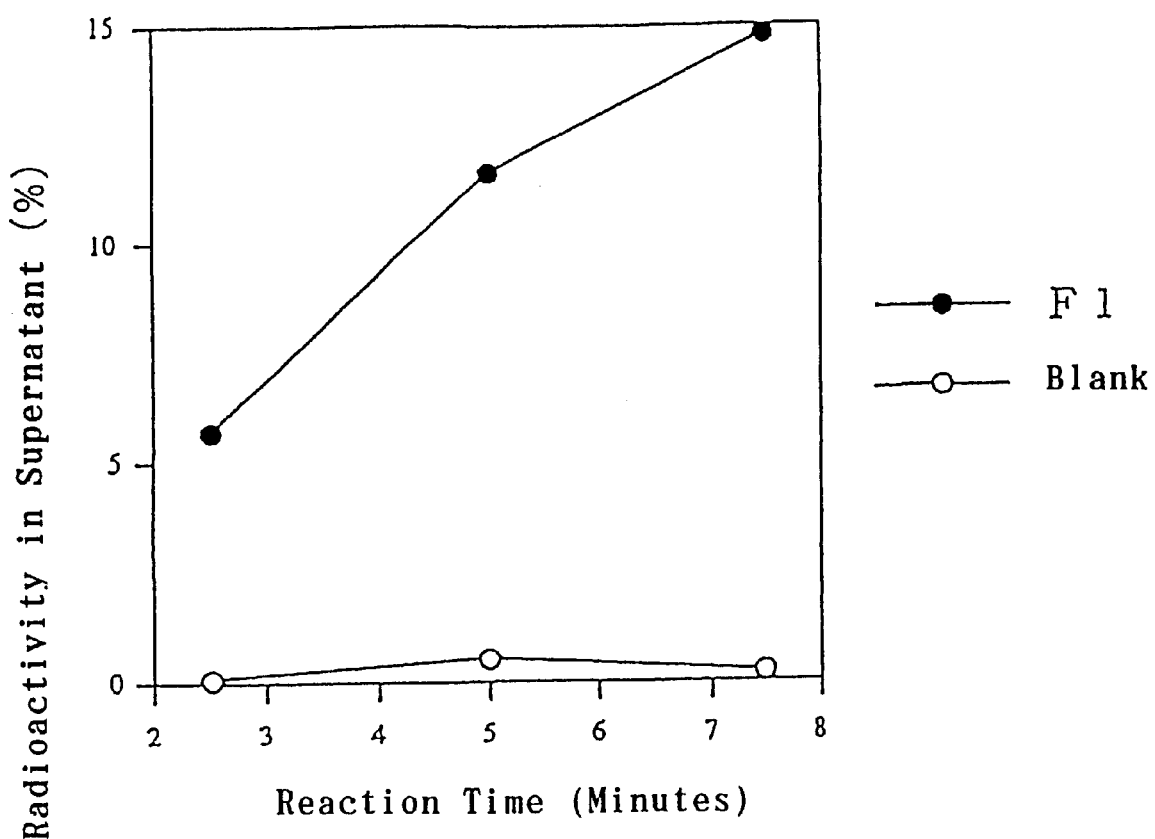
FIG. 3 is a graph showing a 5'→3' exonuclease activity of the F1 protein.
Figure 4:
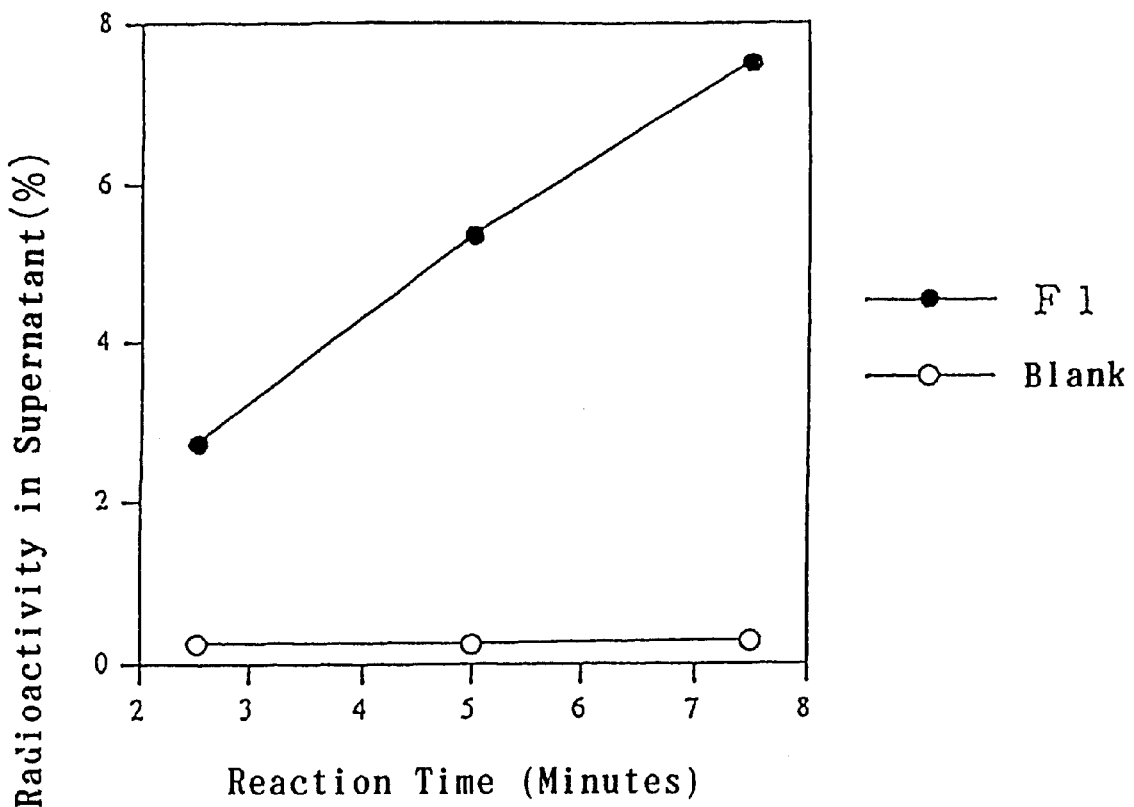
FIG. 4 is a graph showing a 3'→5' exonuclease activity of the F1 protein.

FIG. 3 shows the results for the determination of 5'→3' exonuclease activity, and FIG. 4 shows the results for determination of the 3'→5' exonuclease. In the figures, the abscissa indicates reaction time, and the ordinate indicates the ratio of radioactivity released in the supernatant to that contained in the entire reaction mixture. In addition in the figures, solid circles indicate the results obtained with the purified F1 authentic sample of the present invention, and open circles indicate a blank reaction without adding the purified F1 authentic sample. As shown in the figures, the purified F1 authentic sample of the present invention possesses both 5'→3' and 3'→5' exonuclease activities. Also, from the above results it was demonstrated that the 5'→3' exonuclease activity is about 500 times as great as the 3'→5' exonuclease activity.

Example 6

(1) Selection of Cosmid Clones Carrying F2 Gene

On the basis of the N-terminal amino acid sequence of F2 obtained in Example 3, the primers F2-2 and F2-3, of which nucleotide sequences are shown in SEQ ID NOs: 21 and 22, respectively, in Sequence Listing, were synthesized. First PCR was carried out using 100 pmol of the primer F2-2 and 20 pmol of the cassette primer C1 with 1 µl of the XbaI cassette DNA prepared in Example 4 as a template. Second PCR was carried out using 100 pmol of the primer F2-3 and 20 pmol of the cassette primer C2 with 1 µl of the resulting reaction mixture obtained as above as a template. For the two PCRs, Pfu polymerase C was used. The reaction mixture composition and reaction conditions are shown below: The reaction mixture comprises 10 mM Tris-HCl, pH 9.2, 75 mM KCl, 3.5 mM MgCl$_2$, 0.4 mM each of dATP, dCTP, dGTP and dTTP, 0.1% Triton X-100, 0.01% BSA and 2.0 units of Pfu polymerase C (final volume being 100 µl), and the reaction was carried out in 30 cycles for the first PCR and 25 cycles for the second PCR, wherein one cycle comprises a process consisting of at 94° C. (30 seconds)—45° C. (30 seconds)—72° C. (2 minutes). An amplified DNA fragment of about 250 bp was subcloned into plasmid vector pUC119, and its DNA sequence was determined. On the basis of the sequence determined, the primers F2S3 and F2S4, of which nucleotide sequences are shown in SEQ ID NOs: 23 and 24, respectively, in Sequence Listing, were then synthesized. PCR was carried out using these primers with the cosmid DNA prepared in Example 1 as a template, whereby selecting cosmid clones carrying the F2 gene. The PCR was carried out in a reaction mixture of the same composition as that used in Example 5(1) using Pfu DNA polymerase as an enzyme and 20 pmol each of the primers in 25 cycles, wherein one cycle comprises a process consisting of at 94° C. (30 seconds)—55° C. (30 seconds)—72° C. (2 minutes). As a result, there was found that Cosmid Clone No. 172 carries the F2 gene.

(2) Subcloning of F2 Gene

PCR was carried out using 20 pmol each of F2S3 and the cassette primer C2 or each of F2S4 and the cassette primer C2 as primers with 1 µl of each of the NheI/XbaI and XhoI/SalI cassette DNAs of Example 4 as a template. The PCR was carried out in a reaction mixture of the same composition as that used in Example 5(1) using Pfu DNA polymerase as an enzyme in 50 cycles, wherein one cycle comprises a process consisting of at 94° C. (30 seconds)—55° C. (30 seconds)—72° C. (3 minutes). As a result, each of amplified DNA fragments of about 700 bp and of about 1,400 bp for the NheI/XbaI and XhoI/SalI cassette DNAs, respectively, was amplified by the primer pair of F2S3 and the cassette primer C2, whereas no DNA was amplified by the primer pair of F2S4 and the cassette primer C2. This finding anticipated that the NheI and XhoI sites are located at a distance from the annealing position of the F2S4 primer unamplifiable with Pfu DNA polymerase.

With this in mind, the various DNA fragments obtained by digesting No. 172 with NheI were cut out, and each was subcloned into plasmid vector pTV118N (manufactured by Takara Shuzo Co., Ltd.). PCR was carried out using F2S3 and F2S4 as primers with each recombinant plasmid obtained as a template, to examine whether or not the F2 gene is present. As a result, it was found that an NheI fragment of about 8 kb carries the F2 gene. A plasmid resulting from insertion of this NheI fragment into pTV118N was named plasmid pF2172Nh. In addition, a restriction endonuclease map was prepared for the DNA insert in this plasmid. The results as shown in FIG. 5 were obtained.

Figure 5:
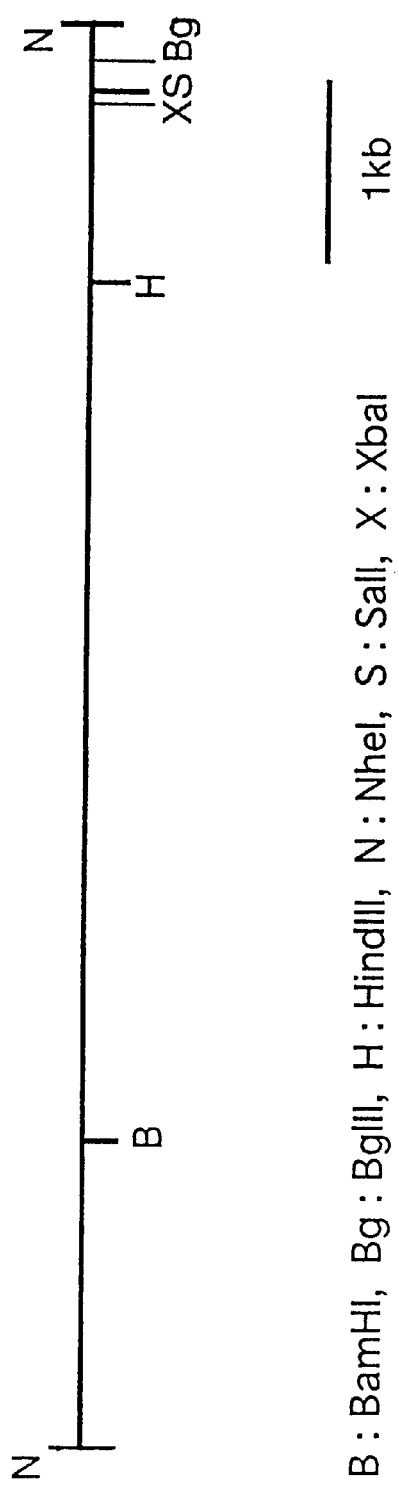
FIG. 5 is a restriction endonuclease map of a DNA insert of the plasmid pF2172Nh carrying a gene encoding the F2 protein.

On the basis of the restriction endonuclease map shown in FIG. 5, the plasmid pF2172Nh was digested with HindIII, and a HindIII fragment of about 1.5 kb was cut out, and each was subcloned into plasmid vector pTV118N. The recombinant plasmid obtained was examined for the insert orientation of the F2 gene, and there was found that the F2 gene was inserted in the reverse orientation with respect to the lac promoters of all of the vectors. This plasmid was named pF2172H16. *Escherichia coli* JM109/pF2172H16, *Escherichia coli* JM109 transformed with this plasmid, was examined for F2 expression, and found not to be highly expressed. With this in mind, in order to ligate the F2 gene in the orthodox orientation for the vector, pF2172H16 was digested with HindIII and EcoRI, and the HindIII-EcoRI fragment cut out was ligated to plasmid vector pTV119Nd (those resulting from substitution of the NcoI site with NdeI in plasmid vector pTV119N manufactured by Takara Shuzo Co., Ltd.). The recombinant plasmid obtained was named pF2172HE11, and *Escherichia coli* JM109 transformed with this plasmid was named *Escherichia coli* JM109/pF2172HE11.

(3) Preparation of F2 Authentic Sample *Escherichia coli* JM109/pF2172HE11 obtained in Example 6(2) was cultured for 16 hours in 2 liters of LB medium containing 1 mM IPTG and 100 μg/ml ampicillin. After harvesting, cells were suspended in 23.4 ml of sonication buffer, and 19.5 ml of a heat-treated supernatant was obtained in the same manner as Example 2(1). Next, this solution was applied to RESOURCE Q column, previously equilibrated with buffer D, and the applied solution was chromatographed using FPLC system. F2 flowed through RESOURCE Q column.

Twenty-two milliliters of the flow-through F2 fraction was applied to RESOURCE S column (manufactured by Pharmacia), previously equilibrated with buffer D. Using FPLC system, the elution was carried out on a linear concentration gradient of 0 to 500 mM NaCl, and an F2 fraction was eluted at 170 mM NaCl. This fraction was concentrated using Centricon-10, and 75 μl of the concentrate obtained was applied to Superdex 200 gel filtration column, previously equilibrated with 50 mM Tris-HCl buffer (pH 8.0) containing 2 mM 2-mercaptoethanol and 75 mM NaCl. The elution was carried out with the same buffer, and as a result, F2 was eluted at a position corresponding to a molecular weight of about 120 kilodaltons or about 45 kilodaltons. This molecular weight corresponds to the case where F2 has formed a hexamer or dimer.

(4) Determination of Nucleotide Sequence of DNA Fragment Carrying F2 Gene

The nucleotide sequence of the DNA insert in the above plasmid pF2172HE11 was determined by the dideoxy method. A sequence of 957 bp of the nucleotide sequence determined is shown in SEQ ID NO: 25 in Sequence Listing. As a result of analyzing the nucleotide sequence, there was found an open reading frame having the N-terminal amino acid sequence of F2. The nucleotide sequence of this open reading frame is shown in SEQ ID NO: 26 in Sequence Listing, and the amino acid sequence of the F2 translation product as deduced from the nucleotide sequence is shown in SEQ ID NO: 27 in Sequence Listing, respectively. This amino acid sequence was searched for homology to the amino acid sequences of known proteins, and as a result, the homologous proteins were not found.

Example 7

(1) Selection of Cosmid Clones Carrying F4 Gene

On the basis of the N-terminal amino acid sequence of F4 obtained in Example 3, the primers F4-1 and F4-2, of which nucleotide sequences are shown in SEQ ID NOs: 28 and 29, respectively, in Sequence Listing, were synthesized. First PCR was carried out using 100 pmol of the primer F4-1 and 20 pmol of the cassette primer C1 with 1 μl of the HindIII cassette DNA of Example 4 as a template. Second PCR was carried out using F4-2 and the cassette primer C2 with 1 μl of the reaction mixture as a template. The PCR was carried out in a reaction mixture of the same composition as that used in Example 5(1) using Pfu DNA polymerase as an enzyme in 30 cycles for the first PCR and 25 cycles for the second PCR, wherein one cycle comprises a process consisting of at 94° C. (30 seconds)—45° C. (30 seconds)—72° C. (2 minutes). An amplified DNA fragment of about 1,100 bp by this reaction was subcloned into plasmid vector pUC119, and a part of its nucleotide sequence was determined by the dideoxy method using M4 and RV primers (manufactured by Takara Shuzo Co., Ltd.). On the basis of the sequence determined, the primers F4S1 and F4S2, of which nucleotide sequences are shown in SEQ ID NOs: 30 and 31, respectively, in Sequence Listing, were then synthesized. PCR was carried out using these F4S1 and F4S2 primers with the cosmid DNA prepared in Example 1 as a template, whereby selecting cosmid clones carrying the F4 gene. The PCR was carried out in a reaction mixture of the same composition as that used in Example 5(1) using Pfu DNA polymerase as an enzyme in 30 cycles, wherein one cycle comprises a process consisting of at 94° C. (30 seconds)—55° C. (30 seconds)—72° C. (1 minute). As a result, it was found that Cosmid Clone Nos. 16, 26, 88, 112, 250, 269, 427 and 451 carry the F4 gene.

(2) Subcloning of F4 Gene

PCR was carried out using 20 pmol each of F4S2 and the cassette primer C2 with 1 μl of the XbaI cassette DNA of Example 4 as a template. The PCR was carried out in a reaction mixture of the same composition as that used in Example 5(1) using Pfu DNA polymerase as an enzyme in 50 cycles, wherein one cycle comprises a process consisting of at 94° C. (30 seconds)—55° C. (30 seconds)—72° C. (3 minutes). As a result, a DNA fragment of about 700 bp was amplified with F4S2 and the cassette primer C2. Also, PCR was carried out under the same conditions using F4-2 and the cassette primer C2 with HindIII cassette DNA as a template. As a result, a DNA fragment of about 1,100 bp was amplified. These findings suggested that the F4 gene is present in an XbaI-HindIII fragment of about 1.6 kb. With this in mind, Cosmid No. 16 was digested with XbaI and HindIII, and a DNA fragment of about 1.6 kb was cut out, and each was subcloned into pTV118N vector. PCR was carried out using the F4S1 and F4S2 primers with each recombinant plasmid obtained as a template, in order to examine for the presence of the F4 gene. As a result, a plasmid harboring a 1.6 kb XbaI-HindIII fragment carrying the F4 gene was obtained, and this plasmid was named plasmid pF4-1-4. Also, this plasmid was digested with the restriction enzymes NcoI, EcoRI, BamHI, PstI, SacI and NdeI. As a result, it was found that none of these sites were present in the above plasmid or DNA insert.

(3) Determination of Nucleotide Sequence of DNA Fragment Carrying F4 Gene

The nucleotide sequence of the DNA insert in the above plasmid pF4-1-4 was determined by the dideoxy method.

A sequence of 1,012 bp of the nucleotide sequence determined is shown in SEQ ID NO: 32 in Sequence Listing.

As a result of analyzing the nucleotide sequence, there was found an open reading frame having the N-terminal amino acid sequence of F4. The nucleotide sequence of this open reading frame is shown in SEQ ID NO: 33 in Sequence Listing, and the amino acid sequence of the F4 translation product as deduced from the nucleotide sequence is shown in SEQ ID NO: 34 in Sequence Listing, respectively. This amino acid sequence was searched for homology to the amino acid sequences of known proteins, and as a result, the homologous proteins were not found.

(4) Construction of Plasmid for F4 Expression

PCR was carried out in a reaction mixture of the same composition as that used in Example 5(1) with Pfu DNA polymerase using the primer F4NNd, of which nucleotide sequence is shown in SEQ ID NO: 35 in Sequence Listing, and the primer F4CEc, of which nucleotide sequence is shown in SEQ ID NO: 36 in Sequence Listing, with the plasmid pF4-1-4 described in Example 7(3) as a template. The reaction conditions are shown below. Using 1 ng of template DNA and 20 pmol each of the two primers, the reaction was carried out in 25 cycles, wherein one cycle comprises a process consisting of at 94° C. (30 seconds)—55° C. (30 seconds)—72° C. (2 minutes). An amplified DNA fragment of about 450 bp was digested with NdeI and EcoRI (both manufactured by Takara Shuzo Co., Ltd.), and the DNA fragment obtained was inserted between the NdeI and EcoRI sites of plasmid vector pTV119Nd mentioned above to prepare the plasmid pF4Nd-6. Furthermore, the nucleotide sequence of the DNA insert in the plasmid was determined by the dideoxy method. It was confirmed that there is no mutation caused by PCR.

(5) Preparation of Purified F4 Authentic Sample

*Escherichia coli* JM109/p4Nd-6, *Escherichia coli* JM109 transformed with the plasmid pF4Nd-6 obtained in Example 7(4), was cultured for 16 hours in 2 liters of LB medium containing 100 μg/ml ampicillin. After harvesting, cells were suspended in 33.4 ml of sonication buffer, and 28 ml of a heat-treated supernatant was obtained in the same manner as Example 2(1). Next, this solution was applied to RESOURCE Q column, previously equilibrated with buffer D, and the applied solution was chromatographed using FPLC system. The elution was carried out on a linear concentration gradient of 0 to 500 mM NaCl. F4 was eluted at a concentration of 325 mM NaCl.

Three milliliters of the solution obtained by collecting the F4 fraction was subjected to exchange with buffer D containing 150 mM NaCl using PD-10 column, and 6.9 ml of the solution was applied to HiTrap Heparin column, previously equilibrated with the same buffer. F4 was not adsorbed to HiTrap Heparin column, and $(NH_4)_2SO_4$ was added to 7.2 ml of the F4 fraction flowed through the column so as to have a final concentration of 1 M. This solution was applied to HiTrap Phenyl column (manufactured by Pharmacia), previously equilibrated with buffer D containing 1 M $(NH_4)_2SO_4$. Using FPLC system, the column was washed with each of 1 M and 0.5 M $(NH_4)_2SO_4$, and thereafter F4 was eluted with buffer D. Five milliliters of this fraction was concentrated using Centricon-10, and 76 μl of the concentrate obtained was applied to Superdex 200 gel filtration column, previously equilibrated with 50 mM Tris-HCl buffer, pH 8.0, containing 2 mM 2-mercaptoethanol and 75 mM NaCl. As a result of the elution with the same buffer, F4 was eluted at a position corresponding to a molecular weight of about 39 kilodaltons. This molecular weight corresponds to the case where F4 has formed a dimer or trimer.

Example 8

(1) Selection of Cosmid Clones Carrying F7 Gene

On the basis of the N-terminal amino acid sequence of F7 obtained in Example 3, the primers F7-1 and F7-2, of which nucleotide sequences are shown in SEQ ID NOs: 37 and 38, respectively, in Sequence Listing, were synthesized. First PCR was carried out using 100 pmol of F7-1 and 20 pmol of the cassette primer C1 with 1 μl of the HindIII cassette DNA prepared in Example 4 as a template. Second PCR was carried out using 100 pmol of the primer F7-2 and 20 pmol of the cassette primer C2 with 1 μl of the reaction mixture obtained as above as a template. The PCR was carried out using the same reaction mixture composition and reaction conditions as those used in Example 6(1). An amplified DNA fragment of about 830 bp was subcloned into plasmid vector pUC119, and its nucleotide sequence was determined. On the basis of the sequence determined, the primers F7S1 and F7S2, of which nucleotide sequences are shown in SEQ ID NOs: 39 and 40, respectively, in Sequence Listing, were then synthesized. PCR was carried out using these primers with the cosmid DNA described in Example 1 as a template, whereby selecting cosmid clones carrying the F7 gene. The PCR was carried out in a reaction mixture of the same composition as that used in Example 5(1) using Pfu DNA polymerase as an enzyme in 30 cycles, wherein one cycle comprises a process consisting of at 94° C. (30 seconds)—55° C. (30 seconds)—72° C. (3 minutes). As a result, there was found that Cosmid Clone Nos. 15, 96, 114, 167, 277, 348, 386, 400, 419, 456, 457 and 484 carry the F7 gene.

(2) Subcloning of F7 Gene

Figure 6:
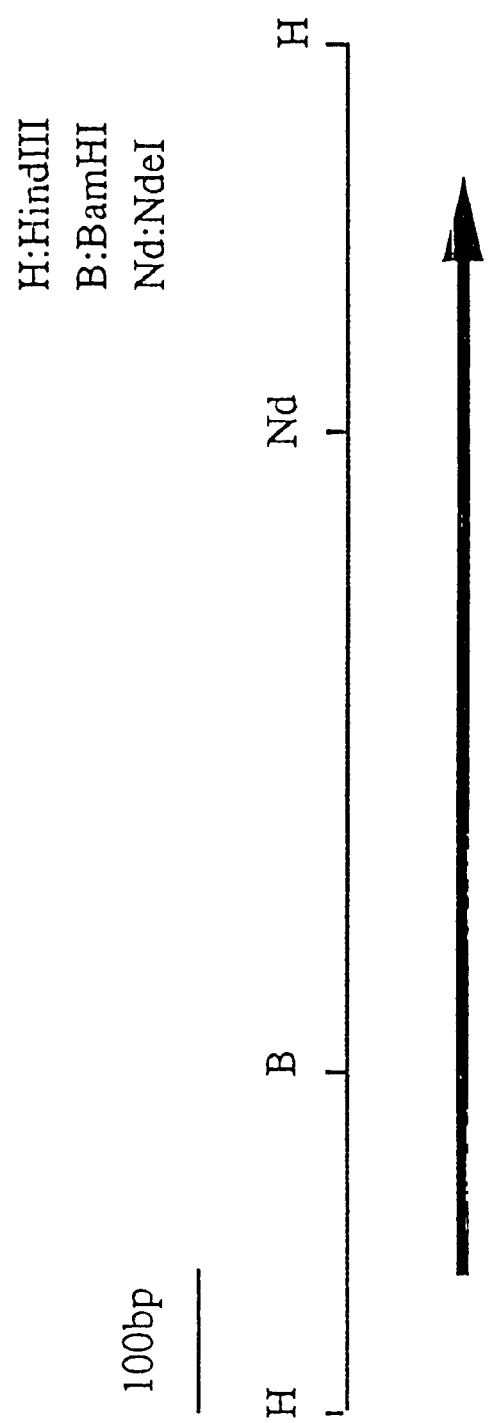
FIG. 6 is a restriction endonuclease map of a DNA insert of the plasmid pF7-1-8 carrying a gene encoding the F7 protein.

PCR was carried out using 20 pmol each of F7S2 and the cassette primer C2 with 1 μl of the HindIII cassette DNA prepared in Example 4 as a template. The PCR was carried out in a reaction mixture of the same composition as that used in Example 5(1) using Pfu DNA polymerase as an enzyme in 50 cycles, wherein one cycle comprises a process consisting of at 94° C. (30 seconds)—55° C. (30 seconds)—72° C. (3 minutes). As a result, a fragment of about 900 bp was amplified. From this result, together with the result of amplification using F7-2 of Example 8(1) and the cassette primer C2, the presence of the F7 gene in a HindIII fragment of about 1.0 kb was anticipated. With this in mind, No. 15, randomly selected from the cosmids carrying that gene, was digested with HindIII, and a DNA fragment of around 1.0 kb was cut out, and each was subcloned into plasmid vector pTV118N. PCR was carried out using the F7S1 and F7S2 primers with each recombinant plasmid obtained as a template, to examine for the presence of the F7 gene, and as a result, it was found that a HindIII fragment of 1 kb carries the F7 gene. A plasmid in which the F7 gene in this DNA fragment was ligated to downstream of the lac promoter of pTV118N vector was named pF7-HH-18, and a plasmid in which the F7 gene was ligated in the opposite orientation was named pF7-1-8. Also, a restriction endonuclease map was prepared for the DNA insert contained in this plasmid, and the map as shown in FIG. 6 was obtained.

(3) Determination of Nucleotide Sequence of DNA Fragment Carrying F7 Gene

There was determined by the dideoxy method the nucleotide sequence of each insert in the above two kinds of plasmids, each insert in the plasmids being prepared by cutting out the BamHI-HindIII, NdeI-HindIII, HindIII-NdeI and HindIII-BamHI fragments from the above two kinds of plasmids, and subcloning the fragments into plasmid vector pTV119Nd. A sequence of 989 bp of the nucleotide sequence of the DNA insert of the above plasmid, determined on the basis of these overall results, is shown in SEQ ID NO: 41 in Sequence Listing. As a result of analyzing the nucleotide sequence, there was found an open reading frame containing the N-terminal amino acid sequence of F7. The nucleotide sequence of this open reading frame is shown in SEQ ID NO: 2 in Sequence Listing, and the amino acid sequence of the F7 translation product as deduced from the nucleotide sequence is shown in SEQ ID NO: 1 in Sequence Listing. This amino acid sequence was searched for homology to the amino acid sequences of known proteins, and as a result, it was found that the amino acid sequence was homologous to the proliferating cell nuclear antigen (PCNA) involved in the DNA replication in eukaryotes [*EMBO J.*, 11, 5111–5120 (1995); *Nucleic Acids Research*, 18, 261–265 (1990); *Proc. Natl. Acad. Sci. USA*, 84, 1575–1579 (1987)]. The homology to the proteins described in the individual references were 24, 28 and 24%, respectively.

(4) Preparation of Purified F7 Authentic Sample

*Escherichia coli* JM109/pF7-HH-18, *Escherichia coli* JM109 transformed with the plasmid pF7-HH-18 obtained in Example 8(2), was cultured for 16 hours in 2 liters of LB medium containing 100 μg/ml ampicillin. After harvesting, cells were suspended in 45 ml of sonication buffer, and 41.9 ml of a heat-treated supernatant was obtained in the same manner as Example 2(1). Next, this solution was thrice subjected to 2-hour dialysis against 2 liters of buffer A as a dialysate. After dialysis, 36 ml of the enzyme solution was applied to RESOURCE Q column, previously equilibrated with buffer A, and the applied solution was chromatographed using FPLC system. The elution was carried out on a linear concentration gradient of 0 to 500 mM NaCl. As a result, F7 was eluted at 340 mM NaCl.

Ten milliliters of the solution obtained by collecting the F7 fraction was concentrated using Centriflow CF-50, and thereafter subjected to exchange with buffer A containing 1 M $(NH_4)_2SO_4$ using PD-10 column, and 3.5 ml of the solution obtained was applied to HiTrap Phenyl column, previously equilibrated with the same buffer. Using FPLC system, the column was sequentially washed with 1 M and 0.5 M $(NH_4)_2SO_4$, and thereafter F7 was eluted with buffer A. Four milliliters of this fraction was concentrated using Centricon-10, and 80 μl of this concentrate was applied to Superdex 200 gel filtration column, previously equilibrated with 50 mM potassium phosphate buffer (pH 6.5) containing 2 mM 2-mercaptoethanol and 75 mM NaCl. As a result of elution with the same buffer, F7 was eluted at a position corresponding to a molecular weight of about 99 kilodaltons. This molecular weight corresponds to the case where F7 has formed a trimer.

(5) Effects of F7 on Primer Extension Reactions

In order to examine for the effects of F7 on the primer extension reactions to various polymerases, the activities of Pfu polymerase C, Pfu DNA polymerase (α-type DNA polymerase, manufactured by STRATAGENE) and *Pyrodictium occultum*-derived Poc DNA polymerases I and II [Poc DNA polymerases I and II, *J. Bacteriol.*, 177, 2164–2177 (1995)] were compared with regard to the presence or absence of the addition of F7.

Determination of DNA polymerase activities were carried out with reference to the Pfu polymerase C activity determination described in Example 2(1). The substrate used was the constructs (M13-HT primer) as prepared by annealing the HT primer, a synthetic oligonucleotide having 45 bases, to M13 phage single-stranded DNA (M13 mp18 ssDNA, manufactured by Takara Shuzo Co., Ltd.). The nucleotide sequence of the HT primer is shown in SEQ ID NO: 42 in Sequence Listing.

Concretely, a reaction mixture [20 mM Tris-HCl, pH 7.7, 15 mM $MgCl_2$, 2 mM 2-mercaptoethanol, 0.01 μg/μl M13-HT primer, 40 μM each of dATP, dCTP, dGTP and dTTP, 60 nM [$^3$H]-dTTP (manufactured by Amersham)] making up a final volume of 50 μl and containing each DNA polymerase listed in Table 2 and F7 was prepared and reacted at 75° C. for 5 minutes. After the reaction mixture was cooled with ice to stop the reaction, a 40 μl portion was spotted onto DE paper (manufactured by Whatman) and washed 5 times with 5% $Na_2HPO_4$, and thereafter the remaining radioactivity on the DE paper was determined using a liquid scintillation counter.

As shown in Table 2, for all the DNA polymerases used, an increase in DNA polymerase activity due to the addition of F7 was observed.

TABLE 2

| DNA Polymerase | | F7 | Enzyme Activity (cpm) |
|---|---|---|---|
| Blank 1 | | — | 61 |
| Blank 2 | | 10 pmol | 35 |
| Pfu Polymerase C | (25 fmol) | — | 888 |
| Pfu Polymerase C | (25 fmol) | 5 pmol | 2897 |
| Pfu Polymerase C | (25 fmol) | 10 pmol | 3175 |
| Pfu DNA Polymerase | (120 fmol) | — | 907 |
| Pfu DNA Polymerase | (120 fmol) | 0.48 pmol | 1363 |
| Pfu DNA Polymerase | (120 fmol) | 4.8 pmol | 1637 |
| Poc DNA Polymerase I | (74 pmol) | — | 62 |
| Poc DNA Polymerase I | (74 pmol) | 10 pmol | 69 |
| Poc DNA Polymerase II | (6.0 pmol) | — | 433 |
| Poc DNA Polymerase II | (6.0 pmol) | 10 pmol | 1443 |

Note:
In the table, the amount of Pfu polymerase C is the amount of a protein comprising one molecule each of the two DNA polymerase-constituting proteins, and the amount of F7 is the amount as a trimer protein.

Primer extension activity was further studied in detail. The M13-HT primer, previously labeled at the 5'-terminus of the primer using [γ-$^{32}$P]-ATP (manufactured by Amersham) and T4 polynucleotide kinase (manufactured by Takara Shuzo Co., Ltd.), was used as a substrate.

A 1 μl sample solution containing each of the following samples was prepared: 1) 18 fmol of Pfu polymerase C, 2) 18 fmol of Pfu polymerase C+2 pmol of F7, 3) 0.24 pmol of Pfu DNA polymerase, 4) 0.24 pmol of Pfu DNA polymerase+0.78 pmol of F7. To each sample solution, 9 μl of a reaction mixture [20 mM Tris-HCl (pH 9.0), 15 mM $MgCl_2$, 2 mM 2-mercaptoethanol, 40 μM each of dATP, dGTP, dCTP and dTTP] containing 0.01 μg/μl $^{32}$P-labeled M13-HT primer was added, and a reaction was carried out at 75° C. for 2.5 minutes or 5 minutes. After termination of the reaction, the reaction mixture was cooled with ice to stop the reaction, and 1 μl of 200 mM EDTA and 5.5 μl of a reaction stop solution (95% formamide, 20 mM EDTA, 0.05% bromophenol blue, 0.05% xylene cyanol) were added, and thermal denaturation treatment was carried out at 95° C. for 5 minutes. After 1.6 μl of this reaction mixture was electrophoresed using 6% polyacrylamide gel containing 8 M urea, an autoradiogram was prepared. The autoradiogram obtained is shown in FIG. 7.

In the figure, Pfu-C and pfu show the results obtained with Pfu polymerase C and Pfu DNA polymerase, respectively, and 2.5 and 5 show the respective reaction time (minutes). In addition, the symbols – and + in the figure show the results obtained with the reaction mixture in the absence and presence of F7, respectively. Further, the lanes on both ends of the figure show the results of electrophoresis of λ-EcoT14I digest (manufactured by Takara Shuzo Co., Ltd.), previously labeled at the 5'-terminus using [γ-$^{32}$P]-ATP (manufactured by Amersham) and T4 polynucleotide kinase (manufactured by Takara Shuzo Co., Ltd.), and were used to deduce the lengths of the extension products.

Figure 7:
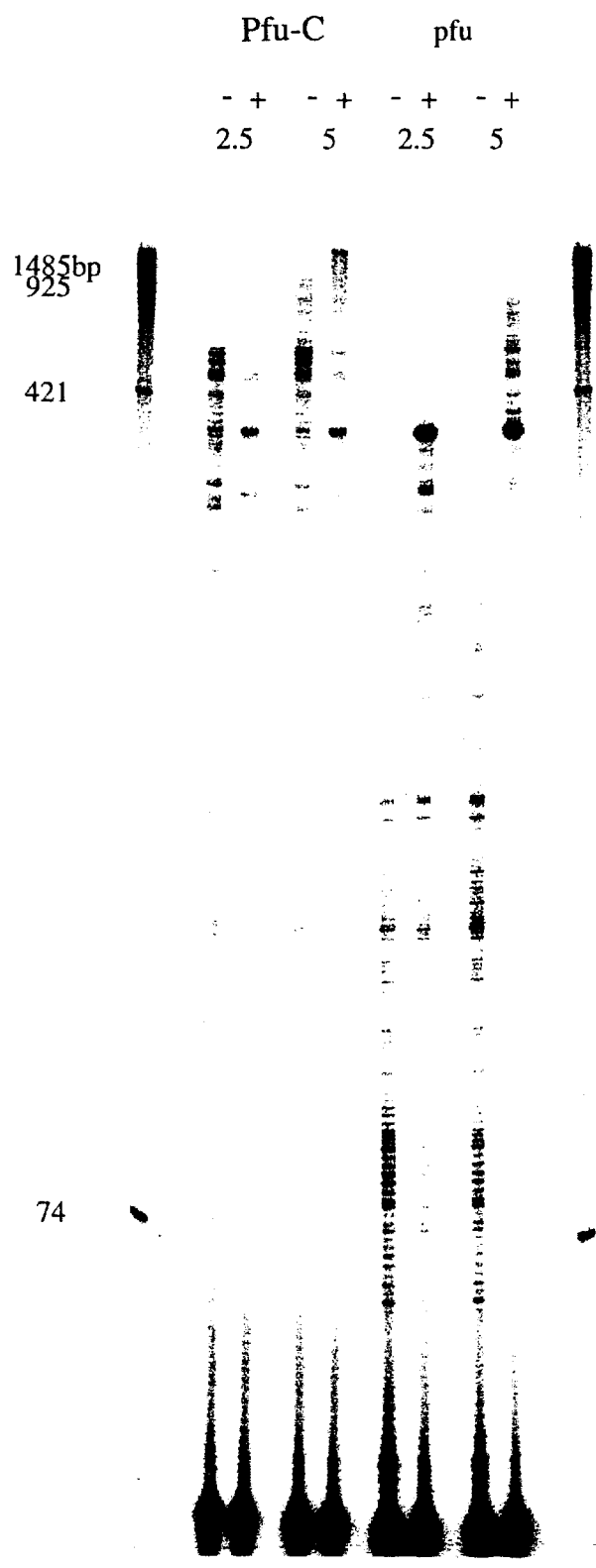
FIG. 7 is an autoradiogram showing a primer extension activity of the DNA polymerase when the F7 protein is added.

As shown in FIG. 7, when F7 is not added, in Pfu polymerase C, DNAs of about 300 to 600 bases are the major extension products obtained, whereas when F7 is added, extension products of low chain length decreases and the ratio of extension products exceeding 1,000 bases increases. Also in Pfu DNA polymerase, the chain length of extension products was markedly extended by the addition of F7. It was thus elucidated that F7 increases the primer extension rates of both Pfu polymerase C and Pfu DNA polymerase.

Figure 8:
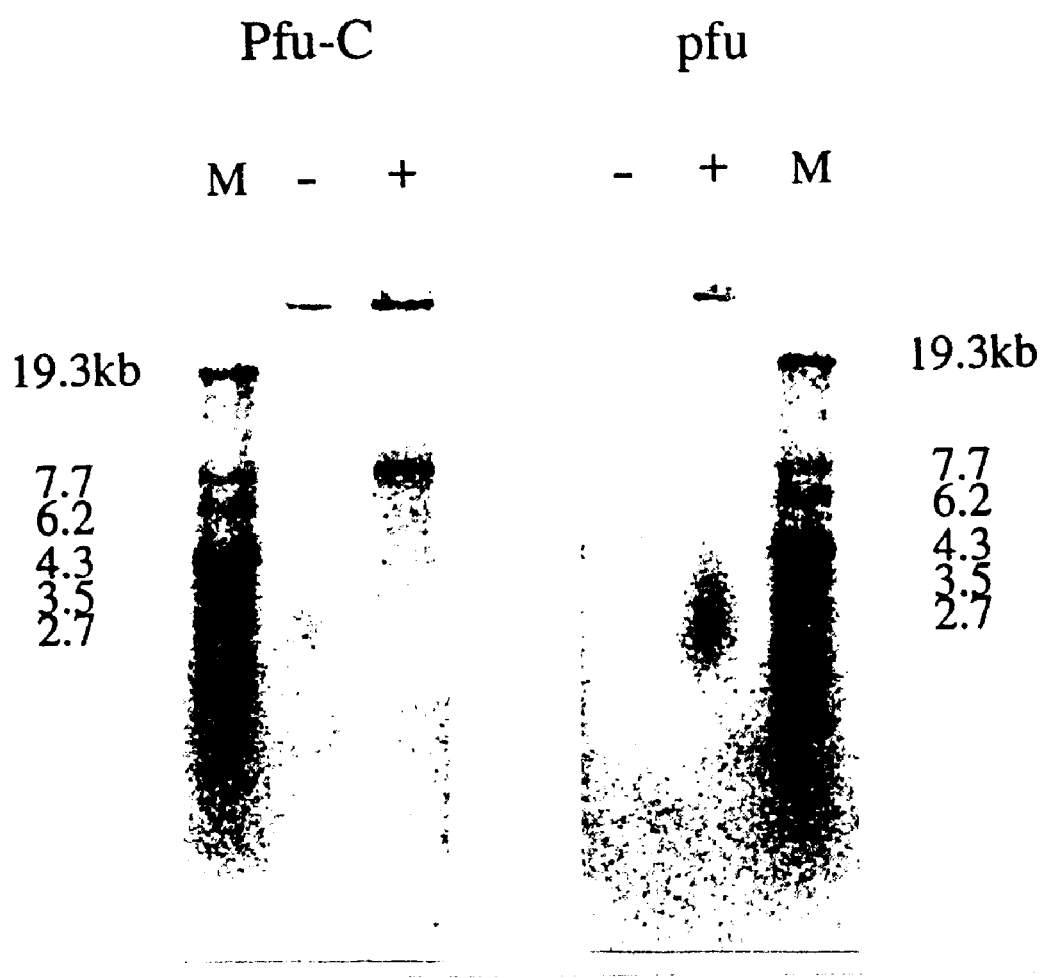
FIG. 8 is an autoradiogram showing a primer extension activity for the higher molecular primer extension reaction product of the DNA polymerase, when the F7 protein is added.

Next, in order to analyze primer extension reaction products of higher molecular weights, the primer extension reaction products of Pfu polymerase C and Pfu DNA polymerase with the $^{32}$P-labeled M13-HT primer as a substrate were analyzed by alkaline agarose gel electrophoresis. To 1 μl of a solution of each of samples 1) to 4) above, 9 μl of a reaction mixture (20 mM Tris-HCl, pH 9.0, 15 mM MgCl$_2$, 2 mM 2-mercaptoethanol, 40 μM each of dATP, dGTP, dCTP and dTTP, 84 nM [α-$^{32}$P]-dCTP) was added so as to have a final concentration of 0.01 μg/μl M13-HT primer, and a reaction was carried out at 75° C. for 2.5 minutes. After termination of the reaction, to the ice cooled reaction mixture, 1.11 μl of 200 mM EDTA, 1.23 μl of 500 mM NaOH and 2.47 μl of 6-fold concentrated loading buffer (0.125% bromophenol blue, 0.125% xylene cyanol, 9% glycerol) were sequentially added. After 6 μl of this mixture was electrophoresed using 0.5% alkaline agarose gel, an autoradiogram was prepared. The autoradiogram obtained is shown in FIG. 8.

In the figure, Pfu-C and pfu show the results obtained with Pfu polymerase C and Pfu DNA polymerase, respectively, and the symbols − and + in the figure show the results obtained without or with addition of F7, respectively. Further, in the figure, Lane M is for the λ-EcoT14I digest, previously labeled at one end in the same manner as above. As shown in FIG. 8, in the case of Pfu polymerase C, a weak extension product signal was observed near 2.5 kb in the absence of F7, whereas a 7.3 kb signal completely encircling M13 ssDNA was observed in the presence of F7. In addition, in the case of Pfu DNA polymerase, a signal was observed near 2.7 kb in the presence of F7, whereas no signal was observed in the absence of F7. These findings demonstrate that F7 enhances the extension reactions of the two DNA polymerases.

Example 9

(1) Selection of Cosmid Clones Carrying Gene Encoding Homologs of RFC Small Subunit Regarding the amino acid sequence of the RFC small subunit of *Methanococcus jannaschii* [*Science*, 273, 1058–1073 (1996)], homology to the amino acid sequences of RFC (RF-C) small subunits derived from other organisms was examined. On the basis of the amino acid sequences of regions highly conserved thereamong, the primers RF-F1, RF-F3, RF-F4, RF-R1, RF-R2, RF-R3 and RF-R4 for searching the gene encoding the RFC small subunit were synthesized. The nucleotide sequences of these primers are shown in SEQ ID NOs: 43 to 49, respectively, in Sequence Listing. PCR was carried out using various combinations of these primers with *Pyrococcus furiosus* genomic DNA as a template, whereby searching for the gene encoding the RFC small subunit. The PCR was carried out in a reaction mixture of the same composition as that used in Example 5(1) using Pfu DNA polymerase, and using 0.25 μg of template DNA and 100 pmol of each primer. When first PCR was carried out using RF-F1 and RF-R4, second PCR was carried out using RF-F4 and RF-R4, or RF-F1 and RF-R1, with 1 μl of the reaction mixture as a template. When first PCR was carried out using RF-F1 and RF-R3, second PCR was carried out using RF-F3 and RF-R2 with 1 μl of the reaction mixture as a template. Amplified DNA fragments of about 240 bp, about 140 bp and about 140 bp, respectively, were obtained. Each of these DNA fragments was subcloned into plasmid vector pUC119, and its nucleotide sequence was determined. On the basis of the sequences determined, the primers RF-S1, RF-S2, RF-S3, RF-S4 and RF-S5, of which nucleotide sequences are shown in SEQ ID NOs: 50 to 54, respectively, in Sequence Listing, were then synthesized. PCR was carried out using these RF-S1 and RF-S3 primers with the cosmid DNA prepared in Example 1 as a template, whereby selecting cosmid clones assumed to carry the gene encoding homologs of the RFC small subunit. The PCR was carried out using the TaKaRa PCR amplification kit in 25 cycles, wherein one cycle comprises a process consisting of at 94° C. (30 seconds)—55° C. (30 seconds)—72° C. (2 minutes). As a result, there was found that Cosmid Clone Nos. 254, 310, 313, 377 and 458 carry the desired gene (PFU-RFC gene).

(2) Subcloning of PFU-RFC Gene

PCR was carried out using 100 pmol of RF-S1 and 20 pmol of the cassette primer C2, or 100 pmol of RF-S2 and 20 pmol of the cassette primer C2, with 1 μg each of the XbaI and EcoRI cassette DNAs prepared in Example 4 as a template. The PCR was carried out in a reaction mixture of the same composition as that used in Example 6(1) using the Pfu polymerase C enzyme in 50 cycles, wherein one cycle comprises a process consisting of at 94° C. (30 seconds)—55° C. (30 seconds)—72° C. (3 minutes). As a result, a DNA fragment of about 2 kb was amplified by RF-S1 and the cassette primer C2 when the XbaI cassette was used as a template, and a DNA fragment of about 1.5 kb was amplified by RF-S2 and the cassette primer C2 when the EcoRI cassette was used as a template. Each of these DNA fragments was subcloned into plasmid vector pUC119, and the recombinant plasmids obtained were named pRFSXS1-26 and pRFSES2-8. Restriction endonuclease maps of these plasmids were prepared, and as a result, it was anticipated that neither NdeI nor BamHI site is present in the PFU-RFC gene.

Figure 9:
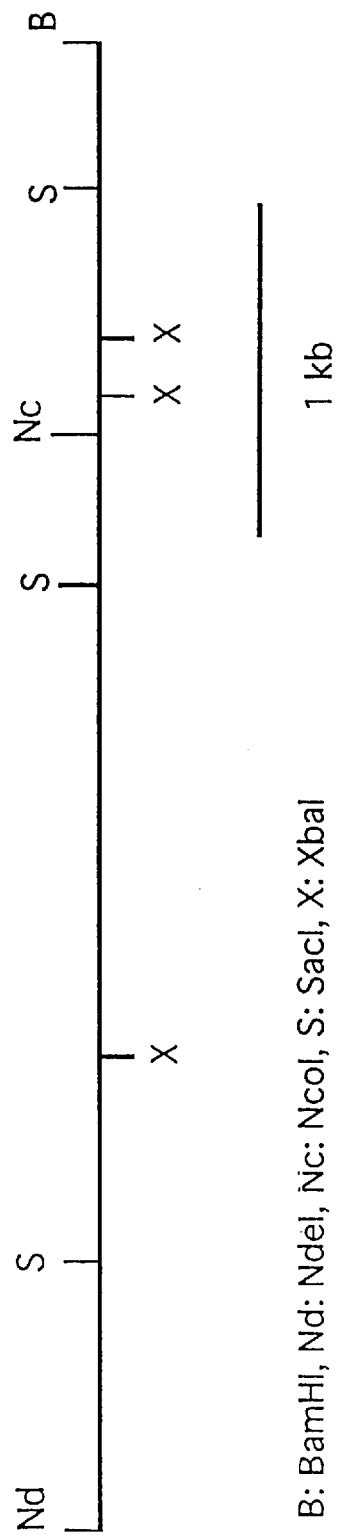
FIG. 9 is a restriction endonuclease map of a DNA insert of the plasmid pRFS254NdB carrying a gene encoding the PFU-RFC protein.

The cosmids of the five clones mentioned in (1) above were each digested with NdeI and BamHI, and the electrophoretic patterns were examined. As a result, a common band was observed near 5 kb. Anticipating the presence of the PFU-RFC gene in this DNA fragment, an NdeI-BamHI fragment of about 5 kb from Clone No. 254 was cut out, and each was subcloned into pTV119Nd vector mentioned above. A transformant formed with the recombinant plasmid obtained was examined for the presence PFU-RFC gene by PCR using the RF-S1 and RF-S3 primers. As a result, there was found that this NdeI-BamHI fragment carry the PFU-RFC gene. Therefore, the plasmid resulting from insertion of this NdeI-BamHI fragment into pTV119Nd vector was named plasmid pRFS254NdB. In addition, a restriction endonuclease map of this plasmid was prepared, and the map as shown in FIG. 9 was obtained.

On the basis of the restriction endonuclease map shown in FIG. 9, various fragments were cut out from pRFS254NdB by the method described below, and each was subcloned into pTV118N vector (manufactured by Takara Shuzo Co., Ltd.). First, a DNA fragment of about 500 bp obtained by digesting pRFS254NdB with XbaI and SacI, a DNA fragment of about 2 kb obtained by digesting with XbaI and NcoI, and a DNA fragment of about 1.1 kb obtained by digesting with NcoI and BamHI was prepared, respectively, and each was mixed with pTV118N, previously linearized with SacI and BamHI, for ligation, whereby constructing a recombinant plasmid. This plasmid was named pRFS254SXNB.

(3) Determination of Nucleotide Sequence of DNA Fragment Carrying PFU-RFC Gene

The nucleotide sequence of the DNA insert in the plasmid pRFS254NdB obtained in Example 9(2) was determined by the dideoxy method. A sequence of 3,620 base pairs of the nucleotide sequence determined is shown in SEQ ID NO: 55 in Sequence Listing. The amino acid sequence of the protein encoded by this nucleotide sequence was deduced. As a result of comparing this amino acid sequence with those of known RFC small subunits, there was anticipated the presence of one intein in the amino acid sequence of PFU-RFC. This intein is encoded by Nos. 721 to 2295 of SEQ ID NO: 55 in Sequence Listing.

(4) Construction of Intein-Eliminated PFU-RFC Expression Plasmid

On the basis of the nucleotide sequence determined in Example 9(3), and the amino acid sequence of a known RFC small subunit and the nucleotide sequence of the gene encoding the subunit, the primers RF-CBΔI and RF-CAΔI, of which nucleotide sequences are shown in SEQ ID NOs: 56 and 57 in Sequence Listing, were synthesized. Inverse PCR was carried out using these two primers, each of which 5'-terminus was previously phosphorylated, with the above plasmid pRFS254SXNB as a template. For inverse PCR, TaKaRa Ex Taq was used to prepare 100 µl of a reaction mixture in accordance with the instructions for the enzyme. To this reaction mixture added with 15 ng of the plasmid pRFS254SXNB and 20 pmol each of the primers, the reaction was carried out in 30 cycles, wherein one cycle comprises a process consisting of at 94° C. (30 seconds)—55° C. (30 seconds)—72° C. (3 minutes). An amplified DNA fragment obtained by the inverse PCR was blunt-ended using DNA blunting kit (manufactured by Takara Shuzo Co., Ltd.), and thereafter subjected to self-ligation, whereby constructing a plasmid, which was named the plasmid pRFS254ISΔI.

Furthermore, an XbaI-NcoI fragment of about 400 bp isolated after digestion of the plasmid with XbaI and NcoI was mixed with and an XbaI-SacI fragment of about 500 bp and an NcoI-BamHI fragment of about 1.1 kb, each isolated from the plasmid pRFS254NdB obtained in Example 9(2), and the mixed fragments were subcloned between the BamHI and SacI sites of plasmid vector pTV118N. The recombinant plasmid obtained as described above was named pRFS254SNc. *Escherichia coli* JM109 transformed with the plasmid was named *Escherichia coli* JM109/pRFS254SNc. It was found that the transformant expresses PFU-RFC at high level.

(5) Determination of Nucleotide Sequence of Gene Encoding PFU-RFC Without Carrying Intein An XbaI-NcoI fragment of about 400 bp derived from the plasmid pRFS254SXNB obtained in Example 9(4) was subcloned into plasmid vector pTV118N, and the nucleotide sequence of the DNA insert was determined, whereby the nucleotide sequence encoding the boundary portion of the intein eliminated was confirmed. From this result and the results of Example 9(3), the nucleotide sequence of the gene encoding PFU-RFC without carrying intein was determined. The nucleotide sequence of the open reading frame encoding PFU-RFC without carrying intein obtained as described above and the amino acid sequence of PFU-RFC deduced from the nucleotide sequence are shown in SEQ ID NOs: 4 and 3, respectively, in Sequence Listing.

(6) Preparation of Purified PFU-RFC Authentic Sample

*Escherichia coli* JM109/pRFS254Nc obtained in Example 9(4) was cultured for 16 hours in 2 liters of LB medium containing 100 µg/ml ampicillin. After harvesting, cells were suspended in 44.1 ml of sonication buffer, and 35.2 ml of a heat-treated supernatant was obtained in the same manner as Example 2(1). Next, this solution was applied to RESOURCE Q column, previously equilibrated with buffer D, and the applied solution was chromatographed using FPLC system. PFU-RFC was flowed through RESOURCE Q column.

Thirty-five milliliters of the flow-through PFU-RFC fraction was applied to RESOURSE S column (manufactured by Pharmacia), previously equilibrated with buffer D. Using FPLC system, the elution was carried out on a linear concentration gradient of 0 to 500 mM NaCl to yield a PFU-RFC fraction eluted at 170 mM NaCl. 2.9 ml Of this fraction was concentrated using Centricon-10, and 105 µl of the concentrate obtained was applied to Superdex 200 gel filtration column, previously equilibrated with 50 mM Tris-HCl buffer, pH 8.0, containing 2 mM 2-mercaptoethanol and 75 mM NaCl. The elution was carried out with the same buffer, and as a result, PFU-RFC was eluted at a position corresponding to a molecular weight of about 150 kilodaltons. This molecular weight corresponds to the case where PFU-RFC has formed a tetramer.

(7) Effects of PFU-RFC on Primer Extension Reaction

The effects of PFU-RFC and F7 on the primer extension reaction by Pfu polymerase C were examined in the same manner as Example 8(5). The results are shown in Table 3. As shown in Table 3, PFU-RFC slightly enhanced the activity of Pfu polymerase C. Furthermore, in the case where PFU-RFC was added simultaneously with F7, the enhanced activity more than doubled than the case where F7 was added alone.

TABLE 3

| Pfu Polymerase C | F7 | PFU-RFC | Enzyme Activity (cpm) |
|---|---|---|---|
| — | — | — | 100 |
| 90 fmol | — | — | 366 |
| 90 fmol | 9.6 pmol | — | 2743 |
| 90 fmol | — | 356 fmol | 463 |
| 90 fmol | 9.6 pmol | 356 fmol | 8740 |

Note:
In the table, the amount of Pfu polymerase C is the amount as a protein comprising one molecule each of the two DNA polymerase-constituting proteins, and the amounts of F7 and PFU-RFC are the amounts as a trimer and tetramer proteins, respectively.

Example 10

(1) Preparation of Anti-Pfu DNA Polymerase Antibody

Twelve milliliters (30,000 units) of cloned Pfu DNA polymerase (manufactured by STRATAGENE) was concentrated by ultrafiltration using Centricon-10, and thereafter 0.1 ml of the concentrate obtained was applied to Superdex 200 gel filtration column (manufactured by Pharmacia), previously equilibrated with 50 mM Tris-HCl (pH 8.0) containing 2 mM 2-mercaptoethanol and 75 mM NaCl. The elution was carried out with the same buffer, and a Pfu DNA polymerase fraction eluted at a position corresponding to a molecular weight of about 76 kilodaltons was recovered. After 0.8 ml of this fraction was concentrated using Centricon-10, this concentrate was used as an antigen to prepare an anti-Pfu DNA polymerase polyclonal antibody. The above concentrate was diluted with physiological saline so as to have a Pfu DNA polymerase concentration of 2 mg/ml, and the diluted solution was emulsified with an equal volume of Freund's complete adjuvant. This emulsion was subcutaneously injected to rabbits at 250 µl per injection four times at 3-week intervals. Ten days after final immunization, whole blood was extracted. After allowing to stand at room temperature for 60 minutes, the extracted blood was centrifuged to yield 60 ml of an antiserum containing the anti-Pfu DNA polymerase polyclonal antibody. To 26 ml of this antiserum, 26 ml of a saturated solution of ammonium sulfate was added, and the mixture was gently stirred at 4° C. for 1 hour and 45 minutes, and subsequently centrifuged. The precipitate was suspended in 5 ml of 20 mM sodium phosphate buffer (pH 7.0) and desalted using PD-10 column (manufactured by Pharmacia), previously equilibrated with the same buffer. Ten milliliters of this solution was applied to Protein A column (manufactured by Pharmacia), previously equilibrated with 20 mM sodium phosphate buffer (pH 7.0). After the column was washed with the same buffer, the elution was carried out with 0.1 M sodium citrate buffer (pH 3.0). The eluted fraction containing the anti-Pfu DNA polymerase polyclonal antibody was neutralized with 1 M Tris-HCl, pH 9.0, and thereafter the mixture was concentrated using Centriflow CF-50 and subjected to exchange with coupling buffer (0.5 M NaCl, 0.2 M NaHCO$_3$, pH 8.3) using PD-10 column to prepare a solution containing the anti-Pfu DNA polymerase antibody.

(2) Preparation of Anti-Pfu DNA Polymerase Antibody Column

HiTrap NHS-activated column (manufactured by Pharmacia) was washed with 6 ml of 1 mM HCl, and thereafter 0.9 ml of the above anti-Pfu DNA polymerase polyclonal antibody solution (containing 4.5 mg equivalent of the anti-Pfu DNA polymerase antibody) was applied. Subsequently, an anti-Pfu DNA polymerase antibody column was prepared in the same manner as Example 2(3).

(3) Confirmation of Formation of Complex of Pfu DNA Polymerase and F7 Using Anti-Pfu DNA Polymerase Antibody Column

Figure 10:
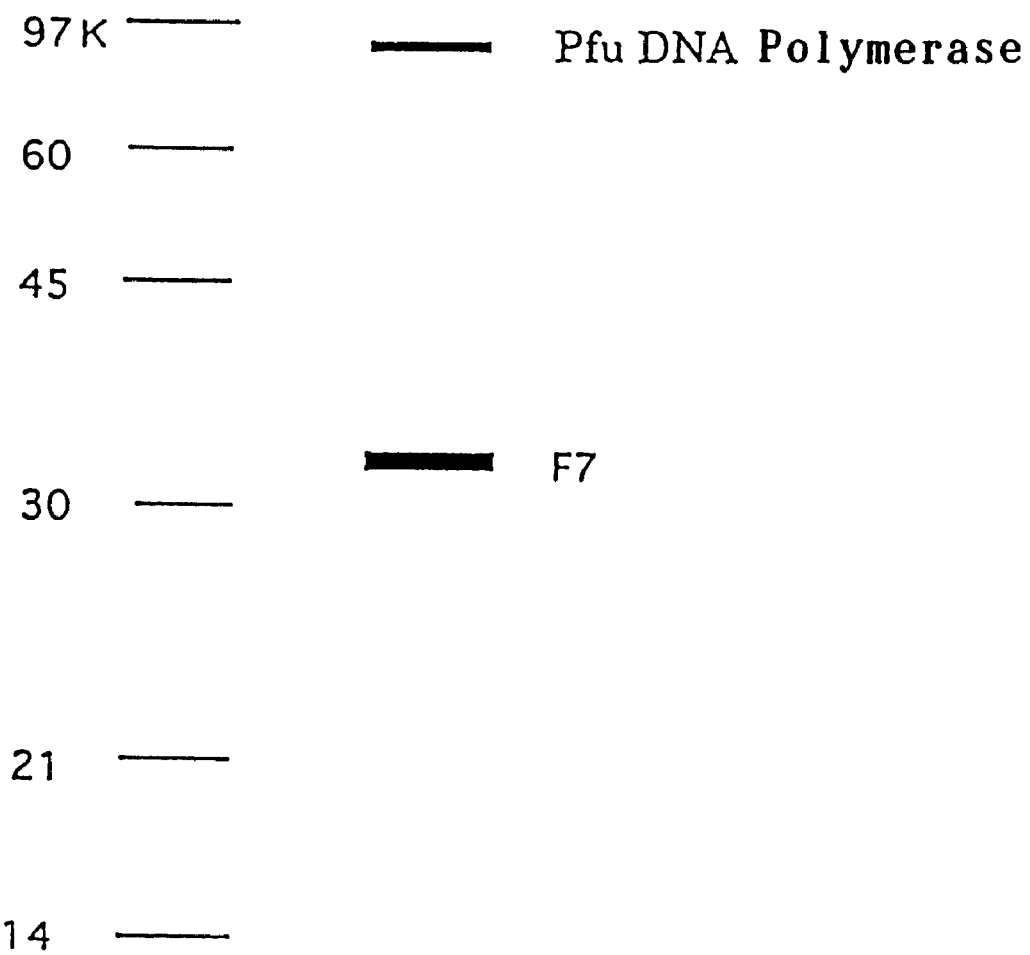
FIG. 10 shows the analytical results of SDS-PAGE of the protein (F7) isolated by an anti-Pfu DNA polymerase antibody column. The molecular weight of F7 on SDS-PAGE is deduced to be about 33 kDa.

*Pyrococcus furiosus* DSM3638 was cultured in the same manner as the method described in Example 1 to yield cells in 9 liters of a culture medium. These cells were suspended in 33 ml of buffer C (50 mM Tris-HCl, pH 8.0, 0.1 mM ATP) containing 2 mM PMSF, and the resulting suspension was treated with an ultrasonic disrupter. The disrupted solution obtained was centrifuged at 12,000 rpm for 10 minutes, and 44 ml of the supernatant obtained was applied to the anti-Pfu DNA polymerase antibody column, previously equilibrated with buffer C. The column was washed with buffer C containing 0.1 M NaCl, and thereafter the Pfu DNA polymerase complex was eluted with elution buffer (50 mM Tris-HCl, pH 8.0, 8 M urea). This eluate was subjected to SDS-PAGE (12.5% polyacrylamide gel; 25 mM Tris-HCl, 192 mM glycine, 0.1% SDS, pH 8.4 used as electrophoresis buffer). The gel after electrophoresis was stained with Coomassie brilliant blue R-250 by a conventional method. As a result, as shown in FIG. 10, besides the band of Pfu DNA polymerase, a band was detected at a position corresponding to the above F7.

With this in mind, a concentrate of this eluate was subjected to SDS-PAGE in the same manner as above, and the gel obtained was subjected to Western blotting using the anti-Pfu DNA polymerase antibody in the same manner as Example 3(2). From the result of SDS-PAGE shown in FIG. 10 and the results of the above Western blotting, there was elucidated that the band at a position corresponding to F7 is a protein unreactive with the anti-Pfu DNA polymerase antibody.

Furthermore, the N-terminal amino acid sequence of the protein of this band was analyzed in the same manner as Example 3(2), and as a result, it was found that this protein is F7.

(4) Confirmation of Formation of Complex of Pfu DNA Polymerase and F7 Using Gel Filtration Chromatography 1.2 ml Of the F7 authentic sample obtained in Example 8(4) was subjected to buffer-exchange with 50 mM Tris-HCl (pH 8.0) containing 2 mM 2-mercaptoethanol and 75 mM NaCl using PD-10 column, and thereafter the resulting solution was concentrated to a volume of 50 µl using Centricon-10.

Ten microliters each of the 0.1 mM Pfu DNA polymerase solution described in Example 10(1), the above 0.1 mM (calculated as a trimer) F7 solution, and a mixture of 0.1 mM Pfu DNA polymerase and 0.1 mM F7, was heated from 60° to 90° C. over a period of 30 minute. Each heat-treated solution was applied to Superdex 200 PC3.2/30 gel filtration column (manufactured by Pharmacia), previously equilibrated with 50 mM Tris-HCl buffer, pH 8.0, containing 2 mM 2-mercaptoethanol and 75 mM NaCl, and the elution was carried out with the same buffer. Pfu DNA polymerase and F7 were eluted at positions corresponding to molecular weights of about 76 kilodaltons and about 128 kilodaltons, respectively. In the case of the mixture of Pfu DNA polymerase and F7, a main peak corresponding to about 320 kilodaltons and a minor peak corresponding to about 128 kilodaltons were eluted. The fractions with these two peaks were each subjected to SDS-PAGE (12.5% polyacrylamide gel; 25 mM Tris-HCl, 192 mM glycine, 0.1% SDS, pH 8.4 used as electrophoresis buffer). The fraction corresponding to about 320 kilodaltons contained Pfu DNA polymerase and F7, whereas the fraction corresponding to about 128 kilodaltons contained F7 only. From the above, there was found that a complex of Pfu DNA polymerase and F7 is formed.

(5) Extension Activity of Pfu DNA Polymerase-F7 Complex

Figure 11:
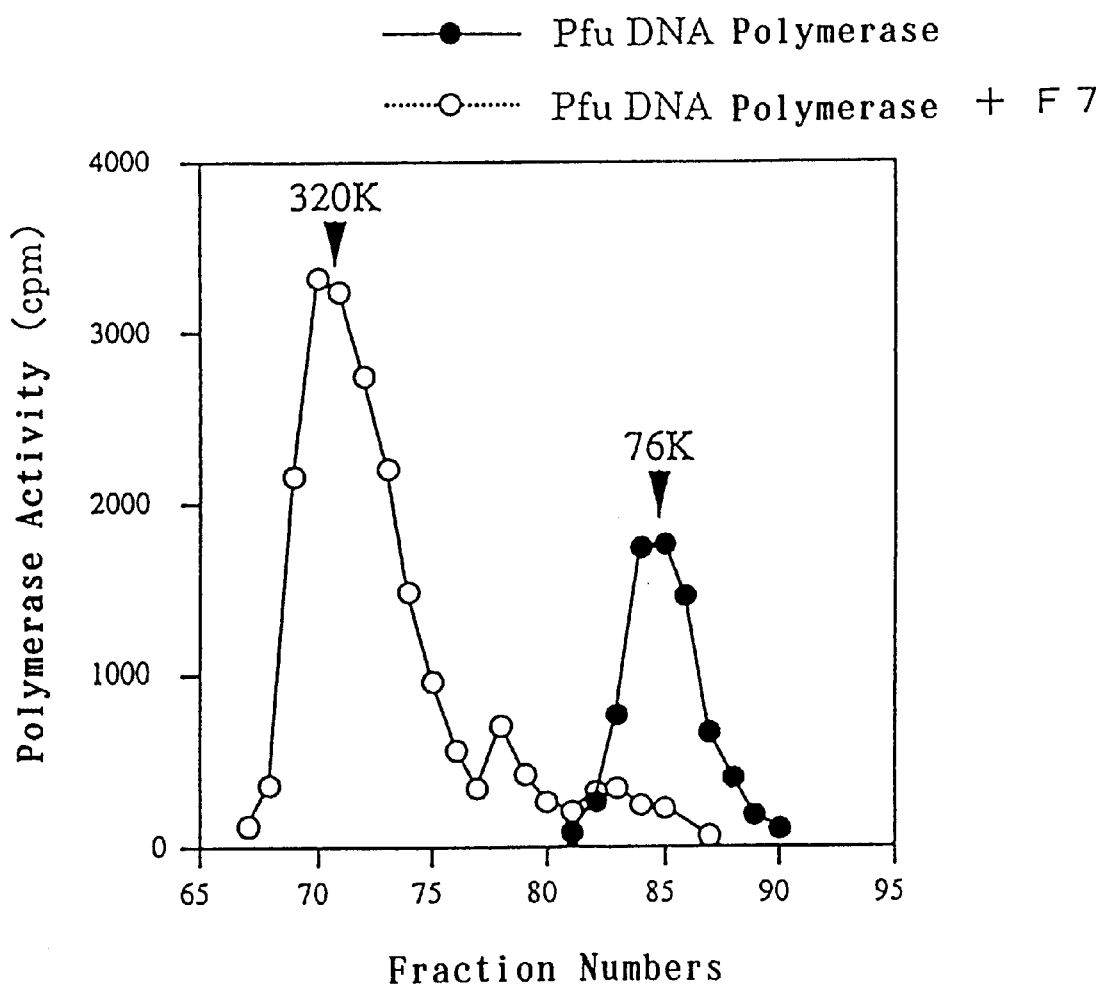
FIG. 11 shows the analytical results of DNA polymerase activity of the eluate obtained by subjecting to gel filtration Pfu DNA polymerase and a mixture of Pfu DNA polymerase and F7.

In the gel filtration described in Example 10(4), 20 µl each of the eluates obtained by gel filtration of Pfu DNA polymerase alone corresponding to about 76 kilodaltons, and of the mixture of Pfu DNA polymerase and F7 corresponding to 320 kilodaltons, were each collected, and the primer extension activity of each eluate or mixture was determined by the activity determination method described in Example 8(5) where the non-labeled M13-HT primer was used as a substrate. Also, at the same time, incorporation activity was determined by the method described in Example 2(1) where an activated DNA was used as a substrate. The results are shown in FIG. 11. The ratio of the primer extension activity to the incorporation activity for the two fractions was determined such that the ratio of 0.65 was obtained for the about 320 kilodalton fraction, and the ratio of 0.29 was obtained for the about 76 kilodalton fraction. Therefore, there was found that the primer extension activity of Pfu DNA polymerase is enhanced by the formation of a complex with F7.

Example 11

(1) Selection of Cosmid Clones Carrying Gene Encoding Homologs of RFC Large Subunit Regarding the amino acid sequence of the RFC large subunit of *Methanococcus jannaschii* [*Science*, 273, 1058–1073 (1996)], homology to the amino acid sequences of PFU-RFC small subunits without carrying intein described in Example 9 was examined. In reference to the amino acid sequence of a region highly conserved among them, the primer RFLS15 for searching the gene encoding the RFC large subunit was synthesized. The nucleotide sequence of the primer RFLS15 is shown in SEQ ID NO: 60 in Sequence Listing. PCR was carried out using a combination of this primer with the above primer RF-F1 corresponding to a similar amino acid sequence existing in the two subunit proteins of RFC with *Pyrococcus furiosus* genomic DNA as a template. The PCR was carried out using a reaction mixture of the same composition as that used in Example 5(1) using Pfu DNA polymerase, 0.25 μg of template DNA and 100 pmol each of primers. Of the two kinds of DNA fragments amplified by this PCR, an amplified DNA fragment of about 630 bp, of which size differs from the anticipated size of the amplification product derived from the PFU-RFC small subunit gene was isolated. This DNA fragment was subcloned into plasmid vector pUCll9, and its nucleotide sequence was determined. Thereafter, in reference to the nucleotide sequence determined, the primers RFLS-S3 and RFLS-S4, of which nucleotide sequences are shown in SEQ ID NOs: 61 and 62 in Sequence Listing, were then synthesized.

PCR was carried out using these two primers with the cosmid DNA prepared in Example 1 as a template, whereby selecting cosmid clones assumed to carry the gene encoding homologs of the RFC large subunit. The PCR was carried out in a reaction mixture of the same composition as that used in Example 5(1) using Pfu DNA polymerase as an enzyme in 30 cycles, wherein one cycle comprises a process consisting of at 94° C. (30 seconds)—55° C. (30 seconds)—72° C. (2 minutes). As a result, Cosmid Clone Nos. 254, 310, 313, 377 and 458 were found to carry the desired gene (PFU-RFCLS gene). These Cosmid Clone Numbers were identical to the above cosmid clones carrying the PFU-RFC gene. With this in mind, the nucleotide sequence of the DNA insert in the plasmid pRFS254NdB shown in SEQ ID NO: 55 in Sequence Listing was examined, and it was found that a homolog (PFU-RFCLS) of the RFC large subunit was encoded by the open reading frame starting at No. 3109 of the sequence immediately downstream of the PFU-RFC gene. However, this plasmid pRFS254NdB did not harbor a full length of the PFU-RFCLS gene.

(2) Subcloning of PFU-RFCLS Gene

Figure 12:
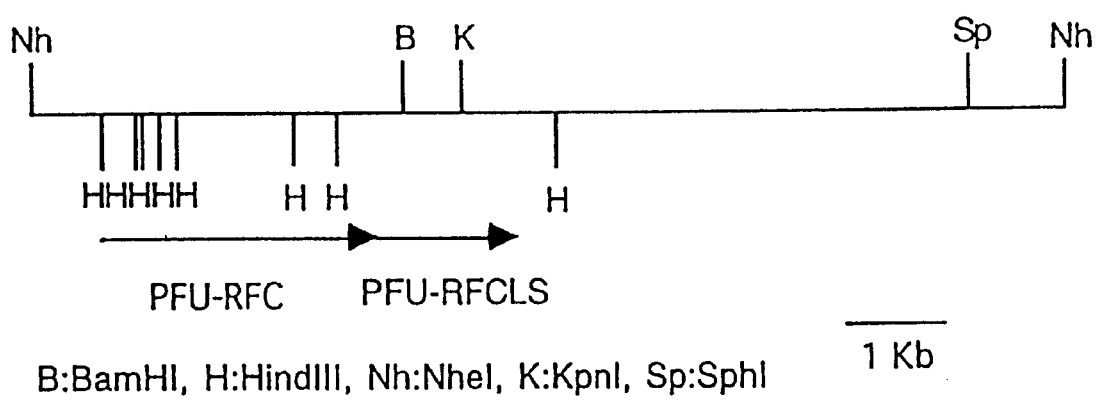
FIG. 12 is a restriction endonuclease map of a DNA insert of the plasmid pRFLSNh carrying a gene encoding the PFU-RFCLS protein.

In order to isolate a DNA fragment carrying the full length of the PFU-RFCLS gene, Clone No. 254 above was digested with NheI, and the various DNA fragments obtained were cut out, and each was subcloned into plasmid vector pTV118N (manufactured by Takara Shuzo Co., Ltd.). PCR was carried out using RFLS-S3 and RFLS-S4 as primers with each of the recombinant plasmids obtained as a template, in order to examine whether or not the PFU-RFCLS gene is present. As a result, an NheI fragment of about 11 kb was found to carry the RFLS gene. The plasmid resulting from insertion of this NheI fragment into pTV118N was named the plasmid pRFLSNh. In addition, a restriction endonuclease map of the DNA insert contained in this plasmid was prepared, and the results as shown in FIG. 12 were obtained.

Furthermore, the nucleotide sequence of the DNA insert contained in this plasmid was determined by the dideoxy method. Of the nucleotide sequence determined, the nucleotide sequence of the open reading frame portion encoding PFU-RFCLS is shown in SEQ ID NO: 63 in Sequence Listing. The amino acid sequence of PFU-RFCLS deduced from the sequence is shown in SEQ ID NO: 64 in Sequence Listing.

Example 12

(1) Selection of Cosmid Clones Carrying F5 Gene

On the-basis of the N-terminal amino acid sequence of F5 obtained in Example 3, the primers F5-1-1 and F5-2, of which nucleotide sequences are shown in SEQ ID NO: 65 and 66, respectively, in Sequence Listing, were synthesized. First PCR was carried out using 100 pmol each of F5-1-1 and the cassette primer C1 (manufactured by Takara Shuzo Co., Ltd.) with 1 pl of the PstI cassette DNA prepared in Example 4 as a template. Second PCR was carried out using 100 pmol of both F5-2 and the cassette primer C2 (manufactured by Takara Shuzo Co., Ltd.) with 1 μl of the above reaction mixture as a template. This second PCR was carried out using TaKaRa PCR amplification kit (manufactured by Takara Shuzo Co., Ltd.) in accordance with the instructions attached. An amplified DNA fragment of about 900 bp was subcloned into plasmid vector pTV118N (manufactured by Takara Shuzo Co., Ltd.). The plasmid obtained was named pF5P2, and its nucleotide sequence was determined. Thereafter, on the basis of the sequence determined, primers F5S1 and F5S2, of which nucleotide sequences are shown in SEQ ID NOs: 67 and 68, respectively, in Sequence Listing, were synthesized. PCR was carried out using these F5S1 and F5S2 with the cosmid DNA described in Example 1 as a template, whereby selecting cosmid clones carrying the F5 gene. This PCR was carried out using the TaKaRa PCR amplification kit in accordance with the instructions attached. As a result, there were found that Cosmid Clone Nos. 15, 96, 114, 167, 277, 348, 386, 400, 419, 456, 457 and 484 carry the F5 gene. These Cosmid Clone Numbers were identical to the cosmid clones carrying the F7 gene. With this in mind, the nucleotide sequence shown in SEQ ID NO: 41 in Sequence Listing was examined, and it was found that a portion on or after No. 892, which is downstream of the F7 gene on the sequence, carries a first half of the F5 gene.

(2) Subcloning of F5 Gene

Figure 13:
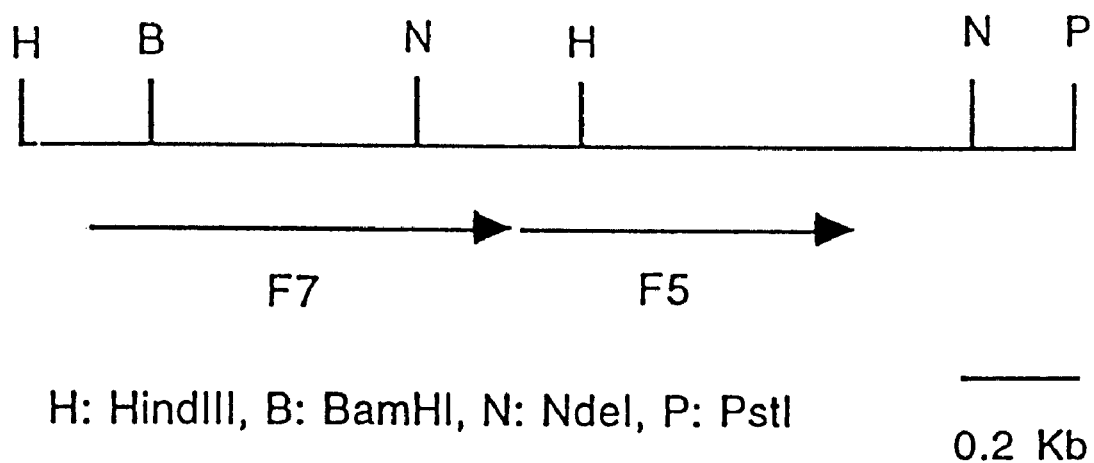
FIG. 13 is a restriction endonuclease map around the gene encoding the F5 protein on genomic DNA of *Pyrococcus furiosus*.

In order to subclone the F5 gene, a restriction endonuclease map for NcoI, BamHI, PstI, HindIII and NdeI (manufactured by Takara Shuzo Co., Ltd.) in the neighborhood of the F5 gene was prepared using the plasmid pF7-HH-18 obtained in Example 8 and the above plasmid pF5P2, and the results as shown in FIG. 13 were obtained.

On the basis of the restriction endonuclease map shown in FIG. 13, Cosmid Clone No. 15 was digested with NdeI, and a fragment of about 900 bp was cut out and subcloned into plasmid vector pTV118Nd. As to the recombinant plasmid obtained, a plasmid resulting from insertion of the F5 gene in the orthodox orientation with respect to the lac promoter was named pF5NNF-1.

(3) Determination of Nucleotide Sequence of DNA Fragment Carrying F5 Gene

The nucleotide sequence of the DNA insert in the above plasmid pF5NNF-1 was determined by the dideoxy method. As a result of analyzing the nucleotide sequence determined, there was found an open reading frame encoding a protein of which N-terminal amino acid sequence is identical to that of F5. The nucleotide sequence of this open reading frame is shown in SEQ ID NO: 69 in Sequence Listing, and the amino acid sequence of F5 as deduced from the above nucleotide sequence is shown in SEQ ID NO: 70 in Sequence Listing. This amino acid sequence was searched for homology to the amino acid sequences of known proteins, and as a result, proteins homologous thereto were not found.

(4) Construction of Plasmid for F5 Expression

PCR was carried out using the primers F5Nco and F5CBam, of which nucleotide sequences are shown in SEQ ID NOs: 71 and 72, respectively, in Sequence Listing, with the above plasmid pF5NNF-1 as a template. The PCR was carried out in a reaction mixture of the same composition as that used in Example 5(1) using Pfu DNA polymerase. Using 1 ng of a template DNA and 20 pmol each of both of the primers, the reaction was carried out in 25 cycles, wherein one cycle comprises a process consisting of at 94° C. (30 seconds)—55° C. (30 seconds)—72° C. (2 minutes). An amplified DNA fragment of an about 640 base pairs was digested with NcoI and BamHI (both manufactured by Takara Shuzo Co., Ltd.), and the fragment obtained was ligated with pET15b (manufactured by Novagen), previously linearized with NcoI and BamHI. This plasmid was named pF5NBPET. Of the DNA insert in the plasmid, the region amplified by PCR was analyzed by the dideoxy method to determine its nucleotide sequence. There was confirmed that there is no mutation caused by PCR.

*Escherichia coli* HMS174(DE3)/pF5NBPET, *Escherichia coli* HMS174(DE3) transformed with the plasmid pF5NBPET, was evaluated for F5 expression, and there was demonstrated that a protein of a molecular weight corresponding to F5 in the culture of the transformant is expressed.

Example 13

(1) Subcloning of F3 Gene

On the basis of the N-terminal amino acid sequence of F3 obtained in Example 3, the primers F3-1 and F3-3-1, of which nucleotide sequences are shown in SEQ ID NOs: 73 and 74 in Sequence Listing, were synthesized. First PCR was carried out using 100 pmol of the primer F3-1 and 20 pmol of the cassette primer C1 with 1 μl of the BglII/Sau3AI cassette DNA of Example 4 as a template. With 1 μl of the above reaction mixture as a template, second PCR was carried out using F3-3-1 and the cassette primer C2. The PCR was carried out in a reaction mixture of the same composition as that used in Example 5(1) using Pfu DNA polymerase as an enzyme in 30 cycles for the first PCR and 25 cycles for the second, wherein one cycle comprises a process consisting of at 94° C. (30 seconds)—45° C. (30 seconds)—72° C. (2 minutes). An amplified DNA fragment of about 500 bp by this reaction was subcloned into plasmid vector pTV118N, and a part of its nucleotide sequence was determined by the dideoxy method using M4 and RV primers (manufactured by Takara Shuzo Co., Ltd.). On the basis of the sequence determined, the primers F3S1, F3S2, F3S3 and F3S4, of which nucleotide sequences are shown in SEQ ID NOs: 75, 76, 77 and 78 in Sequence Listing, were then synthesized. PCR was carried out using these F3S1 and F3S2 primers with the cosmid DNA prepared in Example 1 as a template, and cosmid clones carrying the F3 gene were searched. As a result, there was found no cosmid clone assumed to carry the F3 gene. With this in mind, PCR was carried out using the primer F3S3 or F3S4 and the primer C2 with each cassette DNA of Example 4 as a template. As a result of mapping of the restriction endonuclease recognition sites in the neighborhood of the F3 gene, there was anticipated that the F3 gene is present in a fragment of about 2.6 kb between the SalI site and the HindIII site. On the basis of the results, 4 μg of *Pyrococcus furiosus* genomic DNA was digested with SalI and HindIII, and thereafter a DNA fragment of about 2.6 kb was collected and subcloned into pTV118N vector. PCR was carried out using the primer F3S4 and the primer RV-N (manufactured by Takara Shuzo Co., Ltd.) with each of the recombinant plasmids thus obtained as a template, to examine for the presence of the F3 gene. As a result, a plasmid harboring a 2.6 kb SalI-HindIII fragment carrying the F3 gene was obtained, and this plasmid was named the plasmid pF3SH92. *Escherichia coli* JM109/pF3SH92, *Escherichia coli* JM109 transformed with this plasmid, was examined for F3 expression, and as a result, there was confirmed that a protein having a molecular weight corresponding to F3 is expressed.

(2) Determination of Nucleotide Sequence of DNA Fragment Carrying F3 Gene

The nucleotide sequence of the DNA insert in the above plasmid pF3SH92 was determined by the dideoxy method. As a result of analyzing the nucleotide sequence determined, there was found an open reading frame encoding a protein of which N-terminal amino acid sequence is identical to that of F3. The nucleotide sequence of this open reading frame is shown in SEQ ID NO: 79 in Sequence Listing, and the amino acid sequence of F3 as deduced from the nucleotide sequence is shown SEQ ID NO: 80, respectively, in Sequence Listing. This amino acid sequence was searched for homology to the amino acid sequences of known proteins, and as a result, the amino acid sequence is found to be homologous to *Mycoplana ramosa*-derived acetyl polyamine aminohydrase [*Journal of Bacteriology*, 178, 5781–5786 (1996)] and human histone deacetylase [*Science*, 272, 408–411 (1996)].

Example 14

In the following Example, the activities of commercially available enzymes are shown on the basis of the labeling for individual enzymes. Also, reaction mixtures containing commercially available enzymes were prepared in accordance with the manuals for the respective enzymes, or using the reaction buffers attached thereto, unless otherwise specified. PCR was carried out using GeneAmp PCR System 9600 (manufactured by Perkin-Elmer).

(1) Preparation of Anti-PFU-RFC Antibody

The PFU-RFC authentic sample of Example 9(6) was diluted so as to have a concentration of 1 mg/100 μl with 50 mM Tris-HCl, pH 8.0, 2 mM 2-mercaptoethanol and 75 mM NaCl, and the mixture was emulsified with an equal volume of Freund's complete adjuvant. This emulsion was subcutaneously injected to rabbits at 50 μl per injection four times at 3-week intervals. Ten days after final immunization, whole blood was extracted. After allowing to stand at room temperature for 60 minutes, the extracted blood was centrifuged to yield 50 ml of an antiserum containing the anti-PFU-RFC polyclonal antibody. To 20 ml of this antiserum, 20 ml of a saturated solution of ammonium sulfate was added, and the mixture was gently stirred at 4° C. for 45 minutes and subsequently centrifuged. The precipitate obtained was suspended in 5 ml of 20 mM sodium phosphate buffer, pH 7.0, and thrice subjected to 2-hour dialysis against 2 liters of the same buffer as a dialysate. After dialysis, 14 ml of the solution was applied to Protein A column (manufactured by Pharmacia), previously equilibrated with 20 mM sodium phosphate buffer (pH 7.0). After the column was washed with the same buffer, the elution was carried out with 0.1 M sodium citrate buffer (pH 3.0). After the anti-PFU-RFC antibody eluted was neutralized with 1 M Tris-HCl, pH 9.0, the mixture was then concentrated using Centriflow CF-50 and subjected to exchange with coupling buffer (0.5 M NaCl, 0.2 M NaHCO$_3$, pH 8.3) using PD-10 column to prepare a solution containing the anti-PFU-RFC antibody.

(2) Preparation of Anti-PFU-RFC Antibody Column

HiTrap NHS-activated column (manufactured by Pharmacia) was washed with 6 ml of 1 mM HCl, and thereafter 0.95 ml of the above anti-PFU-RFC polyclonal antibody solution (containing 3.8 mg equivalent of the anti-PFU-RFC antibody) was applied thereto. Subsequently, an anti-PFU-RFC antibody column was prepared in the same manner as Example 2(3).

(3) Purification of Complex Containing PFU-RFC Using Anti-PFU-RFC Antibody Column

*Pyrococcus furiosus* DSM3638 was cultured in the same manner as the method described in Example 1 to yield cells in 10 liters of culture medium. These cells were suspended in 33 ml of buffer C (50 mM Tris-HCl, pH 8.0, 0.1 mM ATP) containing 2 mM PMSF, and the suspension was treated with an ultrasonic disrupter. The disrupted solution was centrifuged at 12,000 rpm for 10 minutes, and 38 ml of the supernatant obtained was applied to the anti-PFU-RFC antibody column, previously equilibrated with buffer C containing 0.1 M NaCl. After washing with buffer C containing 0.1 M NaCl, the column was heated at 85° C. for 1 hour, and the PFU-RFC complex was eluted with buffer C containing 0.1 M NaCl. This eluate was subjected to SDS-PAGE (12.5% polyacrylamide gel; 25 mM Tris-HCl, 192 mM glycine, 0.1% SDS, pH 8.4 used as electrophoresis buffer). The gel after electrophoresis was stained with Coomassie brilliant blue R-250 by a conventional method, and as a result, in addition to the band of PFU-RFC, one band at a position for 33 kilodaltons, which corresponds to the above F7, and two bands near 60 kilodaltons were detected.

With this in mind, the N-terminal amino acid sequences of the proteins existing in these three bands were analyzed in the same manner as Example 3(2). As a result, as shown in FIG. 14, the N-terminal amino acid sequence of the protein at a position corresponding to the above F7 was found to be identical to that of F7, and each of the N-terminal amino acid sequences of the two kinds of proteins near 60 kilodaltons was found to be identical to the above N-terminal amino acid sequence of the PFU-RFCLS.

Next, the amounts of the PFU-RFC, PFU-RFCLS and F7 proteins in this eluate were quantified by the amount of Coomassie brilliant blue bound thereto. The eluate was subjected to SDS-PAGE (12.5% polyacrylamide gel; 25 mM Tris-HCl, 192 mM glycine, 0.1% SDS, pH 8.4 used as electrophoresis buffer). The gel after electrophoresis was stained with Coomassie brilliant blue R-250 by a conventional method, and thereafter the band was cut out and treated with 500 µl of 70% formic acid to extract the Coomassie brilliant blue, and the absorbance at 630 nm was determined. On the basis of a calibration curve prepared using the F7 authentic sample of Example 8(4) and the PFU-RFC authentic sample of Example 9(6), each of a known concentration, it was found that 208 µg of PFU-RFC, 55 µg of PFU-RFCLS and 51 µg of the F7 protein were contained in 500 µl of the eluate. The complex constituted by the three proteins PFU-RFC, PFU-RFCLS and F7 as described above is hereinafter referred to as RFC-N complex.

(4) Effects of RFC-N Complex on Primer Extension Reactions

Figure 15:
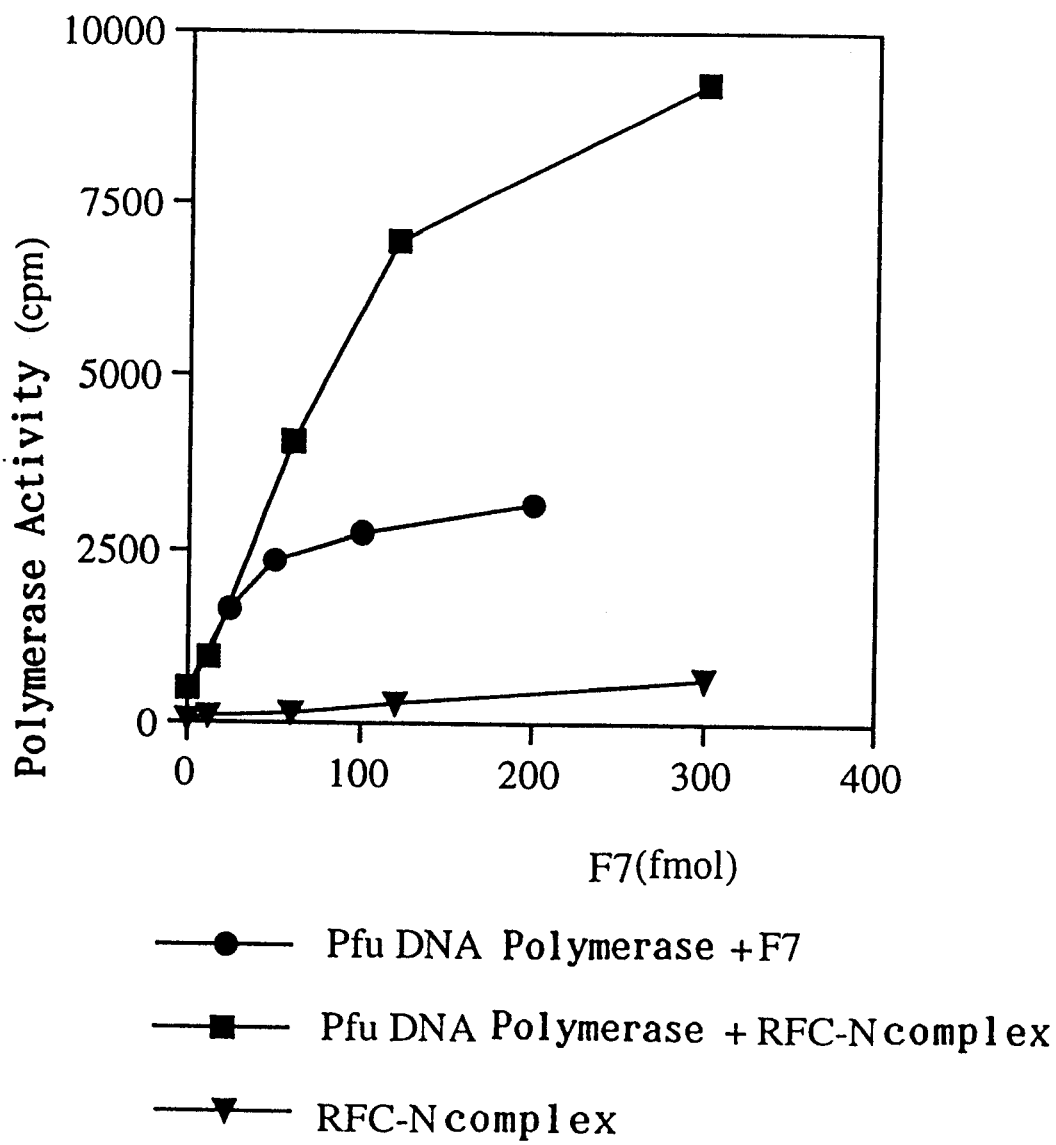
FIG. 15 is a graph showing DNA polymerase activity when F7 or RFC-N complex is added.

In order to examine the effects of the RFC-N complex obtained in Example 14(3) on the primer extension reactions of various polymerases, the activities of Pfu polymerase C and Pfu DNA polymerase (α-type DNA polymerase, manufactured by STRATAGENE) were compared between cases where the RFC-N complex was added and cases where only its constituent F7 was added. The DNA polymerase activities were determined in the same manner as the method described in Example 8(5), except that 50 fmol of Pfu polymerase C or Pfu DNA polymerase was used. For the determination of the DNA polymerase activities, one prepared by annealing the HT primer, which is a synthetic oligonucleotide of 45 bases, to M13 phage single-stranded DNA (M13 mp18ss DNA, manufactured by Takara Shuzo Co., Ltd.), was used as shown in Example 8(5) (M13-HT primer). The nucleotide sequence of the HT primer is shown in SEQ ID NO: 42 in Sequence Listing. The results for Pfu DNA polymerase are shown in FIG. 15. The amounts of F7 and the RFC-N complex added are expressed in the molar numbers of F7 and RFC-N complex contained in the reaction mixture. As shown in FIG. 15, the RFC-N complex showed higher increase in the activity to Pfu DNA polymerase than that of F7 alone.

Furthermore, the primer extension activity was studied by the method described in Example 8(5). Reaction mixtures for determination were prepared with the following compositions: 1) 100 fmol of F7, 2) 0.05 µl of the RFC-N complex (containing 60 fmol of F7), 3) 10 fmol of Pfu polymerase C, 4) 10 fmol of Pfu polymerase C+100 fmol of F7, 5) 100 fmol of Pfu polymerase C+0.05 µl of the RFC-N complex, 6) 20 fmol of F7, 7) 0.02 µl of the RFC-N complex (containing 24 fmol of F7), 8) 10 fmol of Pfu DNA polymerase, 9) 10 fmol of Pfu DNA polymerase+20 fmol of F7, 10) 10 fmol of Pfu DNA polymerase+0.02 µl of the RFC-N complex. To 1 µl of each reaction mixture for determination, 9 µl of a reaction mixture [20 mM Tris-HCl (pH 9.0), 15 mM MgCl$_2$, 2 mM 2-mercaptoethanol, 40 µM each of dATP, dGTP, dCTP and dTTP] containing 0.01 µg/µl $^{32}$P-labeled M13-HT primer was added, and the reaction was carried out at 75° C. for 2.5 minutes. After termination of the reaction, the reaction mixture was cooled with ice to stop the reaction, and 1 µl of 200 mM EDTA and 5 µl of a reaction stopper (95% formamide, 20 mM EDTA, 0.05% bromophenol blue, 0.05% xylene cyanol) were further added thereto, and the mixture was subjected to thermal denaturation treatment at 95° C. for 5 minutes. After 1.6 µl of this reaction mixture was electrophoresed using 6% polyacrylamide gel containing 8 M urea, an autoradiogram was prepared.

Next, in order to analyze primer extension reaction products of longer chains, the analysis was carried out by the method described in Example 8(5). To 1 µl of each of sample solutions 1) to 10) above, 9 µl of a reaction mixture [20 mM Tris-HCl, pH 9.0, 15 mM MgCl$_2$, 2 mM 2-mercaptoethanol, 40 µM each of dATP, dGTP, dCTP and dTTP, 84 nM [α-$^{32}$P]-dCTP] containing M13-HT primer to have a final concentration of 0.01 µg/µl was added, and the mixture was reacted at 75° C. for 2.5 minutes. After termination of the reaction, to the ice cooled reaction mixture, 1.11 µl of 200 mM EDTA, 1.23 µl of 500 mM NaOH, and 2.47 µl of 6-fold concentrated loading buffer (0.125% bromophenol blue, 0.125% xylene cyanol, 9% glycerol) were sequentially added. After 6 µl of this mixture was electrophoresed using 0.5% alkaline agarose gel, an autoradiogram was prepared.

In either case of Pfu polymerase C and Pfu DNA polymerase, the amount of long-chain extension products increased in the case where the RFC-N complex was added as compared to the case of F7 alone.

The chain lengths of the long-chain extension products were found to be up to about 7.2 kb, a full length of the template, in either of the polymerases used, in the case of F7 alone and of the RFC-N complex.

Example 15

Construction of Plasmid for rRFC-M Expression (1) A plasmid for simultaneously expressing PFU-RFCLS and PFU-RFC was constructed. In reference to the nucleotide sequence determined in Example 11(2), the primer RFLS-NdeN, of which nucleotide sequence is shown in SEQ ID NO: 81 in Sequence Listing, and RFLS-S9, of which nucleotide sequence is shown in SEQ ID NO: 82, were synthesized. PCR was carried out using both of these primers with the above plasmid pRFLSNh as a template. The PCR was carried out in a reaction mixture of the same composition as that used in Example 5(1) using Pfu DNA polymerase as an enzyme, 10 ng of the plasmid pRFLSNh and 20 pmol each of the primers in 30 cycles, wherein one cycle comprises a process consisting of at 94° C. (30 seconds)—55° C. (30 seconds)—72° C. (3 minutes). An NdeI-PstI fragment of about 920 bp isolated after digesting an amplified DNA fragment obtained by PCR with NdeI and PstI, a PstI-EcoRI fragment of about 600 bp isolated from the plasmid pRFLSNh obtained in Example 11(2), and an EcoRI-BamHI fragment of about 2 kb isolated from the plasmid pRFS254SNc obtained in Example 9(4) were mixed and subcloned between the NdeI and BamHI sites of plasmid vector pTV119Nd. The recombinant plasmid thus obtained was named pRFC10. In addition, *Escherichia coli* JM109 transformed with the plasmid was named *Escherichia coli* JM109/pRFC10. This transformant was found to possess a high level of expression of PFU-RFCLS and PFU-RFC.

Figure 16:
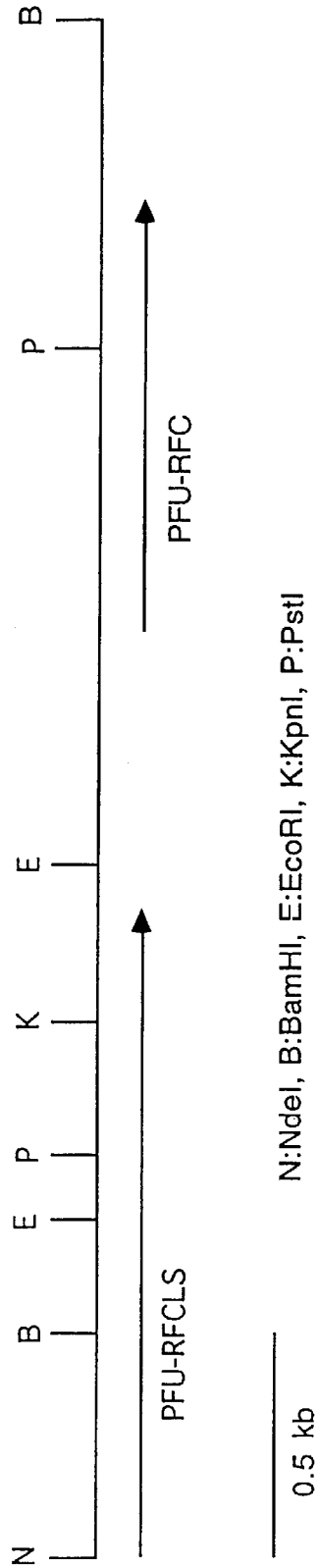
FIG. 16 is a restriction endonuclease map of a DNA insert of the plasmid pRFC10 carrying genes encoding PFU-RFCLS and PFU-RFC.

(2) Determination of Nucleotide Sequence of Genes Encoding PFU-RFCLS and PFU-RFC Of the DNA insert in the plasmid pRFC10 obtained in Example 15(1), the region amplified by PCR was analyzed by the dideoxy method to determine its nucleotide sequence, and it was confirmed that there is no mutation caused by PCR. From this result and the results of Example 9(3) and Example 11(2), the nucleotide sequence of the gene encoding PFU-RFCLS and PFU-RFC without carrying intein was determined. The nucleotide sequence of the genes encoding PFU-RFCLS and PFU-RFC without carrying intein thus obtained is shown in SEQ ID NO: 83 in Sequence Listing, and its restriction endonuclease map is shown in FIG. 16.

Example 16

Preparation of rRFC-M Authentic Sample

*Escherichia coli* JM1O9/pRFC10 obtained in Example 15(1) was cultured for 16 hours in 500 ml×4 of LB medium (10 g/l trypton, 5 g/l yeast extract, 5 g/l NaCl, pH 7.2), in which ampicillin was present at a concentration of 100 µg/ml, and IPTG is present at 1 mM. After harvesting, cells were suspended in 35.9 ml of sonication buffer [50 mM Tris-HCl, pH 8.0, 2 mM 2-mercaptoethanol, 10% glycerol, 2 mM PMSF (phenylmethanesulfonyl fluoride)], and the suspension was treated with an ultrasonic disrupter. After centrifugation at 12,000 rpm for 10 minutes, a heat treatment was carried out at 80° C. for 15 minutes. Thereafter, centrifugation at 12,000 rpm for 10 minutes was again carried out to yield 33.0 ml of a heat-treated enzyme solution. This solution was then applied to RESOUCE Q column (manufactured by Pharmacia), previously equilibrated with buffer A (50 mM Tris-HC1, pH 8.0, 2 mM 2-mercaptoethanol, 10% glycerol), and the applied solution was chromatographed using FPLC system (manufactured by Pharmacia). The elution was carried out on a linear concentration gradient of 0 to 500 mM NaCl.

As a result of analyzing the eluate by SDS-PAGE (12.5% polyacrylamide gel; 25 mM Tris-HCl, 192 mM glycine, 0.1% SDS, pH 8.4 used as electrophoresis buffer), PFU-RFCLS and PFU-RFC were both eluted at an NaCl concentration of 240 mM. When the eluate obtained from cells in which PFU-RFC was expressed alone as described in Example 9(6) was applied to RESOURCE Q column, the eluate was not adsorbed to RESOURCE Q column. On the other hand, when the eluate obtained from cells in which PFU-RFCLS and PFU-RFC were simultaneously expressed was applied to RESOURCE Q column, the eluate was adsorbed thereto, and PFU-RFCLS and PFU-RFC were simultaneously eluted at an NaCl concentration of 240 mM, as described above. From the results, it was demonstrated that these two proteins have formed a complex. This complex is hereinafter referred to as rRFC-M complex.

After 4.8 ml of an enzyme solution obtained by collecting the rRFC-M complex fraction was concentrated using Centriflow CF50, the concentrate was subjected to exchange with buffer A containing 150 mM NaCl using PD-10 column (manufactured by Pharmacia), and 3.5 ml of the solution was applied to Heparin column (manufactured by Pharmacia), previously equilibrated with buffer A containing 150 mM NaCl. Using FPLC system, the chromatogram was developed on a linear concentration gradient from 150 mM to 650 mM NaCl, and an rRFC-M complex fraction eluted at 450 mM NaCl was obtained. Using Centricon-10 (manufactured by Amicon), 3.9 ml of this fraction was concentrated, and 115 µl of the concentrate was applied to Superdex 200 gel filtration column (manufactured by Pharmacia), previously equilibrated with 50 mM Tris-HCl, pH 8.0, 2 mM 2-mercaptoethanol and 75 mM NaCl. The elution was carried out with the same buffer, and the rRFC-M complex was found to have a retention time of 26.3 minutes. From the comparative results with the position of the elution of a molecular weight marker under the same conditions, the molecular weight of the rRFC-M complex was calculated as about 370 kilodaltons.

Furthermore, in order to determine the compositional ratio of each unit in the rRFC-M complex, the above eluted fraction of a molecular weight of about 370 kDa was subjected to SDS-PAGE.

The gel after electrophoresis was stained with Coomassie brilliant blue R-250 by a conventional method, and thereafter the bands of the PFU-RFCLS and PFU-RFC proteins were cut out and extracted with 500 µl of 70% formic acid. The absorbance at 630 nm of each extract was determined, and the results were compared with the calibration curve prepared by using PFU-RFC prepared in Example 9(6), and whereby the amount of each protein was determined and the molar number was calculated.

As a result, PFU-RFCLS and PFU-RFC were found to exist in a 1:4 ratio. Based on the fact that the molecular weight of the rRFC-M complex as calculated by the gel filtration described above was about 370 kDa, the rRFC-M complex was assumed to be formed by two molecules of PFU-RFCLS and eight molecules of PFU-RFC. With this in mind, the molar number was calculated, taking the above rRFC-M complex as 1 unit.

Example 17

Construction of Plasmid F3 Expression (1) PCR was carried out using the primer F3Nd, of which nucleotide sequence is shown in SEQ ID NO: 84 in Sequence Listing, and the F3S2 primer, of which nucleotide sequence is shown in SEQ ID NO: 76, with the plasmid pF3SH92 as prepared in Example 13 as a template. The PCR was carried out in a reaction mixture of the same composition as that used in Example 5(1) using Pfu DNA polymerase as an enzyme, 1 ng of the plasmid pF3SH92 and 20 pmol each of the primers in 30 cycles, wherein one cycle comprises a process consisting of at 94° C. (30 seconds)—55° C. (30 seconds)—72° C. (1 minute). An NdeI-PstI fragment of about 0.5 kb isolated after digestion of an amplified DNA fragment obtained by PCR with NdeI and PstI, and a PstI-EcoRI fragment of about 1.1 kb isolated from the plasmid pF3SH92 were mixed and subcloned between the NdeI and EcoRI sites of plasmid vector pTV119Nd. The recombinant plasmid thus obtained was named pF3-19. In addition, *Escherichia coli* JM109 transformed with the plasmid was named *Escherichia coli* JM109/pF3-19. The transformant was found to possess high expression of F3.

(2) Determination of Nucleotide Sequence of Gene Encoding F3

Of the DNA insert in the plasmid pF3-19, obtained in Example 17(1), the region amplified by PCR was analyzed by the dideoxy method to determine its nucleotide sequence, and confirmed that there is no mutation caused by PCR.

Example 18
Preparation of Purified F3 Authentic Sample

*Escherichia coli* JM109/pF3-19 obtained in Example 17(1) was cultured for 16 hours in 500 ml×4 of LB medium (10 g/liter trypton, 5 g/liter yeast extract, 5 g/liter NaCl, pH 7.2) in which ampicillin was present at a concentration of 100 μg/ml. After harvesting, cells were suspended in 50 ml of sonication buffer [50 mM Tris-HCl, pH 8.0, 2 mM 2-mercaptoethanol, 10% glycerol, 2 mM PMSF (phenylmethanesulfonyl fluoride)], and the suspension was treated with an ultrasonic disrupter. After centrifugation at 12,000 rpm for 10 minutes, the supernatant was subjected to heat treatment at 80° C. for 15 minutes. Thereafter, centrifugation at 12,000 rpm for 10 minutes was again carried out to yield a heat-treated supernatant. Forty-four milliliters of the heat-treated supernatant was applied to RESOURCE Q column (manufactured by Pharmacia), previously equilibrated with buffer A described in Example 16, and the applied solution was chromatographed using FPLC system (manufactured by Pharmacia). The chromatogram was developed on a linear concentration gradient from 0 to 500 mM NaCl. To 11 ml of a solution of the fraction containing F3 eluted at 140 mM to 240 mM NaCl, 5.5 ml of buffer A containing 3 M ammonium sulfate was added, and this solution was applied to HiTrap butyl column (manufactured by Pharmacia), previously equilibrated with buffer A containing 1 M ammonium sulfate. After the column was washed with buffer A containing 1 M ammonium sulfate using FPLC system, F3 was eluted with buffer A containing 0.5 M ammonium sulfate. Six milliliters of this fraction was applied to HiTrap phenyl column (manufactured by Pharmacia), previously equilibrated with buffer A containing 0.5 M ammonium sulfate. After the column was washed with buffer A containing 0.5 M ammonium sulfate using FPLC system, F3 was eluted with buffer A. Using Centricon-10 (manufactured by Amicon), 9.5 ml of this fraction was concentrated, and 155 μl of the concentrate was applied to Superdex 200 gel filtration column (manufactured by Pharmacia), previously equilibrated with 50 mM Tris-HCl, pH 8.0, 2 mM 2-mercaptoethanol and 75 mM NaCl. The elution was carried out with the same buffer, and as a result, F3 was eluted at a position corresponding to a retention time of 42.1 minutes. From the comparative results in the position of the elution of a molecular weight marker under the same conditions, a molecular weight of about 25 kilodaltons was anticipated. On the basis that the theoretical value of the molecular weight of F3 is 37 kilodaltons, F3 is deduced to be a monomer.

Example 19
Preparation of Purified F5 Authentic Sample

*Escherichia coli* HMS174(DE3)/pF5NBPET, *Escherichia coli* HMS174(DE3) transformed with the plasmid pF5NBPET obtained in Example 12(4), was cultured for 16 hours in 500 ml×4 of LB medium (10 g/liter trypton, 5 g/liter yeast extract, 5 g/liter NaCl, pH 7.2) in which ampicillin was present at a concentration of 100 μg/ml. After harvesting, cells were suspended in 61 ml of sonication buffer, and the suspension was treated with using an ultrasonic disrupter. The disrupted cells were centrifuged at 12,000 rpm for 10 minutes, and thereafter the supernatant was subjected to heat treatment at 80° C. for 15 minutes. Thereafter, centrifugation at 12,000 rpm for 10 minutes was again carried out to yield a heat-treated supernatant. To 60.5 ml ammonium sulfate, 8.71 g of ammonium sulfate was added, and the mixture was stirred at 4° C. for 2 hours, and thereafter centrifugation at 12,000 rpm for 10 minutes was carried out. The precipitate was dissolved in 19 ml of buffer A and dialyzed against buffer A. The enzyme solution after dialysis was applied to RESOURCE Q column (manufactured by Pharmacia), previously equilibrated with buffer A, and the applied solution was chromatographed using FPLC system (manufactured by Pharmacia). The chromatogram was developed on a linear concentration gradient from 0 to 500 mM NaCl. Using Centricon-10 (manufactured by Amicon), 11 ml of a solution of a fraction containing F5 eluted at 350 mM to 450 mM NaCl was concentrated, and 222 μl of the concentrate was applied to Superdex 200 gel filtration column (manufactured by Pharmacia), previously equilibrated with 50 mM Tris-HCl, pH 8.0, 2 mM 2-mercaptoethanol and 75 mM NaCl. The elution was carried out with the same buffer, and as a result, F5 was eluted at a position corresponding to a retention time of 32.5 minutes. From the comparative results with the position of the elution of a molecular weight marker under the same conditions, a molecular weight of about 145 kilodaltons was anticipated. This molecular weight corresponds to the case where F5 has formed a heptamer.

Example 20
Preparation of Primers

On the basis of the nucleotide sequence of λDNA, eight kinds of primers, i.e., λ1B to λ5 and λ7 to λ9, were synthesized. The nucleotide sequences of the primers λ1B to λ5 and λ7 to λ9 are shown in SEQ ID NOs: 85 to 92, respectively, in Sequence Listing. The chain lengths of DNA fragments amplified by PCR using combinations of these primers with λDNA as a template are shown in Table 4.

TABLE 4

| Primer Pairs | Chain Length of DNA Fragment Amplified |
| --- | --- |
| λ1B/λ2 | 0.5 kb |
| λ1B/λ3 | 1 kb |
| λ1B/λ4 | 2 kb |
| λ1B/λ5 | 4 kb |
| λ1B/λ7 | 8 kb |
| λ1B/λ8 | 10 kb |
| λ1B/λ9 | 12 kb |

Example 21
Effects of F1 Protein on DNA Polymerase

The effects of the F1 protein obtained in Example 5 on PCR were examined. In order to carry out an amplification reaction of 1 to 4 kb DNA fragments using λDNA as a template, each of the primers λ1B and λ3, the primers λ1B and λ4, and the primers λ1B and λ5, were used as primer pairs to prepare reaction mixtures of the compositions shown below: 10 mM Tris-HCl, pH 9.2, 75 mM KCl, 6 mM MgCl$_2$, 0.4 mM each of dATP, dCTP, dGTP and dTTP, 0.01% BSA and 1.25 units of Pfu polymerase C, 500 pg of template DNA, 5 pmol each of the primers, 173 pmol of the F1 protein (final volume being 25 μl). Using each reaction mixture, the reaction was carried out in 30 cycles, wherein one cycle comprises a process consisting of at 98° C., 0 second—68° C., 0 second. The phrases "98° C., 0 second", "68° C., 0 second" etc. as used in the present specification indicate that the reaction apparatus was programmed so that the setting temperature is immediately shifted to the next one when the setting temperature is reached.

After termination of the reaction, 5 µl of the reaction mixture was electrophoresed on 1% agarose gel (manufactured by Takara Shuzo Co., Ltd.) to confirm amplified fragments.

As a result, the amplification of 1 kb, 2 kb and 4 kb DNA fragments, depending on the primer pairs used, was confirmed. On the other hand, when the above reaction mixture without the addition of the F1 protein was subjected to PCR under the above reaction conditions, no amplified fragments could be confirmed.

Example 22
Effects of F1, F3 and F5 Proteins on DNA Polymerase

The effects of the F1 protein obtained in Example 5, the F3 protein obtained in Example 18 and the F5 protein obtained in Example 19 were used to investigate the amplification of a 6 kb DNA fragment by PCR with λDNA as a template. Reaction mixtures of the same compositions as those used in Example 21 were prepared, except that the primers λ1 and λ6 were used as a primer pair. The F1 protein was added in an amount of 173 pmol, the F3 protein was added in an amount of 10 pmol, and the F5 protein was added in an amount of 1 pmol, respectively, to make up a final volume of 25 µl. Using each reaction mixture, the reaction was carried out in 30 cycles, wherein one cycle comprises a process consisting of at 98° C., 1 second—68° C., 2 minutes. After termination of the reaction, 5 µl of the reaction mixture was electrophoresed on 1% agarose gel to confirm amplified fragments.

As a result, the amplification of a 6 kb DNA fragment was confirmed in the presence of any of the F1, F3 and F5 proteins. On the other hand, when these proteins were not added, no amplified fragments could not be confirmed.

Example 23
Effects of F2 and F4 Proteins on DNA Polymerase

The effects of the F2 protein obtained in Example 6 and the F4 protein obtained in Example 7 were used to investigate the amplification reaction of a 4 kb DNA fragment by PCR with EDNA as a template. Reaction mixtures of the same compositions as those used in Example 21 were prepared, except that the primers λ1B and λ5, as a primer pair, 0.75 units of Pfu polymerase C and 1 ng of template λDNA were used. The F2 protein and the F4 protein were each added in an amount of 1.095 pmol to the reaction mixture to make up a final volume of 25 µl. Using each reaction mixture, the reaction was carried out in 25 cycles, wherein one cycle comprises a process consisting of at 94° C., 30 seconds—55° C., 30 seconds—72° C., 2 minutes. After termination of the reaction, 5 µl of the reaction mixture was electrophoresed on 1% agarose gel to confirm amplified fragments.

As a result, the amplification of a 4 kb fragment was confirmed in the presence of any of the F2 and F4 proteins. On the other hand, when these proteins were not added, no amplified fragment was confirmed.

Example 24
Effects of rRFC-M Complex on DNA Polymerases

In order to examine the effects of the rRFC-M complex on the primer extension reactions of various polymerases, the activities of Pfu polymerase C and Pfu DNA polymerase (α-type DNA polymerase, manufactured by STRATAGENE) were compared for cases where the rRFC-M complex and F7 are coexistent, and for cases where F7 exists alone.

Figure 17:
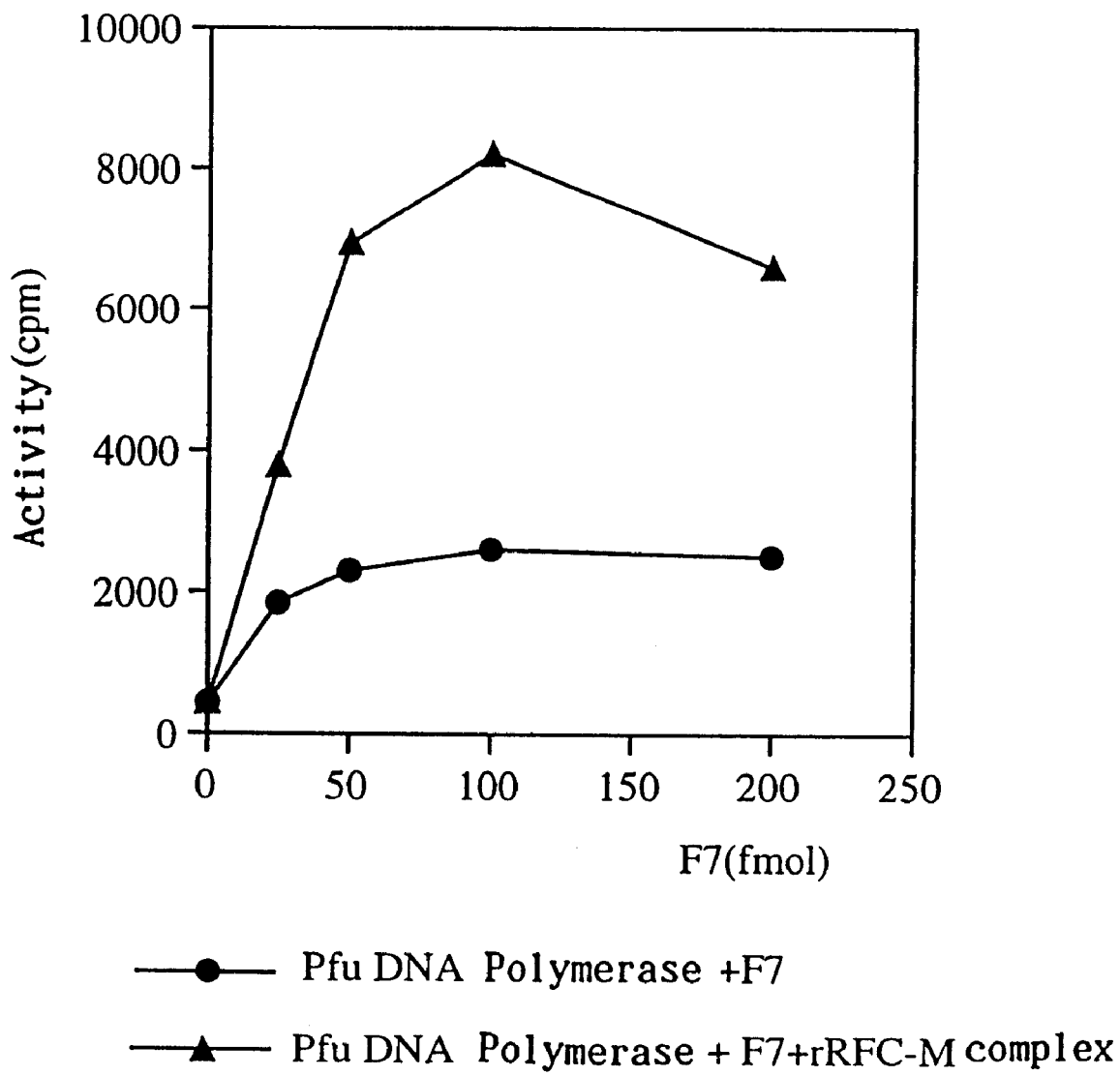
FIG. 17 is a graph showing DNA polymerase activity, when F7, or F7 and rRFC-M complex are added.

DNA polymerase activities were determined in the same manner as the method described in Example 8(5), except that 50 fmol of Pfu polymerase C or Pfu DNA polymerase was used, and that 400 fmol of the rRFC-M complex and 0 to 200 fmol of F7 were added. The results of the case of using Pfu DNA polymerase are shown in FIG. 17. The effects on Pfu DNA polymerase were such that the activity was more elevated in the case of coexistence of the rRFC-M complex and F7 than the case of F7 alone. In addition, the effects on Pfu polymerase C showed the same tendency as those of Pfu DNA polymerase.

Example 25
Effects of Coexistence of rRFC-M Complex and F7 Protein on PCR

In order to carry out an amplification reaction of a 4 kb DNA fragment using EDNA as a template, reaction mixtures of the same compositions as those used in Example 21 were prepared, except that the primers λ1B and λ5 and 0.375 units of Pfu polymerase C were used. The rRFC-M complex was added in an amount of 312.5 fmol, and the F7 protein was added in an amount of 125 fmol, respectively, to the reaction mixture to make up a final volume of 25 µl. Using each reaction mixture, the reaction was carried out in 30 cycles, wherein one cycle comprises a process consisting of at 98° C., 0 second—68° C., 10 seconds. After termination of the reaction, 5 µl of the reaction mixture was electrophoresed on 1% agarose gel (manufactured by Takara Shuzo Co., Ltd.) to confirm amplified fragments.

As a result, the amplification of a 4 kb DNA fragment, depending on the primer pair used, was confirmed in the case of the system where the rRFC-M complex and the F7 protein were coexistent. On the other hand, when these proteins were not added, no amplified fragments could be confirmed.

Furthermore, a similar experiment was carried out for an amplification reaction of 8 to 12 kb DNA fragments using λDNA as a template. Reaction mixtures of the same compositions as those used in Example 21 were prepared, except that each of the primers λ1B and λ7, the primers λ1B and λ8, and the primers λ1B and λ9 were used as primer pairs, and further 0.375 units of Pfu polymerase C, and 2.5 ng of template λDNA were used. The rRFC-M complex was added in an amount of 312.5 fmol, and the F7 protein was added in an amount of 125 fmol, respectively, to the reaction mixture to make up a final volume of 25 µl. Using each reaction mixture, the reaction was carried out in 30 cycles, wherein one cycle comprises a process consisting of at 98° C., 0 second—68° C., 3 minutes. After termination of the reaction, 5 µl of the reaction mixture was electrophoresed on 1% agarose gel (manufactured by Takara Shuzo Co., Ltd.) to confirm amplified fragments.

As a result, the amplification of 8 kb, 10 kb and 12 kb DNA fragments, depending on the primer pairs used, was confirmed in the case of the system where the rRFC-M complex and the F7 protein were coexistent. On the other hand, when these proteins were not added, only a 8 kb DNA fragment was confirmed.

Example 26
Effects of Coexistence of rRFC-M Complex and F7 Protein on Pfu DNA Polymerase In order to carry out an amplification reaction of a 4 kb DNA fragment using λDNA as a template, using each of the primers λ1B and λ3, the primers λ1B and λ4, and the primers λ1B and λ5, as primer pairs, reaction mixtures of the compositions shown below were prepared: buffer supplied with Pfu DNA polymerase, 0.2 mM each of dATP, dCTP, dGTP and dTTP, and 0.5 units each of Pfu polymerase, 500 pg of template DNA, 2.5 pmol of each primer, 2.5 pmol of the rRFC-M complex protein, and 0.5 pmol of the F7 protein (final volume being 25 µl). Using each reaction mixture, the reaction was carried out in 25 cycles, wherein one cycle comprises a process consisting of at 94° C., 30 seconds—55° C., 30 seconds—72° C., 1 minute. After termination of the reaction, 5 µl of the reaction mixture was electrophoresed on 1% agarose gel to confirm amplified fragments.

As a result, the amplification of 1 kb, 2 kb and 4 kb DNA fragments, depending on the primer pairs used, was confirmed in the case of the system where the rRFC-M complex and the F7 protein were coexistent. On the other hand, when these proteins were not added, only 1 kb to 2 kb DNA fragments were confirmed.

Example 27
Effects of Coexistence of rRFC-M Complex and F7 Protein on Mixed DNA Polymerase The effects of the coexistence of the rRFC-M complex and the F7 protein on PCR using a mixture of two kinds of DNA polymerases were examined.

In order to carry out an amplification reaction of a 1 kb DNA fragment using λDNA as a template, using the primers λ1B and λ3 as a primer pair, reaction mixtures of the compositions shown below were prepared: buffer supplied with TaKaRa LA Taq (Mg Plus), 0.4 mM each of dATP, dCTP, dGTP and dTTP, 1.25 units of LA Taq DNA polymerase (manufactured by Takara Shuzo Co., Ltd.), 500 pg of template DNA, 5 pmol of each primer, 62.5 fmol of the RFC complex protein, and 12.5 fmol of the F7 protein (final volume being 25 µl). Using each reaction mixture, the reaction was carried out in 30 cycles, wherein one cycle comprises a process consisting of at 98° C., 0 second—68° C., 10 seconds. After termination of 10 the reaction, 5 µl of the reaction mixture was electrophoresed on 1% agarose gel to confirm amplified fragments.

As a result, there can be confirmed that a DNA fragment of 1 kb was most efficiently amplified, in the case of the system where the rRFC-M complex and the F7 protein were added, as a result of comparison of the system where the rRFC-M complex and the F7 protein were added with the system where the rRFC-M complex alone was added, the system where the F7 protein alone was added, or the system where LA Taq DNA polymerase alone was added.

Industrial Applicability

According to the present invention, there can be provided a DNA polymerase-associated factor capable of enhancing DNA synthesizing-activity of a DNA polymerase. The factor has an action on various DNA polymerases, and also can be utilized in various processes in which a DNA polymerase is used, so that the factor is useful as a reagent for studies in genetic engineering. Further, it is now possible to produce the enzyme by genetic engineering techniques using a gene encoding the DNA polymerase-associated factor of the present invention.

What is claimed is:

1. An isolated DNA polymerase-associated factor possessing an activity of enhancing DNA synthesizing-activity of a DNA polymerase, wherein the factor comprises at least one of amino acid sequences selected from the group consisting of SEQ ID NOS: 1, 3, 19, 27, 34, 64, 70 and 80.

2. The isolated DNA polymerase-associated factor according to claim 1, further possessing an activity of binding to a DNA polymerase.

3. The isolated DNA polymerase-associated factor according to claim 2, wherein the DNA polymerase is a protein comprising a DNA polymerase-constituting protein having the amino acid sequence as shown in SEQ ID NO: 5 or 6.

4. A method of DNA synthesis by using a DNA polymerase, comprising synthesizing DNA in the presence of the DNA polymerase-associated factor of claim 1.

5. The method of DNA synthesis according to claim 4, wherein DNA is synthesized in the presence of two or more kinds of isolated DNA polymerase-associated factors.

6. The method of DNA synthesis according to claim 5, wherein DNA is synthesized in the presence of F7, PFU-RFC and PFU-RFCLS as an isolated DNA polymerase-associated factor.

7. The method of DNA synthesis according to any one of claims 4–6, wherein said DNA polymerase is a thermostable DNA polymerase.

8. The method of DNA synthesis according to claim 7, wherein the synthesis is carried out by PCR method.

9. A kit for in vitro DNA synthesis, comprising the isolated DNA polymerase-associated factor of claim 1.

10. The kit according to claim 9, further comprising a reagent required for DNA synthesis.

11. The kit according to claim 9 or 10, comprising two or more kinds of isolated DNA polymerase-associated factors.

12. The kit according to claim 11, comprising F7, PFU-RFC and PFU-RFCLS as an isolated DNA polymerase-associated factor.

13. The kit according to claim 9 or 10, comprising a thermostable DNA polymerase as a DNA polymerase.

14. The kit according to claim 11, comprising a thermostable DNA polymerase as a DNA polymerase.

15. The kit according to claim 14, comprising a thermostable DNA polymerase as a DNA polymerase.

* * * * *